United States Patent
D'Souza et al.

(12)

(10) Patent No.: US 6,450,641 B2
(45) Date of Patent: *Sep. 17, 2002

(54) METHOD OF CORNEAL ANALYSIS USING A CHECKERED PLACIDO APPARATUS

(75) Inventors: Henry M. D'Souza, Cypress, TX (US); Edwin J. Sarver, Merritt Island, FL (US); Youssef S. Wakil, Houston, TX (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/828,148

(22) Filed: Apr. 9, 2001

Related U.S. Application Data

(63) Continuation of application No. 09/102,839, filed on Jun. 23, 1998, now Pat. No. 6,213,605, which is a continuation-in-part of application No. 07/891,961, filed on Jun. 2, 1992, now abandoned.

(51) Int. Cl.[7] ............................................. A61B 3/10
(52) U.S. Cl. .................................................. 351/212
(58) Field of Search ........................... 351/200, 205, 351/206, 211, 212, 221, 246, 247; 356/124; 606/4, 5

(56) References Cited

U.S. PATENT DOCUMENTS

| | | | |
|---|---|---|---|
| 2,480,737 A | 8/1949 | Jayle | |
| 3,074,407 A | 1/1963 | Moon | |
| 3,476,112 A | 11/1969 | Elstein | |
| 3,697,889 A | 10/1972 | Dewey, Jr. | |
| 3,743,965 A | 7/1973 | Offner | |
| 3,848,104 A | 11/1974 | Locke | |
| 3,938,058 A | 2/1976 | Yamamoto | |
| 3,982,541 A | 9/1976 | L'Esperance, Jr. | |
| 3,983,507 A | 9/1976 | Tang et al. | |
| 4,169,663 A | 10/1979 | Murr | |
| 4,180,751 A | 12/1979 | Ammann | |

(List continued on next page.)

FOREIGN PATENT DOCUMENTS

| | | |
|---|---|---|
| CA | 1243732 | 10/1984 |
| EP | 0 151869 A2 | 8/1985 |
| EP | 0296982 A1 | 6/1988 |

(List continued on next page.)

OTHER PUBLICATIONS

Qiushi Ren, Raymond P. Galitis, Keith P. Thompson, & J.T. Lin, "Ablation of the Cornea and Synthetic Polymers Using a UV (213 nm) Solid State Laser", IEEE Journal of Quatum Electronics, Dec. 1990, pp. 2284–2288.

(List continued on next page.)

*Primary Examiner*—George Manuel
(74) *Attorney, Agent, or Firm*—William H. Bollman

(57) ABSTRACT

A method for analysis of the curvature of the surface of a cornea using a checkered placido comprises, projecting the image of the checkered placido onto a patient's cornea, detecting the image of the checkered placido reflected off of the cornea, detecting a plurality of nodal points from the reflected image, determining the mean curvature at a plurality of nodal points and analyzing the mean curvature at a plurality of nodal points in order to produce a graphic display of the estimated actual curvature of the cornea.

22 Claims, 57 Drawing Sheets

U.S. PATENT DOCUMENTS

| | | |
|---|---|---|
| 4,349,907 A | 9/1982 | Campillo et al. |
| 4,386,428 A | 5/1983 | Baer |
| 4,423,728 A | 1/1984 | Lieberman |
| 4,461,294 A | 7/1984 | Baron |
| 4,477,159 A | 10/1984 | Mizuno et al. |
| 4,520,816 A | 6/1985 | Schachar et al. |
| 4,526,171 A | 7/1985 | Schachar |
| 4,538,608 A | 9/1985 | L'Esperance, Jr. |
| 4,546,773 A | 10/1985 | Kremer et al. |
| 4,573,467 A | 3/1986 | Rich et al. |
| 4,580,559 A | 4/1986 | L'Esperance, Jr. |
| 4,598,714 A | 7/1986 | Kremer et al. |
| 4,619,259 A | 10/1986 | Graybill et al. |
| 4,633,866 A | 1/1987 | Peyman et al. |
| 4,653,495 A | 3/1987 | Nanaumi |
| 4,662,370 A | 5/1987 | Hoffman et al. |
| 4,665,913 A | 5/1987 | L'Esperance, Jr. |
| 4,669,466 A | 6/1987 | L'Esperance, Jr. |
| 4,688,570 A | 8/1987 | Kramer et al. |
| 4,718,418 A | 1/1988 | L'Esperance, Jr. |
| 4,720,189 A | 1/1988 | Heyman et al. |
| 4,721,379 A | 1/1988 | L'Esperance, Jr. |
| 4,729,372 A | 3/1988 | L'Esperance, Jr. |
| 4,729,373 A | 3/1988 | Peyman |
| 4,732,148 A | 3/1988 | L'Esperance, Jr. |
| 4,764,930 A | 8/1988 | Bille et al. |
| 4,770,172 A | 9/1988 | L'Esperance |
| 4,773,414 A | 9/1988 | L'Esperance, Jr. |
| 4,784,135 A | 11/1988 | Blum et al. |
| 4,798,204 A | 1/1989 | L'Esperance, Jr. |
| 4,807,623 A | 2/1989 | Lieberman |
| 4,838,266 A | 6/1989 | Koziol et al. |
| 4,838,679 A | 6/1989 | Bille |
| 4,840,175 A | 6/1989 | Peyman |
| 4,848,340 A | 7/1989 | Bille et al. |
| 4,856,513 A | 8/1989 | Muller |
| 4,862,886 A | 9/1989 | Clarke et al. |
| 4,896,015 A | 1/1990 | Taboada et al. |
| 4,903,695 A | 2/1990 | Warner et al. |
| 4,907,586 A | 3/1990 | Bille et al. |
| 4,911,711 A | 3/1990 | Telfair et al. |
| 4,925,523 A | 5/1990 | Braren et al. |
| 4,941,093 A | 7/1990 | Marshall et al. |
| 4,968,130 A | 11/1990 | Hideshima et al. |
| 4,975,918 A | 12/1990 | Morton |
| 4,993,826 A | 2/1991 | Yoder |
| 4,994,058 A | 2/1991 | Raven et al. |
| 5,019,074 A | 5/1991 | Muller |
| 5,052,004 A | 9/1991 | Gratze et al. |
| 5,063,942 A | 11/1991 | Kilmer et al. |
| 5,065,046 A | 11/1991 | Guyer |
| 5,074,859 A | 12/1991 | Koziol |
| 5,102,409 A | 4/1992 | Balgorod |
| 5,108,388 A | 4/1992 | Trokel |
| 5,108,412 A | 4/1992 | Krumeich et al. |
| 5,133,726 A | 7/1992 | Ruiz et al. |
| 5,144,630 A | 9/1992 | Lin |
| 5,163,934 A | 11/1992 | Munnerlyn |
| 5,163,936 A | 11/1992 | Black et al. |
| 5,182,759 A | 1/1993 | Anthon et al. |
| 5,188,631 A | 2/1993 | L'Esperance, Jr. |
| 5,196,006 A | 3/1993 | Klopotek et al. |
| 5,207,668 A | 5/1993 | L'Esperance, Jr. |
| 5,217,452 A | 6/1993 | O'Donnell |
| 5,219,343 A | 6/1993 | L'Esperance, Jr. |
| 5,219,344 A | 6/1993 | Yoder, Jr. |
| 5,222,960 A | 6/1993 | Poley |
| 5,226,903 A | 7/1993 | Mizuno |
| 5,250,062 A | 10/1993 | Hanna |
| 5,257,988 A | 11/1993 | L'Esperance, Jr. |
| 5,263,950 A | 11/1993 | L'Esperance, Jr. |
| 5,284,477 A | 2/1994 | Hanna et al. |
| 5,288,292 A | 2/1994 | Giraud et al. |
| 5,290,301 A | 3/1994 | Lieberman |
| 5,312,320 A | 5/1994 | L'Esperance, Jr. |
| 5,324,281 A | 6/1994 | Muller |
| 5,334,190 A | 8/1994 | Seiler |
| 5,336,217 A | 8/1994 | Buys et al. |
| 5,345,534 A | 9/1994 | Najm et al. |
| 5,349,590 A | 9/1994 | Amirkhanian et al. |
| 5,350,374 A | 9/1994 | Smith |
| 5,353,262 A | 10/1994 | Yakymyshyn et al. |
| 5,360,424 A | 11/1994 | Klopotek |
| 5,363,388 A | 11/1994 | Shi et al. |
| 5,364,388 A | 11/1994 | Koziol |
| 5,370,641 A | 12/1994 | O'Donnell, Jr. |
| 5,395,356 A | 3/1995 | King et al. |
| 5,395,362 A | 3/1995 | Sacharoff et al. |
| 5,405,355 A | 4/1995 | Peyman et al. |
| 5,411,501 A | 5/1995 | Klopotek |
| 5,423,801 A | 6/1995 | Marshall et al. |
| 5,425,727 A | 6/1995 | Koziol |
| 5,425,729 A | 6/1995 | Ishida et al. |
| 5,437,658 A | 8/1995 | Muller et al. |
| 5,441,511 A | 8/1995 | Hanna |
| 5,442,487 A | 8/1995 | Mizuno |
| 5,445,633 A | 8/1995 | Nakamura et al. |
| 5,461,212 A | 10/1995 | Seiler et al. |
| 5,470,329 A | 11/1995 | Sumiya |
| 5,474,548 A | 12/1995 | Knopp et al. |
| 5,480,396 A | 1/1996 | Simon et al. |
| 5,505,723 A | 4/1996 | Muller |
| 5,507,741 A | 4/1996 | L'Esperance, Jr. |
| 5,507,799 A | 4/1996 | Sumiya |
| 5,520,679 A | 5/1996 | Lin |
| 5,549,597 A | 8/1996 | Shimmick et al. |
| 5,556,395 A | 9/1996 | Shimmick et al. |
| 5,582,752 A | 12/1996 | Zair |
| 5,599,340 A | 2/1997 | Simon et al. |
| 5,613,965 A | 3/1997 | Muller |
| 5,624,436 A | 4/1997 | Nakamura et al. |
| 5,634,920 A | 6/1997 | Hohla |
| 5,637,109 A | 6/1997 | Sumiya |
| 5,646,791 A | 7/1997 | Glockler |
| 5,651,784 A | 7/1997 | Klopotek |
| 5,683,379 A | 11/1997 | Hohla |
| 5,684,562 A | 11/1997 | Fujieda |
| 5,711,762 A | 1/1998 | Trokel |
| 5,713,892 A | 2/1998 | Shimmick |
| 5,735,843 A | 4/1998 | Trokel |
| 5,782,822 A | 7/1998 | Telfair et al. |
| 5,849,006 A | 12/1998 | Frey et al. |
| 5,865,830 A | 2/1999 | Parel et al. |
| 6,270,221 B1 * | 8/2001 | Liang et al. ............ 351/221 |
| 6,271,914 B1 * | 8/2001 | Frey et al. ............ 356/124 |

FOREIGN PATENT DOCUMENTS

| | | |
|---|---|---|
| EP | 0151869 B1 | 1/1990 |
| EP | 0368512 A2 | 5/1990 |
| EP | 0207648 B1 | 8/1990 |
| EP | 0418890 A3 | 3/1991 |
| EP | 0602756 A1 | 6/1994 |
| WO | PCT/FR87/00139 | 11/1987 |
| WO | PCT/US92/09625 | 5/1993 |
| WO | PCT/US93/00327 | 8/1993 |
| WO | PCT/US94/02007 | 9/1994 |
| WO | PCT/EP95/01287 | 10/1995 |

OTHER PUBLICATIONS

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, "Third—Harmonic Generation of an Alexandrite Laser in $\beta-BaB_2O_4$," Applied Physics Letters, May 1989, pp. 1206–1208.

Conference on Lasers and Electro–Optics, Optical Society of America, Apr. 1989, p. 390.

Barraquer, "Lamellar Keratoplasty (special techniques)" Annals of Ophthalmology, Jun. 1972, pp. 437–469.

Burnett, "Company Denies Delay in Approval for Laser", Orlando Sentinel, Feb. 1993, pp. 12–13.

Burnett, "Medical Technology", Orlando Sentinel, Feb. 1993, pp. 1–5.

Gailitis et al., "Solid State Ultraviolet Laser (213 nm) Ablation of the Cornea and Synthetic Collagen Lenticules", Lasers in Surgery and Medicine, Dec. 1991, pp. 556–562.

Gartry et al., "Excimer Laser Photorefractive Keratectomy", Ophthalmology, Aug. 1992, pp. 1210–1219.

Gilbert, "Corneal Topography: In Search of the Excimer Islands", Eye Care Technology, Oct. 1993, pp. 23–28.

L'Esperance, "New Laser Systems, Their Potential Clinical Usefulness, and Investigative Laser Procedures", Ophthalmic Lasers, 1989, pp. 995–1045.

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technolgies, Jun. 1992, pp. 266–275.

Marguerite B. McDonald et al, "Central Photorefractive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofiling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser in Situ Keratomileusis and Photorefractive Keratectomy for Correction of High Myopia", Journal of Refractive and Corneal Surgery, Sep. 1994, pp. 498–510.

Ren et al, "Corneal Refractive Surgery Using an Ultra–Violet (213nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blind Human Eyes" Refractive and Corneal Laser Surgery, Jun. 1990, pp. 165–173.

Serdarevic, "Corneal Laser Surgery", Ophthalmic Lasers, 1989, pp. 919–970.

Steinert et al, "Laser Corneal Surgery", Laser Research Laboratory, 1998, pp. 151–154.

Thompson et al, "Philosophy and Technique for Excimer Laser Phototheraputic Keratectomy", Refractive and Corneal Surgery, Apr. 1993, pp. 81–85.

Trokel et al "Excimer Laser Surgery of the Cornea", American Journal of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Sep. 1991, pp. 1338–1347.

* cited by examiner

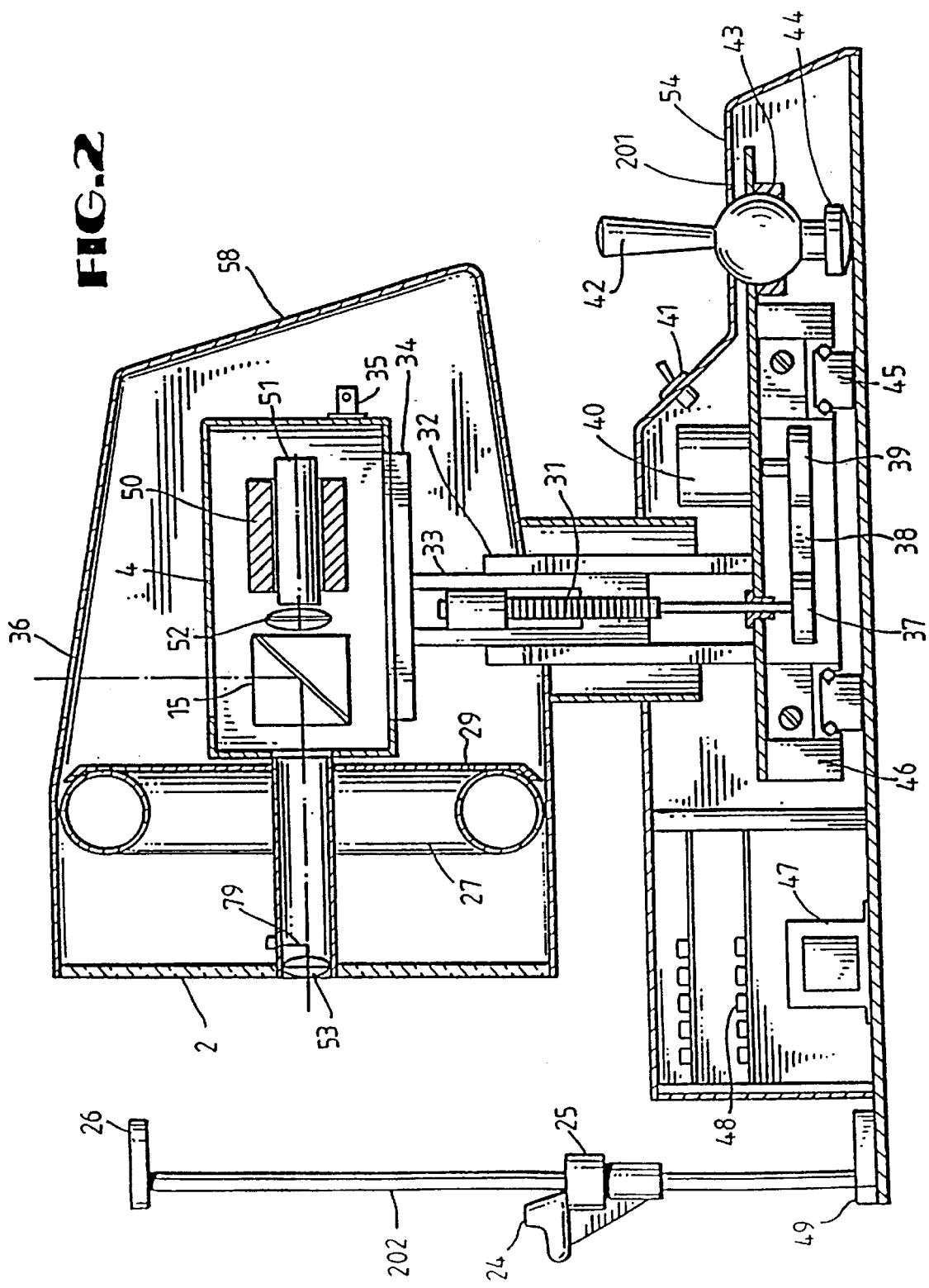

AQUIRE DATA
1. RIGHT EYE (O.D)
2. LEFT EYE (O.S)

SELECT DISPLAY FORMAT
1. KERATOMETRIC DATA
2. TABULAR DATA
3. CONTAC LENS MAP
4. PROFILE GRAPH FUNCTIONS
5. COLOR MAP FUNCTIONS
6. DATA OVERVIEW
7. DISPLAY EYE IMAGE

PATIENT DIRECTORY
| PATIENT | ID# | PATIENT GROUP |
|---|---|---|
| DOE, JOHN | 0000000 | KERATOCONUS |
| DOE, JANE | 000000000 | MEDICARE |
| SMITH, TOM | 0000 | MEDICARE |
| SMITH, JUDY | 00000 | DR. WILSON |
| BROWN, JOSEPH | 000000000 | TRAUMA PAPER |
| GREEN, LARRY | 00000 | KERATOCONUS |
| SANDERS, JOE | 0000000 | KERATOCONUS |

MAIN MENU
1. AQUIRE DATA
2. REVIEW/COMPARE OLD DATA
3. CALIBRATE INSTRUMENT
4. PATIENT DATA UTILITIES
5. EDIT PROGRAM PROFILE

CALIBRATION MENU
1. 55.06 DIOPTER SPHERE
2. 47.54 DIOPTER SPHERE
3. 42.51 DIOPTER SPHERE
4. 37.50 DIOPTER SPHERE
5. CHECK CALIBRATION VALIDITY
6. STORE CALIBRATION TO HARD DISK

FIG.3A-1

PATIENT DATA UTILITIES
1. FORMAT A FLOPPY DISK
2. COPY PATIENT TO FLOPPY DISK
3. COPY PATIENT FROM FLOPPY DISK
4. DELETE PATIENT EXAM(S)
5. DELETE PATIENT(S)
6. CHANGE PATIENT ID IN DATABASE
7. CHANGE PATIENT GROUP IN DATABASE

FIG. 3A-2

PATIENT INFORMATION
NAME: ID#:
STREET:
CITY: STATE: ZIP:
GROUP:
REFERRED BY:
COMMENTS:
EXAM DATE: (AUTOMATICALLY
 INSERTED BY THE SYSTEM)

SELECT DISPLAY FORMAT
1. KERATOMETRIC DATA
2. TABULAR DATA
3. CONTAC LENS MAP
4. PROFILE GRAPH FUNCTIONS
5. COLOR MAP FUNCTIONS
6. DATA OVERVIEW
7. DISPLAY EYE IMAGE

SAVE/ERASE PATIENT EXAM
1. NEW PATIENT
2. EXISTING PATIENT
3. DO NOT SAVE (SAME AS
 PRESSING ESC NOW)

EXAM DIRECTORY (JOHN DOE)
| EXAM DATE | EXAM EYE | COMMENTS |
|---|---|---|
| MON 08:30, JAN 22, 1990 | LEFT | INITIAL EXAM |
| MON 08:31, JAN 22, 1990 | RIGHT | INITIAL EXAM |
| TUE 13:00, FEB 06, 1990 | LEFT | 1 WEEK POST RK |
| TUE 13:03 FEB 06, 1990 | RIGHT | 2 WEEKS POST RK |

LEFT EYE  PATIENT ID: 003666
FRI 19:07, JAN 19 1990

ACTUAL    ORTHOGONAL

3mm ZONE (CENTRAL)    40.37 / 38.52    89° / 179°

5mm ZONE (MID-PERIPHERAL)    41.82 / 40.03    82° / 172°

7mm ZONE (PERIPHERAL)    43.21 / 41.25    68° / 158°

LEFT EYE  PATIENT ID: 003666
FRI 19:07, JAN 19 1990

ASTIGMATISM TORQUE

3mm ZONE (CENTRAL)

5mm ZONE (MID-PERIPHERAL)

7mm (PERIPHERAL)

43.21
41.82
41.25
40.37
40.03
38.52

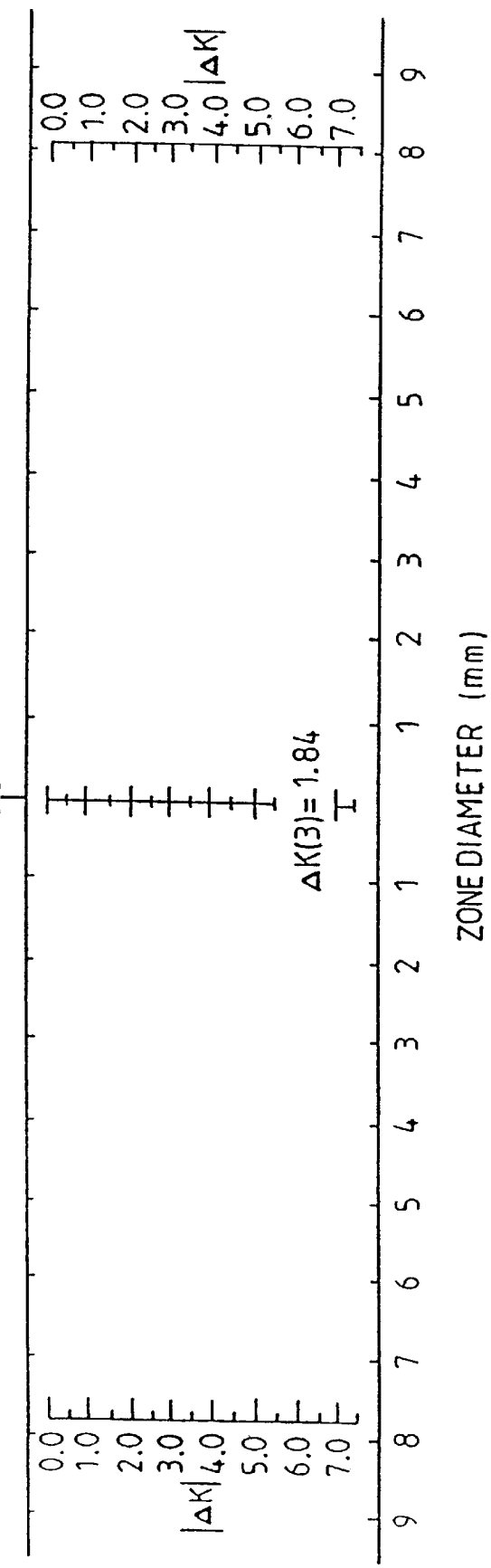

FIG.3E-1

LEFT EYE

MAJOR AXIS (AT 170 DEGREES)

PATIENT ID: 003666
FRI 19:07, JAN 19 1990

| TMP QUAD | ZONE | RADIUS(mm) | DIOPTERS | NAS QUAD | ZONE | RADIUS(mm) | DIOPTERS |
|---|---|---|---|---|---|---|---|
| #00 | 1.14 | 8.99 | 37.54 | #00 | 1.17 | 8.99 | 37.54 |
| #01 | 1.55 | 9.00 | 37.50 | #01 | 1.58 | 8.98 | 37.58 |
| #02 | 1.95 | 8.99 | 37.54 | #02 | 1.96 | 8.94 | 37.75 |
| #03 | 2.38 | 8.97 | 37.62 | #03 | 2.42 | 8.89 | 37.96 |
| #04 | 2.82 | 8.95 | 37.70 | #04 | 2.83 | 8.80 | 38.35 |
| #05 | 3.27 | 8.92 | 37.83 | #05 | 3.25 | 8.69 | 38.83 |
| #06 | 3.69 | 8.92 | 37.83 | #06 | 3.64 | 8.58 | 39.33 |
| #07 | 4.17 | 8.87 | 38.04 | #07 | 4.06 | 8.46 | 39.89 |
| #08 | 4.62 | 8.81 | 38.30 | #08 | 4.47 | 8.34 | 40.46 |
| #09 | 5.03 | 8.73 | 38.65 | #09 | 4.88 | 8.23 | 41.00 |
| #10 | 5.48 | 8.65 | 39.01 | #10 | 5.28 | 8.13 | 41.51 |
| #11 | 5.91 | 8.58 | 39.33 | #11 | 5.68 | 8.06 | 41.87 |
| #12 | 6.32 | 8.51 | 39.65 | #12 | 6.09 | 8.03 | 42.02 |
| #13 | 6.78 | 8.44 | 39.98 | #13 | 6.56 | 8.03 | 42.02 |
| #14 | 7.20 | 8.33 | 40.51 | #14 | 7.04 | 8.00 | 42.18 |
| #15 | 7.45 | 8.24 | 40.95 | #15 | 7.41 | 7.96 | 42.39 |

FIG. 3E-2

LEFT EYE

MINOR AXIS (AT 07 DEGREES)

| INF QUAD | ZONE | RADIUS(mm) | DIOPTERS | | SUP QUAD | ZONE | RADIUS(mm) | DIOPTERS |
|---|---|---|---|---|---|---|---|---|
| #00 | 1.08 | 8.50 | 39.70 | | #00 | 1.10 | 8.43 | 40.03 |
| #01 | 1.47 | 8.62 | 39.15 | | #01 | 1.47 | 8.36 | 40.37 |
| #02 | 1.87 | 8.61 | 39.06 | | #02 | 1.81 | 8.37 | 40.32 |
| #03 | 2.25 | 8.61 | 39.06 | | #03 | 2.19 | 8.31 | 40.61 |
| #04 | 2.64 | 8.63 | 39.10 | | #04 | 2.61 | 8.25 | 40.90 |
| #05 | 3.09 | 8.62 | 39.15 | | #05 | 2.98 | 8.17 | 41.30 |
| #06 | 3.50 | 8.59 | 39.28 | | #06 | 3.39 | 8.10 | 41.66 |
| #07 | 3.92 | 8.54 | 39.51 | | #07 | 3.79 | 8.03 | 42.02 |
| #08 | 4.34 | 8.47 | 39.84 | | #08 | 4.23 | 7.98 | 42.29 |
| #09 | 4.75 | 8.39 | 40.22 | | #09 | 4.63 | 7.93 | 42.55 |
| #10 | 5.12 | 8.30 | 40.66 | | #10 | 5.02 | 7.89 | 42.77 |
| #11 | 5.52 | 8.21 | 41.10 | | #11 | 5.44 | 7.85 | 42.99 |
| #12 | 5.89 | 8.12 | 41.56 | | #12 | 5.84 | 7.81 | 43.21 |
| #13 | 6.29 | 8.04 | 41.97 | | #13 | 6.26 | 7.75 | 43.54 |
| #14 | 6.65 | 7.88 | 42.82 | | #14 | 6.64 | 7.65 | 44.11 |
| #15 | 6.81 | 7.75 | 43.54 | | #15 | 6.93 | 7.57 | 44.58 |

FIG. 3F-1

PATIENT ID: 003666
THU 18:02, MAY 17 1990

AVERAGE CURVATURE
OVERALL = 8.36 (40.37D)
 8mm = 8.13 (41.51D)
 7mm = 8.15 (41.41D)
 6mm = 8.23 (41.00D)
 5mm = 8.37 (40.32D)
 4mm = 8.56 (39.42D)
 3mm = 8.70 (38.79D)
 2mm = 8.81 (38.30D)
 1mm = 8.88 (38.00D)
 0mm = 8.89 (37.96D)

LEFT EYE

NAS — TMP

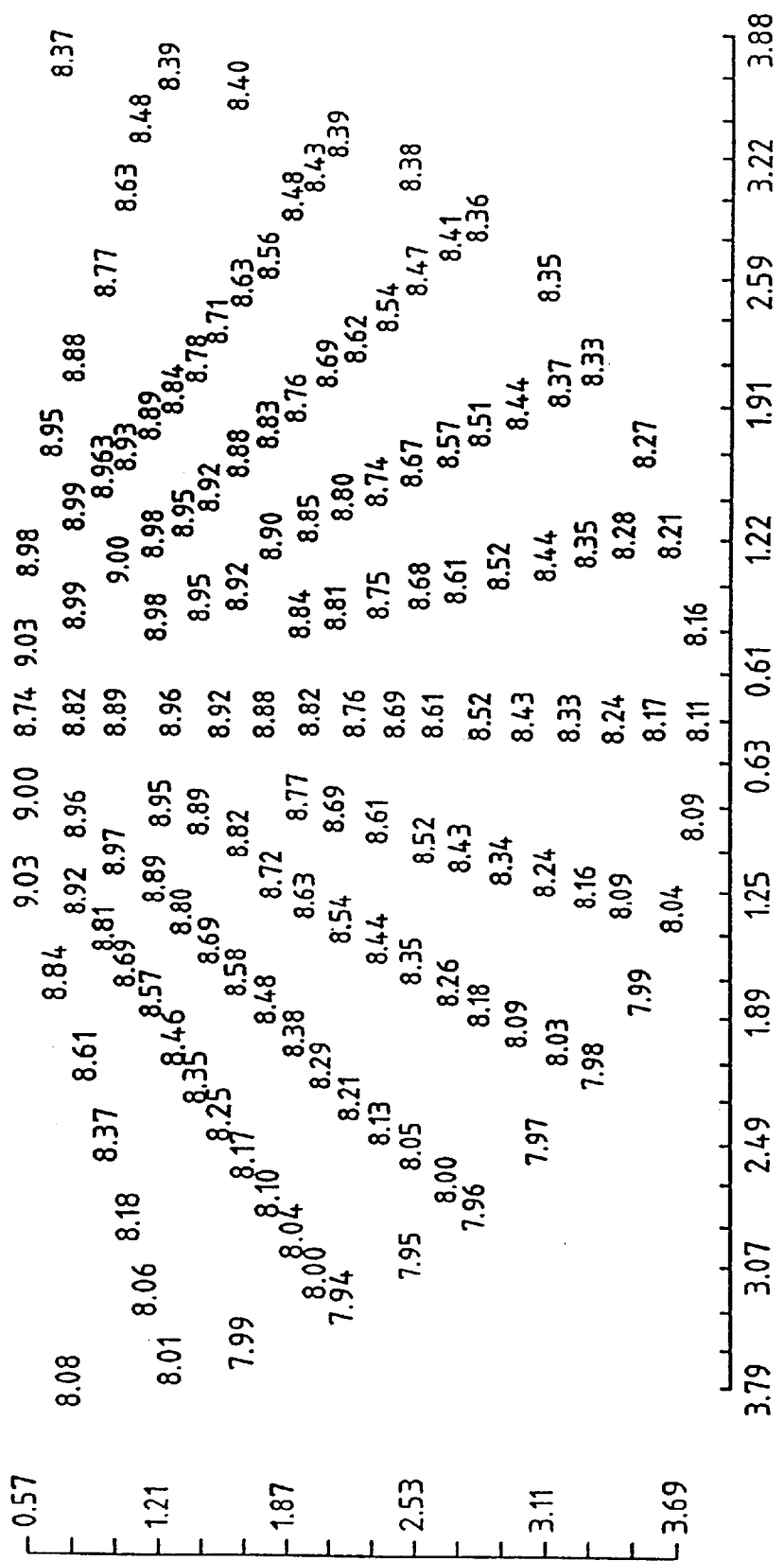

COMPARATIVE ISODIOPTRIC MAPPING

FIG.3K

| | | |
|---|---|---|
| LEFT EYE | | PATIENT ID: 122866 |
| | | SUN 17:52, OCT 14 1990 |

CENTRAL RAD: 44.29D@153° / 44.76D@56°
SLOPE FACTORS: 6.86mm AD / 4.26mm AD
VISIBLE IRIS DIAMETER:
FISSURE MEASURMENTS:
RX:
LENS DIAMETER: 8.86
DIAGNOSTIC LENS CPC (D):
DIAGNOSTIC LENS POWER:
TOTAL POWER OF DIAG. LENS:
REFRACTION OVER DIAG. LENS:
NEED OF THE EYE:
CPC OF FINAL LENS (D): 44.79
POWER OF FINAL LENS:

EDGE GRAPHICS GO HERE

Diopters scale: 48.4, 47.9, 47.4, 46.8, 46.2, 45.7, 45.3, 44.8, 44.3, 43.8, 43.3, 42.9, 42.5, 42.0

Angles: TMP, 0, 15, 30, 45, 60, 75, 90, 105, 120, 135, 150, 165, 180, NAS

MATERIAL: pmma    TINT: BLUE    ORDER NO: 0001000000016

| BCOR | BCOD | FCOR | FCOR | FLANGE | OAD | CT | JT | ET | BUP |
|---|---|---|---|---|---|---|---|---|---|
| 7.530 | 6.860 | 8.848 | 8.348 | 6.726 | 8.860 | 0.249 | 0.379 | 0.100 | -5.002 |

LENS_CURVES
BACK PERIPH :   RADIUS : DIAMTR   RADIUS : DIAMTR   RADIUS : DIAMTR   RADIUS : DIAMTR
                9.000 : 7.500  /  10.500 : 8.100  /  12.000 : 8.800  /    :

BACK EDGE   :    :       :       :
FRONT EDGE  :    8.348 : 8.000  /  6.726 : 8.860  /

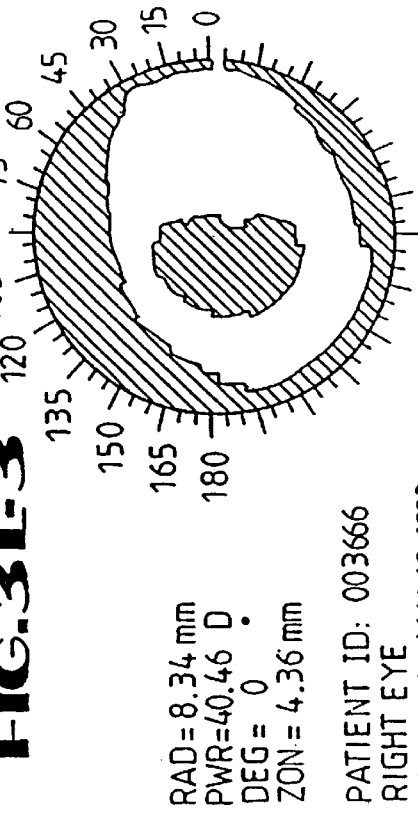
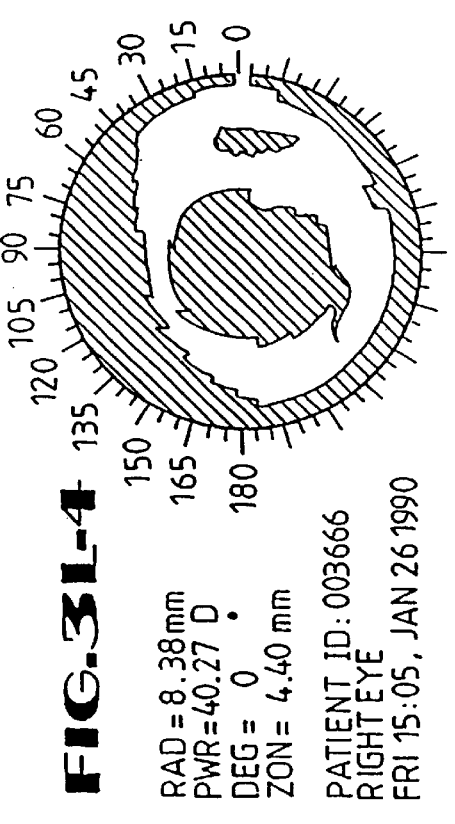
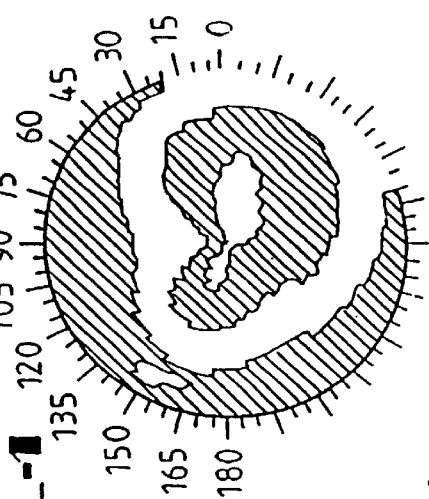
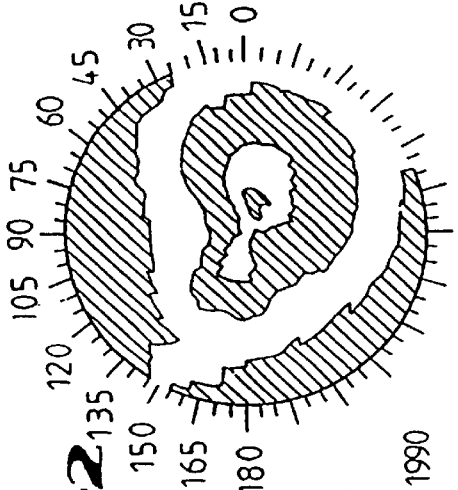
FIG. 3L-1
FIG. 3L-2
FIG. 3L-3
FIG. 3L-4

FIG.3M-1

LEFT EYE

STEEPEST AXIS (AT 91 DEGREES)

PATIENT ID: 003666
FRI 19:07, JAN 19 1990

| INF QUAD | ZONE | RADIUS(mm) | DIOPTERS | SUP QUAD | ZONE | RADIUS(mm) | DIOPTERS |
|---|---|---|---|---|---|---|---|
| #01 | 1.08 | 8.59 | 39.28 | #01 | 1.10 | 8.53 | 39.56 |
| #02 | 1.48 | 8.63 | 39.10 | #02 | 1.45 | 8.47 | 39.84 |
| #03 | 1.83 | 8.67 | 38.92 | #03 | 1.82 | 8.39 | 40.22 |
| #04 | 2.24 | 8.66 | 38.97 | #04 | 2.21 | 8.35 | 40.41 |
| #05 | 2.65 | 8.64 | 39.06 | #05 | 2.58 | 8.28 | 40.76 |
| #06 | 3.07 | 8.62 | 39.15 | #06 | 2.97 | 8.20 | 41.15 |
| #07 | 3.52 | 8.58 | 39.33 | #07 | 3.37 | 8.12 | 41.56 |
| #08 | 3.93 | 8.54 | 39.51 | #08 | 3.80 | 8.05 | 41.92 |
| #09 | 4.33 | 8.48 | 39.79 | #09 | 4.20 | 7.99 | 42.24 |
| #10 | 4.75 | 8.41 | 40.13 | #10 | 4.63 | 7.94 | 42.50 |
| #11 | 5.17 | 8.33 | 40.51 | #11 | 5.03 | 7.89 | 42.77 |
| #12 | 5.55 | 8.24 | 40.95 | #12 | 5.44 | 7.85 | 42.99 |
| #13 | 5.89 | 8.15 | 41.41 | #13 | 5.84 | 7.80 | 43.26 |
| #14 | 6.29 | 8.03 | 42.02 | #14 | 6.27 | 7.73 | 43.66 |
| #15 | 6.65 | 7.91 | 42.66 | #15 | 6.64 | 7.66 | 44.06 |
| #16 | 6.82 | 7.81 | 43.21 | #16 | 6.88 | 7.60 | 44.40 |

FIG. 3M-2

LEFT EYE

FLATTEST AXIS (AT 176 DEGREES)

| TMP QUAD | ZONE | RADIUS(mm) | DIOPTERS | NAS QUAD | ZONE | RADIUS(mm) | DIOPTERS |
|---|---|---|---|---|---|---|---|
| #01 | 1.14 | 8.93 | 37.79 | #01 | 1.17 | 8.89 | 37.96 |
| #02 | 1.54 | 8.94 | 37.75 | #02 | 1.58 | 8.88 | 38.00 |
| #03 | 1.99 | 8.93 | 37.79 | #03 | 2.00 | 8.85 | 38.13 |
| #04 | 2.38 | 8.93 | 37.79 | #04 | 2.43 | 8.79 | 38.39 |
| #05 | 2.82 | 8.91 | 37.87 | #05 | 2.83 | 8.73 | 38.65 |
| #06 | 3.27 | 8.90 | 37.92 | #06 | 3.22 | 8.64 | 39.06 |
| #07 | 3.70 | 8.87 | 38.04 | #07 | 3.65 | 8.54 | 39.51 |
| #08 | 4.18 | 8.83 | 38.22 | #08 | 4.05 | 8.43 | 40.03 |
| #09 | 4.62 | 8.78 | 38.43 | #09 | 4.48 | 8.32 | 40.56 |
| #10 | 5.04 | 8.72 | 38.70 | #10 | 4.88 | 8.22 | 41.05 |
| #11 | 5.48 | 8.64 | 39.06 | #11 | 5.29 | 8.13 | 41.51 |
| #12 | 5.92 | 8.56 | 39.42 | #12 | 5.70 | 8.06 | 41.87 |
| #13 | 6.33 | 8.50 | 39.70 | #13 | 6.10 | 8.02 | 42.08 |
| #14 | 6.80 | 8.41 | 40.13 | #14 | 6.55 | 7.97 | 42.34 |
| #15 | 7.21 | 8.34 | 40.46 | #15 | 7.06 | 7.95 | 42.45 |
| #16 | 7.59 | 8.28 | 40.76 | #16 | 7.41 | 7.94 | 42.50 |

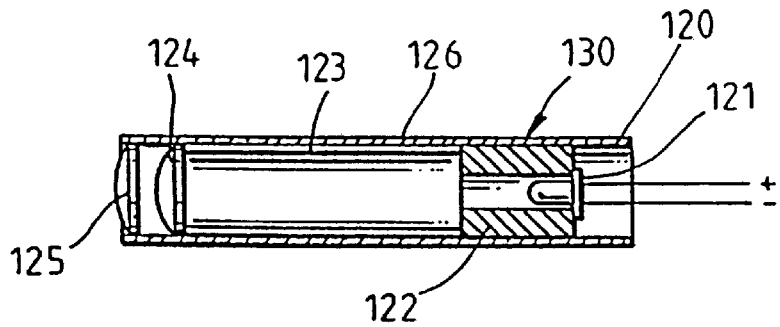
FIG. 5A
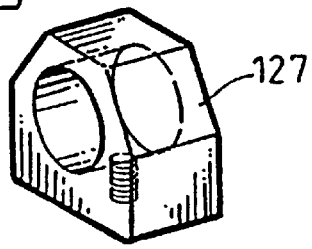
FIG. 5B
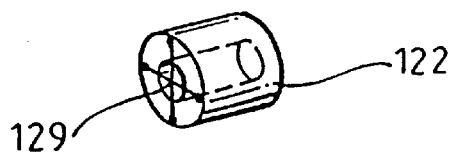
FIG. 5C
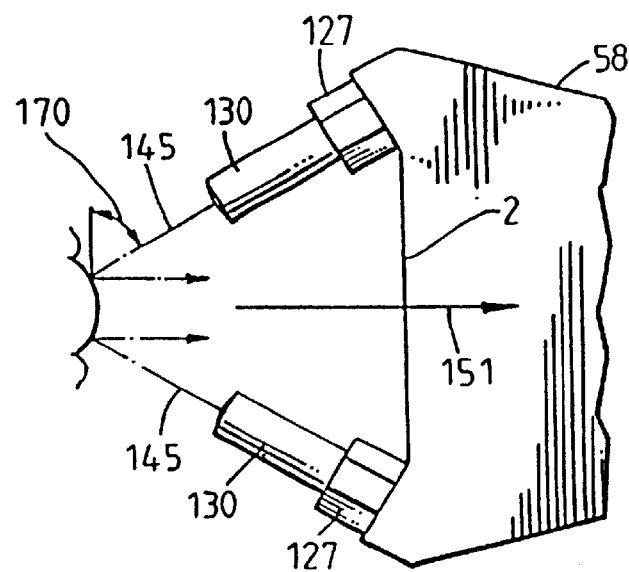
FIG. 6A
  
FIG. 6B  FIG. 6C  FIG. 6D

FIG.8H-1
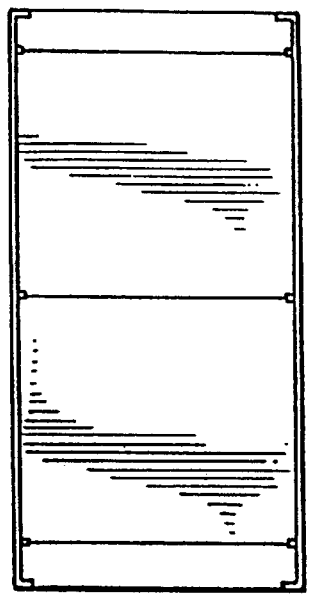
FIG.8H-3
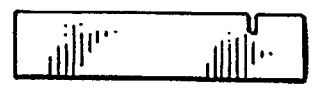
FIG.8H-4
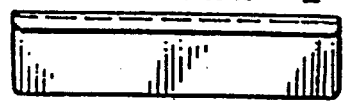
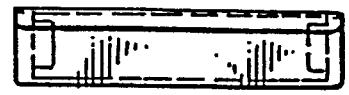
FIG.8H-5
FIG.8H-2
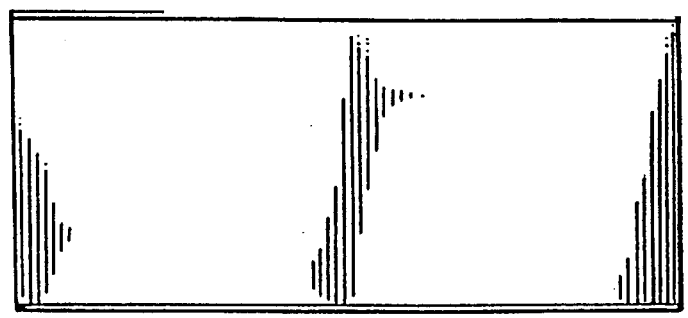
FIG.8H-9 FIG.8H-7
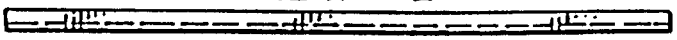
FIG.8H-10 FIG.8H-8
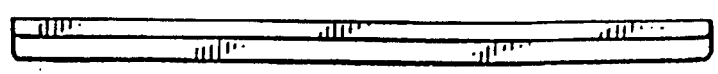

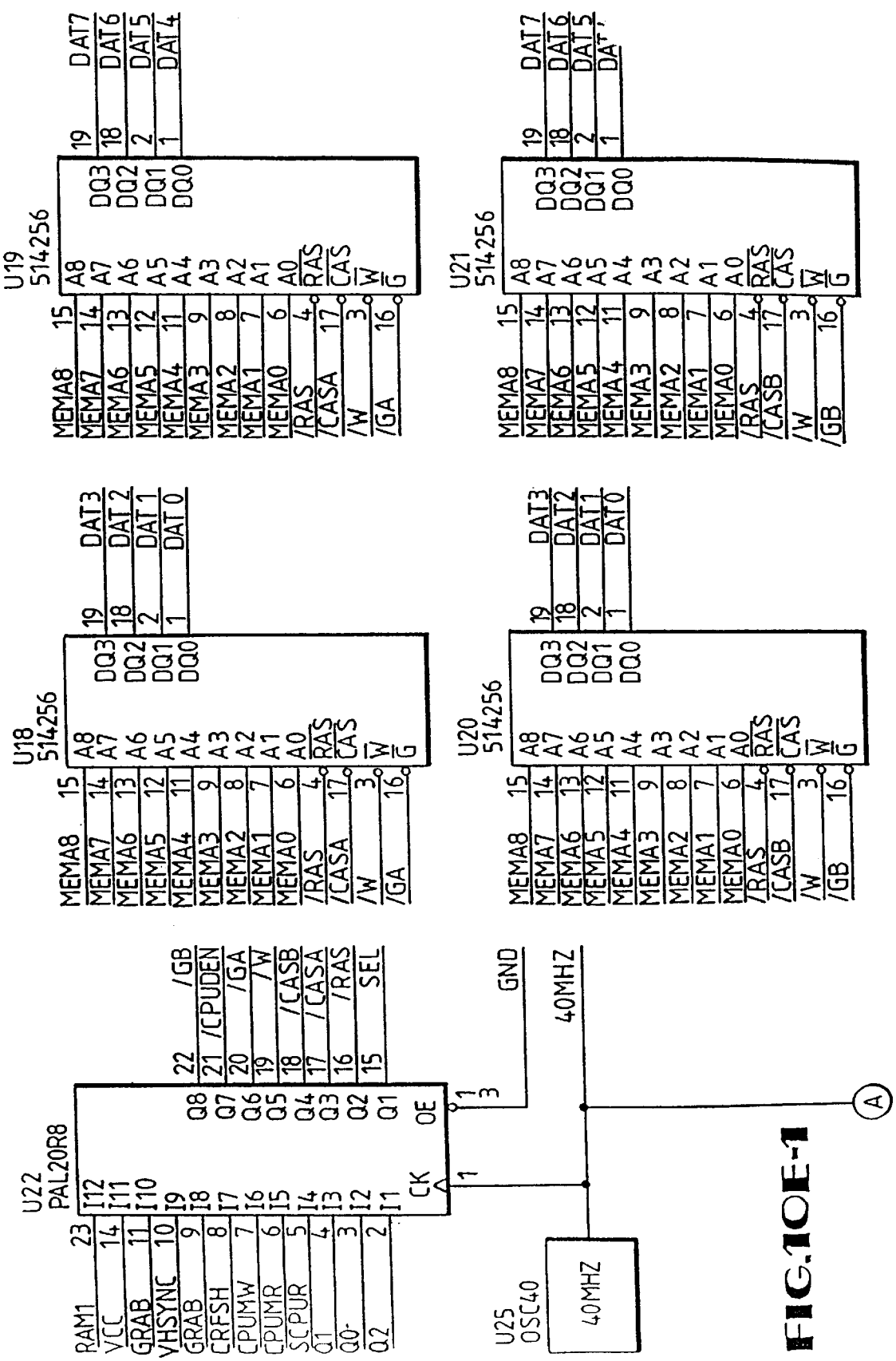

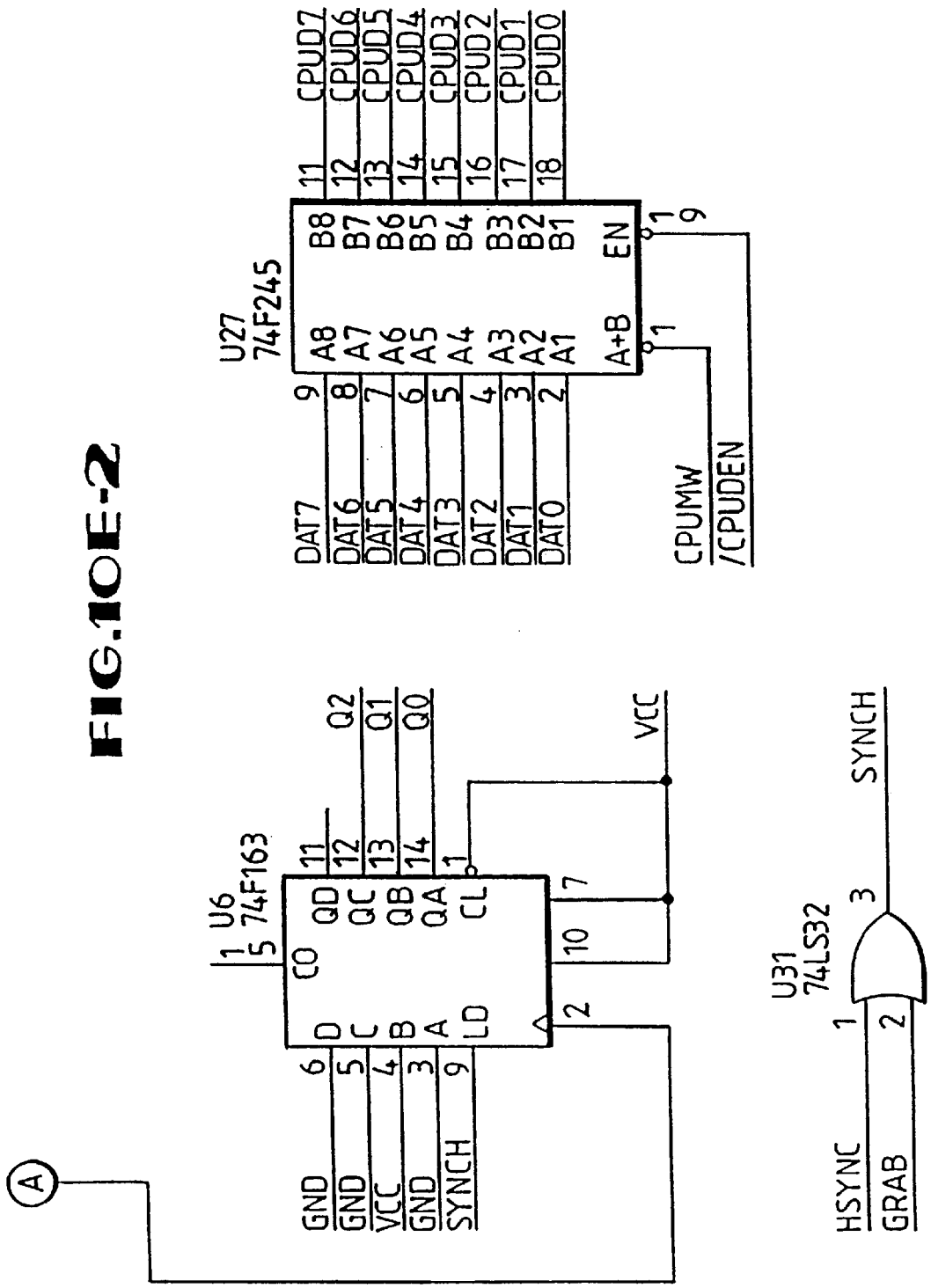

CHIP            FRAMETIME            PAL20R8

;PINS   1     2     3     4     5      6      7      8      9     10     11    12
        CLK   Q2    Q0    Q1    SCPUR  MEMR   MEMW   CRFSH  GRB   HSYNC  NC    BNC

;PINS   13    14    15    16    17     18     19     20     21      22    23    24
        TRICE NC    SEL   RAS   CASA   CASB   W      GA     CPUDEN  GB    RAM   VCC

EQUATIONS

/RAS  := /GRB * /HSYNC * Q0 * Q1
       + /GRB * /HSYNC * /RAS             ; GRAB AND
       + GRB * /CRFSH * /CASA             ; CRT DISP
       + GRB * /CRFSH * /CASB             ; CPU ACCESS
       + GRB * Q0 * Q1 * /SCPUR           ; AND
       + GRB * /RAS * /SCPUR              ; REFRESH

/CASA := /GRB * Q0 * /Q1 * /HSYNC * /RAM         ; GRAB AND CRT DISP
       + GRB * Q0 * /Q1 * /SCPUR * /RAS * /RAM   ; CPU ACCESS
       + GRB * /CASA * /SCPUR * /RAM             ; CPU ACCESS
       + GRB * /CRFSH * Q0 * /Q1 * /RAM          ; REFRESH
       + GRB * /CRFSH * /CASA * /RAM             ; REFRESH

/CASB := /GRB * Q0 * /Q1 * /HSYNC * RAM
       + GRB * Q0 * /Q1 * /SCPUR * /RAS * RAM
       + GRB * /CASB * /SCPUR * RAM
       + GRB * /CRFSH * Q0 * /Q1 * RAM
       + GRB * /CRFSH * /CASB * RAM

/W    := /GRB
       + GRB * /SCPUR * /MEMW * Q0 * Q1
       + GRB * /SCPUR * /MEMW * /W

/GA   := GRB * /SCPUR * /MEMR * Q0 * Q1 * /RAM
       + GRB * /SCPUR * /MEMR * /GA * /RAM

/GB   := GRB * /SCPUR * /MEMR * Q0 * Q1 * RAM
       + GRB * /SCPUR * /MEMR * /GB * RAM

/CPUDEN := Q0 * Q1 * GRB * /SCPUR * /MEMW
        + /CPUDEN * GRB * /SCPUR * /MEMW
        + Q0 * Q1 * GRB * /SCPUR * /MEMR
        + /CPUDEN * GRB * /SCPUR * /MEMR

/SEL  := /GRB * /HSYNC * Q0 * Q1
       + /GRB * /SEL * /HSYNC
       + GRB * /Q1

FIG.10H

```
CHIP            SWITCHDECODE        PAL20L8
;
; PINS  1    2    3    4    5    6    7    8    9    10   11   12
       A0   A1   A2   A3   A4   A5   A6   A7   A8   A9   IOR  GND
; PINS  13   14   15   16   17   18   19   20   21   22   23   24
       IOW  AEN  NC   YOFF BSY  SWO  YON  RBF  RTD  IODEC SWI  YCC
;
EQUATIONS
SWO.TRST  = YCC
RTD.TRST  = YCC
RBF.TRST  = YCC
BSY.TRST  = /RBF
YON.TRST  = YCC
YOFF.TRST = YCC
IODEC.TRST = YCC

/RTD = /AEN*/IOW*A9*A6*/A7*/A6*/A5*/A4*/A3*/A2*/A1*A0

/YON = SWC

/SWO = /RTD
     + SWI * /SWO * YOFF

/RBF = /AEN*/IOR*A9*A8*/A7*/A6*/A5*/A4*/A3*/A2*A1*A0

/BSY = SWO

/IODEC = /AEN*/IOW*A9*A8*/A7*/A6*/A5*/A4*/A3*A2*A1*A0

/YOFF = /AEN*/IOW*A9*A8*/A7*/A6*/A5*/A4*/A3*A2*/A1*A0

SIMULATION
TRADE_ON SWC RTD YON YOFF
SETF /AEN /IOW A9 A8 A7 A6 A5 A4 A3 A2 A1 A0
SETF /A7 /A6 /A5 /A4 /A3 /A2 /A1
SETF A7 A6 A5 A4 A3 A2 A1
SETF /A7 /A6 /A5 /A4 /A3 /A1
SETF A7 A6 A5 A4 A3 A1
TRADE_OFF
```

FIG.101

CHIP          ADDRESSDECODE         PAL16L8

;PINS   1    2    3    4    5    6    7    8    9    10
        A9   A10  A11  A12  A13  A14  A15  A16  A17  GND
;PINS   11   12   13   14   15   16   17   18   19   20
        MEMR VALADDR ADD2 CAS A18  A19  AEN  MEMW BRD2 VCC

EQUATIONS
/VALADDR.TRST = VCC
/ADD2.TRST = VCC
/BRD2.TRST = VCC

/VALADDR = /AEN*/MEMW*A19*A18*/A17*A16*/A15*A14*/A13*/A12*/A11*/A10*/A9 ;D
         + /AEN*/MEMR*A19*A18*/A17*A16*/A15*A14*/A13*/A12*/A11*/A10*/A9

/ADD2 = /AEN*/MEMW*A19*A18*/A17*A16*/A15*A14*A13*/A12*/A11*/A10*/A9 ;D6000
      + /AEN*/MEMR*A19*A18*/A17*A16*/A15*A14*A13*/A12*/A11*/A10*/A9

/BRD2 = /AEN*/MEMR*A19*A18*/A17*A16*/A15*A14*/A13*/A12*/A11*/A10*/A9*CAS

SIMULATION

FIG.103

CHIP          ( ER                    PAL20X10

;PINS  1    2    3    4    5    6    7    8    9    10   11   12
       CLK  D1   D2   D3   D4   D5   D6   D7   D8   D9   /LD  GND
;PINS  13   14   15   16   17   18   19   20   21   22   23   24
       /OE  Q0   Q1   Q2   Q3   Q4   Q5   Q6   Q7   Q8   Q9   VCC

EQUATIONS

SIMULATION

OPTICAL PATH LAYOUT & DESIGN

OLD STYLE

USING 75mm FL. X 25mm ∅ LENS
EDMUND P.N. - B.32, 325

CALCULATIONS:
$$\frac{1}{F} = \frac{1}{S} + \frac{1}{S'}$$
$$M = \frac{S}{S'}$$

F = FOCAL LENGTH
S = IMAGE DIST.
S' = OBJECT DIST.
M = MAGNIFICATION

CCD 1/2" SIZE = 6.4mm X 4.8mm$^2$
IMAGE NEEDED = 11mm HORZ.
$$M = \frac{6.4}{11} = 0.58$$

F = 75mm
M = 0.58
S = 4.67 INCHES
S' = 8.04 INCHES

CONVERSION =
$$\frac{1}{F} = \frac{1}{S} + \frac{1}{S'}$$
$$M = \frac{S}{S'} \Rightarrow M \times S' = S$$
$$\frac{1}{F} = \frac{1}{MS'} + \frac{1}{S'}$$
$$\frac{1}{F} = \frac{1+M}{MS'}$$
$$F = \frac{MS'}{1+M}$$
$$F = \frac{.58 (S')}{1.58}$$

$$\frac{1}{75mm} = \frac{1}{204.3} + \frac{1}{S}$$

S = 118.5mm
 = 4.67 INCHES

75mm (1.58) = .58 (S')
118.5 = .58 (S')
204.3 = S' = 8.04 INCHES

FIG.11A

OPTICAL PATH

NEW STYLE

USING: 60mm FL X 25mm TECH SPEC COATED ACHROMATIC LENSES EDMUND P.N. - B 32, 724

M = 0.58
F = 60mm $$F = \frac{MS'}{M+1}$$

$$60mm = \frac{.58\,(S')}{1.58}$$

S' = 163.45mm = 6.43 INCHES $$\frac{1}{60} = \frac{1}{163.45} + \frac{1}{S}$$

S = 94.8mm = 3.73 INCHES 10.16 TOTAL LENGTH

TUBE LENGTH 7.325

| SYSTEM MAIN MENU |
| --- |
| 1. ACQUIRE NEW DATA |
| 2. REVIEW/COMPARE OLD DATA |
| 3. CALIBRATE INSTRUMENT |
| 4. PATIENT DATA UTILITIES |
| 5. EDIT PROGRAM PROFILE |

1B

1B

| ACQUIRE DATA MENU |
| --- |
| 1. ACQUIRE RIGHT EYE (O.D.) |
| 2. ACQUIRE LEFT EYE (O.S.) |

1C

1C

| ACQUIRE DATA MENU |
| --- |
| 1. ACQUIRE RIGHT EYE (O.D.) |
| 2. ACQUIRE LEFT EYE (O.S.) |
| |
| SYSTEM READY: CENTER, FOCUS, AND PRESS CAPTURE SWITCH (ESC ABORTS) |

NOTE:
WHEN #1 WAS SELECTED IN 1B, WE ENTERED ROUTINE GET DAT, GET DAT( ) IS FLOWCHARTED IN FIG. 12B AND IS THE ENTRANCE TO THE IMAGE PROCESSING SOFTWARE.

FIG. 12A

FIG. 12B — ROUTINE GET DAT( )

- CALL INIT-HRT( ) <SEE FIG. 12C>

- INIT RING COURT ARRAY

- CALL HANDFOCUS <SEE FIG. 12D>

- IF NOT ABORTED BY USER OR ERROR, CALL PROCESS-IMAGE( ) <SEE FIG. 12F>

- IF PROCESS-IMAGE( ) IS NOT ABORTED, CALL SHOW-CON-DAT( ) <SEE FIG. 12E>

- IF, VIA SHOW-CON-DAT( ), USERS "ACCEPTS" PROCESSED IMAGE, CALL CAL-FILTER /*RING RECONSTRUCTION*/ AND SHOW-CON-DAT( ) ON THE "FILTERED" RINGS...

- IF THEY ACCEPT FILTERED RINGS, CALL CALIBRATION INTERPOLATION ROUTINES: ALL-CURV-DIOP( ) <SEE FIG. 12I>

FIG. 12C — INIT-HRT( )

- CALL FBINIT( )

FBINIT( )

- INITIALIZE POINTERS FOR FG CARD MANIPULATION
- CALL FIND-FB( )
- INIT CENTER FINDING WINDOW VARIABLES

FIND-FB( )

PURPOSE: TRY TO DECIDE IF THE FG CARD IS PRESENT AND FUNCTIONING

ALGORITHM: WRITE SOME DATA TO A ROW OF THE FG CARD
CHANGE ROWS
WRITE SOME BLANK DATA TO FG CURRENT ROW
CHANGE ROW BACK TO ORIGINAL
VERIFY THAT DATA WRITTEN IS STILL THERE

HANDFOCUS( )

- CALL LIVE/* SIGNAL FG TO CONTINUOUSLY GRAB FRAMES...*/
- SIGNAL FG TO START SAMPLING AND TO SWITCH CAMERA VIDEO SIGNAL DIRECTLY TO MULTISYNC/VGA MONITOR
- PAUSE A FEW MILLISECONDS TO LET SYSTEM SETTLE
- WAIT/LOOK-FOR USER TO PRESS CAPTURE SWITCH OR ENTER
- IF USER ABORTS OR SIGNALS TO CAPTURE, REGARDLESS, FREEZE A FRAME (TAKE A SHOT) FROM THE CAMERA
- SIGNAL FG TO STOP DISPLAYING CAMERA SIGNAL DIRECTLY ON MULTISYNC/VGA DISPLAY

NOTE:

AT THIS POINT, WE HAVE AN IMAGE THAT WE MAY OR MAY NOT WANT TO PROCESS...THE IMAGE IS STORED IN THE FG CARD'S MEMORY (256 KB)

FIG. 12D

SHOW-CON-DAT( )

PURPOSE : EXPAND VIDEO IMAGE TO FILL ENTIRE VGA SCREEN, THROUGH SUPER-IMPOSE FOUND RING POINTS ON TOP OF EXPANDED IMAGE...ASK USER IF THEY WANT TO USE THIS SHOT (THIS IS ONE OF THE WAYS WE INDEMNIFY OURSELVES...IT IS THEIR JOB TO DECIDE IF THE SHOT IS VALID!)

ALGORITHM : WE HAVE 512 PIXEL COLUMNS, WE NEED 40 TO FILL SCREEN...SO TAKE EVERY 4TH AND 5TH PIXEL, AVERAGE THEM, AND INSERT THE RESULT IN BETWEEN THE TWO...ESSENTIALLY, THIS MAKES 4 PIXELS BECOME 5, QUICKLY AND IN A REASONABLE WAY...

FIG. 12E

PROCESS-IMAGE ( )

PURPOSE: DRIVER FUNCTION FOR IMAGE PROCESSING ALGORITHM...AMONG OTHER THINGS, THIS FUNCTION WILL ALLOW YOU TO LOAD AN EYE IMAGE OFF DISK AND TREAT IT LIKE IT WAS JUST "CAPTURED"

ALGORITHM OVERVIEW: PREPROCESS ( )   <SEE FIG. 12G>
(NOTE:   NOW HAVE CENTER COORDINATES...)
FINDRINGS   <SEE FIG. 12H>

FIG. 12F

PREPROCESS ( )

PURPOSE: PREPARE IMAGE FOR RING FINDING...THIS CODE HAS MANY THINGS IT CAN DO THAT WE DO NOT USE - I WILL ONLY DESCRIBE THOSE I USE IN "PRODUCTION"

TRY TO FIND CENTER OF IMAGE:

- MAKE A COPY OF A BOX FROM THE CENTER OF THE IMAGE

- SMOOTH OVER BOX AREA TWICE (SMOOTHING IS A STANDARD IMAGE PROCESSING TECHNIQUE THAT BLEEDS COLORS TOGETHER)...CUTS DOWN ON CAMERA SIGNAL NOISE (ALLOWS CHEAPER CAMERA)

- DO SOBEL EDGE ANALYSIS ON BOX AREA (AGAIN, SOBEL ANALYSIS IS A STANDARD IMAGE PROCESSING TECHNIQUE WHICH ENHANCES EDGES WHILE LEAVING OTHER FEATURES "UNTOUCHED")

- RESTORE BOX AREA WITH THE ORIGINAL IMAGE

NOTE: SEE FIG. 12J

FIG. 12G

FINDCENTER ( )

PURPOSE: FIND THE CENTER OF THE BOX AREA, WHICH WE ASSUME WILL CONTAIN THE CENTER CIRCLE FROM THE PLACIDO PATTERN

ALGORITHM: THE PREPROCESSING AND SOBEL ANALYSIS HAVE LEFT US WITH A DARK CIRCLE (THE CENTER HOLE) SURROUNDED BY RINGS...THE CENTER HOLE SHOULD BE CONSISTENTLY THE LARGEST BLACK "SPLOTCH" ON THE BOX, SO WE LOOK FOR THE HOLE BY TAKING SLICES OUT OF THE BOX AND FINDING THE ONES WITH THE LONGEST BLACK "STREAK" IN THEM...BY PROCESS OF TRIANGULATION, I CAN FIND THE CENTER OF THIS DARK HOLE...THE TRIANGULATION ALLOWS ME TO APPROXIMATE THE CENTER TO A TENTH (1/10) OF A PIXEL, CONSISTENTLY...THE 1/10 OF A PIXEL RESOLUTION IS <u>CRITICAL!</u> ESSENTIALLY, BY APPROXIMATING TO A 1/10 OF A PIXEL, WE HAVE THE EQUIVALENT OF A CCD CAMERA WITH 10 TIMES THE RESOLUTION (NO SUCH CAMERA EXISTS!)

NOTE: SEE FIG: 12J

FIG. 12H

FINDRINGS

PURPOSE: FIND THE RINGS

KNOWLEDGE: KNOW THE CENTER COORDS

ALGORITHM: FROM THE CENTER, LOOK OUT RADIALLY AND DETECT TRANSITIONS BETWEEN THE LIGHT AND DARK RINGS...THE TRANSITIONS ARE IN FACT THE RINGS; WE RECORD THE COORDS AND THEN FIND THE DISTANCE BETWEEN THESE AND THE CENTER - YIELDING A RING RADIUS AT THAT/THOSE POINT(S). I TAKE 360 PROFILES OUT FROM THE CENTER TO THE EDGE OF THE IMAGE AND FIND AND RECORD THE TRANSITION POINTS ON EACH. NOTE THAT ALL THE MATH <EVEN SIN( ) AND COS( )> IS DONE WITH INTEGER ARITHMETIC, GREATLY ENHANCING SPEED. THE TRANSITIONS ARE FOUND USING A TECHNIQUE WHICH MODELS DERIVATIVES (IN THE CALCULUS).

NOTE: EACH PROFILE/MERIDIAN (360 OF THEM) CAN BE PROCESSED *INDEPENDENTLY* AND IN PARALLEL, MAKING THIS ALGORITHM IDEAL FOR PARALLEL PROCESSING. THE SOBEL ANALYSIS CAN ALSO BE DONE IN PARALLEL.

FIG. 12I

ALL-CURY-DIOP ( )

CALLS COUP-CALS( ) ONCE FOR EACH OF THE 360 DEGREES

COUP-CALS( )

EACH CALL TAKES 1 DEGREE OF THE P-RING ARRAY (THE RING RADII) AND COMPARES IT TO THE CORRESPONDING DEGREE OF THE STORED CAL-BALLS RING RADII, FIND WHERE EACH RADIUS LIES (BETWEEN) AND INTERPOLATING A DIOPTER/MILLIMETER-CURVATURE-OF-RADIUS VALUE BASED ON THE KNOWN VALUES OF EACH OF THE CAL-BALLS. INTERPOLATION OUTSIDE THE CAL RANGE IS DONE LINEARLY BASED ON THE TOTAL RANGE OF THE CAL-BALL SET (INCREASED ACCURACY OVER PURE MATHEMATICAL MODELING, FOR INSTANCE.

A SIDE EFFECT OF DOING THIS DEGREE BY DEGREE IS THAT IMPERFECTIONS IN THE PLACIDO "WASH-OUT" BECAUSE SUCH IS IN THE CAL DATE, TOO. THE CAL DATA (IN FILE CAL.DAT) IS JUST THE STORED P-RING STRUCTURES FOR ALL THE CAL-BALLS. ALL RING RADII ARE SCALED BY 10 (i.e. A RADIUS OF 230 IS STORED AS 2300) TO INCREASE PRECISION AND KEEP FROM LOSING INFORMATION DURING ARITHMETIC OPERATIONS (AND HENCE, NO FLOATING POINT MATH IS NECESSARY).

METHOD OF CORNEAL ANALYSIS USING A CHECKERED PLACIDO APPARATUS

This is a continuation of U.S. application Ser. No. 09/102,839 filed Jun. 23, 1998, entitled "A Method of Corneal Analysis Using a Checkered Placido Apparatus", now U.S. Pat. No. 6,213,605, which in turn is a continuation in part of application Ser. No. 07/891,961, filed Jun. 2, 1992 now abandoned, the entirety of all of which are expressly incorporated herein by reference, including the Microfiche Appendix from U.S. Pat. No. 6,213,605.

CROSS REFERENCE TO RELATED PATENT APPLICATIONS

This patent application is related to the patent application for a "VIDEO TO PRINTER INTERFACE METHOD AND APPARATUS" by Edwin J. Sarver, Henry M. D'Souza, Steven Woo filed concurrently on Apr. 10, 1992. This patent application is related to the design patent application for "DESIGN FOR AN ABSOLUTE DIOPTRIC SCALE REPRESENTATION" filed concurrently with this application on Apr. 10, 1992 by Edwin Jay Sarver, Ph.D. and assigned to EyeSys Laboratories, Inc. This patent application is also related to U.S. Ser. No. 07/817,868, "A" Contact Lens Sculpturing Device" by Wakil, D'Souza, Baumgartner, and Carbonari and assigned to EyeSys Laboratories, Inc. (pending divisional application of 607,640 filed Jan. 7, 1992); U.S. applications Ser. No. 07/818,659, "A Method of Using A Placido" by Wakil, D'Souza, Baumgartner, and Carbonari and assigned to EyeSys Laboratories, Inc. (pending divisional application of 607,640 filed Jan. 7, 1992); and U.S. application Ser. No. 07/819,364, and "A" Placido Apparatus" by Wakil, D'Souza, Baumgartner, and Carbonari and assigned to EyeSys Laboratories, Inc. (pending divisional application of 607,640 filed Jan. 7, 1992).

MICROFICHE APPENDICES FOR COMPUTER PROGRAM SOURCE CODE LISTINGS

This patent specification includes a microfiche appendix. The appendix is a source code listing for the CORNEAL ANALYSIS SYSTEM software, which consists of 11 microfiche, for a total of 997 frames.

BACKGROUND OF THE INVENTION

A number of forms of eye surgery including lamellar corneal surgery, keratomileusis, epikeratophakia, cataract surgery, penetrating keratoplasty, corneal transplantation radial keratotomy as well as laser refractive keratectomy involve a consideration of corneal surface topography. In radial keratotomy, for example, a number of cuts are made into the cornea in order to change its curvature and correct refractive power so that images focus closer to the retina, if not upon it for best visual acuity. It has been reported that after radial keratotomy "about 55 percent of the patients function without glasses and the remaining 45 percent have some degree of improvement." Origination of the technique of radial keratotomy and other techniques in refractive surgery are generally credited to Dr. Svyatasklav Fyodorov of the Soviet Union who is reputed to have performed thousands of such operations.

While ophthalmic surgery is often successfully performed, the results obtained have been subject to variation occasioned by the particular operating "style" of the individual surgeon which dictates the number, location and depth of incision. Elements of subjective judgment are paramount. It would be useful to provide a device that could assist the surgeon in more quantitatively assessing pre-operative and post-operative corneal contours.

The present system relates to improvements in the art of photokeratometry and more particularly to the use of digital image processing techniques to ascertain the radius of curvature, refractive power and contour of the cornea. A keratometer is an instrument for determining the curvature shape of the corneal surface which generally uses a Placido or other illuminated target that is centered around the patient's line of sight. The reflection of a Placido or other illuminated target by the patient's cornea or by the tear film on the anterior surface of the cornea is subsequently analyzed to determine the surface contour of the eye.

The technique in modern form dates from the early thirties when the Zeiss optical company of Germany introduced a "Photo Keratoscope". In general, the art has required the image reflected by the eye to be photographed and the image on the film measured in a second step to derive the quantitative data from which the contour map is generated.

Recent improvements have been in the area of automating this photogrammetric analysis by re-imaging the photograph with a television apparatus and digital signal conversion. After digitization, computer analysis of the resultant information is performed with conventional image analysis algorithms. This type of data analysis is computer intensive and the image formed by the television system contains a large amount of redundant and extraneous information. For adequate resolution the sampling rate must exceed the data frequency by at least three to one, thus generating a huge number of data points for mathematical analysis. Consequently the systems are costly, complex, slow and often lack real resolution in the image analysis. Other means have been used for clinical measurements such as direct casting of the eye surface in plastic or wax and coating the cornea with talcum powder and projecting a grid on this surface for photogrammetric analysis.

The initial development in keratometry came from Gullstrand in 1896. Gullstrand disclosed the foundation for the current technology but his apparatus had no provision to compensate for aberrations in the optical system other than limiting the photographic coverage of the cornea to a 4 mm area. As a result, multiple exposures and calculations were necessary to map the corneal surface. Much of the modern technique was developed by Amsler in 1930 and embodied in his "Photo-Keratoscope" which also required measurement and calculation as a separate step to derive the corneal shape data.

At present, the clinical standard is the Bausch and Lomb Keratometer, which is sold commercially. The Bausch and Lomb Keratometer only measures the average of the corneal radius in two meridians of the central 3 mm "cap" of the cornea. The standard technology does not provide total surface topography of the cornea and thus is inadequate for many diagnostically significant abnormalities, contact lens fitting, or the needs of ophthalmic surgical procedures. In addition, the prior art technique is cumbersome and involves great potential for error.

The standard instrument which is in most common use for central optical zone shape measurement is the Bausch and Lomb Keratometer. Several companies offer similar devices with similar principles of operation. In these devices a single Mire image is projected on a small central portion of the anterior surface of the cornea usually 3 mm in diameter. The user is required to operate several controls to bring the optically split Mire images reflected from the cornea simultaneously into focus and alignment. In addition, the operator manually records the data obtained at two perpendicular axes. Other instruments are also available, such as the Haag-Streit Javal Schiotz device which measures only one axis at a time, but is slightly easier to use and tends to be more accurate in practice than the Bausch and Lomb system. In addition there exists a photographic system made by International Diagnostic Instrument Limited under the trademark "CORNEASCOPE" (and a similar system made by Nidek in Japan), as well as autokeratometers by several manufacturers. The CORNEASCOPE produces instant photographs of the reflection of a Placido disc and requires a second instrument separate from the camera assembly to analyze the data. This system is fairly accurate, but expensive and tedious to use. The autokeratometers all are limited to a single zone of approximately 3 mm diameter and, in cases where the magnitude of the astigmatism is low, are inaccurate in their assessment of axes of astigmatism. Also available are three computer-direct systems which use conventional image analysis algorithms in conjunction with a mini-computer. These are the Corneal Modeling System (CMS) introduced in 1987 by Computed Anatomy, Inc. of New York, N.Y. and the ECT-100, introduced into the market by Visioptic of Houston, Tex. and a system using light emitting diodes disposed in concentric rings built by Zeiss of Germany. The Placido disc-photo technique is superior to the Bausch and Lomb Keratometer because of the much greater amount of corneal surface analyzed from the Placido reflection as opposed to the mires of the Keratometer.

A number of patents have been issued that relate to keratometers. U.S. Pat. No. 3,797,921 proposes the use of a camera to record the Placido reflection from a patients eye. From this photograph, the radius of surface curvature of the cornea is determined at several points and calculated using a complex computer system. The use of a ground glass focusing screen with the small aperture of the optical system and large linear magnification makes use difficult and requires a darkened room for operation.

U.S. Pat. No. 4,440,477 proposes a method and device for measuring the corneal surface, comprising a slit lamp for illuminating the corneal surface, a camera for recording the reflection from the corneal surface, and a processor to calculate the image distance and the radius of curvature of the eye. The operation of the processor is not detailed in U.S. Pat. No. 4,440,477.

A more recent entry into the market is the "Corneal Modeling System" manufactured by Computed Anatomy Incorporated of New York which uses a light cone Placido target in conjunction with a "frame grabber" to digitize and store for conventional image analysis the pictorial data. The Placido is in cylindrical form and illuminated from one end. This cylindrical Placido maintains a small aperture optical system creating a large depth of field of focus for the imaging system and, consequently, requires a sophisticated focus determining apparatus to assure accurate and reproducible image evaluation. This system is said to produce corneal thickness data using a scanning laser, as well as the surface contour but is very expensive and does not lend itself to clinical applications which are increasingly cost driven.

The prior art systems discussed above tend to be both expensive and difficult to use. Many of the prior art devices have a significant potential for error, due to complexity of the calculation, the imaging of the corneal surface and the difficulty in operating these systems.

Since even a normal human cornea will not be perfectly spherical, the illuminated rings will generally be reflected from the corneal surface as a pattern of shapes variously distorted from the circular. The data pertaining to the coordinates of points in the two-dimensional video image is processed to define a three-dimensional corneal surface yielding the equivalent spherical radius of curvature (or dioptric power) for each of the acquired points.

SUMMARY OF THE INVENTION

Accordingly, there is provided herein a new technique for image analysis that provides full topographical mapping of the cornea, with almost instant display of the corneal radius of curvature at enough points to permit accurate assessment of the surface shape. The improved photo keratometer includes a transilluminate target or "Placido", which is reflected by the surface of the eye to be examined. A CCD camera and lens system is mounted behind the Placido so that the optical axis is coincident with the visual axis of the eye being examined and is generally centered in the target member to provide an image of the reflection of the target by the eye. The image information of multiple "rings" on the cornea from the CCD camera is then captured by a frame grabber board and processed by an edge detection algorithm to derive the locus of image brightness discontinuities which are associated with the target reflection from the eye. These image points are, in turn, transferred to storage in the internal memory as digital representations of the x, y locus of the image bright/dark transitions representing the Placido ring edges.

The stored data associated with the CCD image of the target reflection are then treated by an image processing algorithm in a conventional electronic computer to derive the surface contour of the eye and to generate the display of the derived shape information for use by the operator. The Multi-Functional Corneal Analysis System described herein can serve as a sensitive method to determine proper contact lens fit by measuring the shape of both front and back surfaces of the contact lenses and comparing these shape measurements with the shape of the eye to which the said lens is to be applied.

An illustrative system in accordance with the invention the Eyesys Multi-functional Corneal Analysis System which combines the features of an automatic keratometer, photokeratoscope and corneal topography device into a single instrument. Comprehensive keratometric results and quantitative corneal surface measurements provide multifunctional corneal evaluation capabilities. Multiple analysis routines offer information from basic keratometric readings to intermediate zone values and graphics to full surface topography color mapping. An easy to use joy-stick and positioning aid provides precise patient alignment and image focus. User-friendly menus guide users to quick and reproducible exams. An on-line operators manual provides rapid assistance. For most exams, processing time is under 10 seconds for 360 meridians. Corneal information is reported as numerical values with graphic presentations for the 3 mm, 5 mm and 7 mm zones, corneal contour profile graphics of any two meridians and topographical color surface maps according to either dioptric power or millimeter radius of curvature. Up to four surface maps can be displayed for comparative analysis. Patient exams can be archived to hard disc or floppy disc and recalled at any time. Permanent records may be produced via optional Polaroid camera or color graphics printer.

An illustrative system in accordance with the invention utilizes a unique data-acquisition design to perform rapid, cost-effective quantitative photokeratoscopy. The system obtains a complete 360 degree measurement (approximate corneal zone diameter 0.9–9.5 mm) with only a single data-acquisition "shot," eliminating the need for camera rotation. The system has a more precise and user recognizable focusing target and improved optics over other systems known in the art, which further enhances the accuracy and reproducibility of corneal topographic profiles. The interval between electronic data capture and complete display for all meridians is less than 10 seconds. The system is packaged either as a single tabletop unit with a base dimension of roughly 18"×23" which includes an integrated IBM-compatible computer and a photographic port so that standard photokeratoscopic photographs on Polaroid or 35-mm film can easily be obtained or as a modular unit on a mobile pedestal with dimensions of 32"×24" with computer housing separate from photokeratoscope. Video output is available for video image storage if desired. In addition to standard numerical displays, new color graphics for corneal profiles and for isodioptric color-coded contour maps can be selected. The system in accordance with the invention is easy to use and therefore suitable for use in a standard clinical setting. Its data-acquisition design provides rapid data capture and display and offers distinct advantages for clinical and research applications.

BRIEF DESCRIPTION OF THE DRAWINGS

FIGS. 3A-1, 3A-2, and 3B to 3D, 3E-1, 3E-2, 3F-1, 3F-2, 3G-1, 3G-2, 3H, 3I-1 to 3I-3, 3J, 3K, 3L-1 to 3L-4, 3M-1 and 3M-2 show details of the system menus and graphic presentations.

FIG. 4 is a diagram of optical principles.

FIGS. 5A to 5C show details of the construction of the focusing aid.

FIGS. 6A to 6D show operational sketches of the focusing aid.

FIGS. 8A-1, 8A-2, 8B-1 to 8B-3, 8C-1 to 8C-3, 8D, 8E-1 to 8E-3, 8F-1 to 8F-6, 8G-1 to 8G-4, 8H-1 to 8H-10, and 8I-1 to 8I-6 show mechanical drawings of the optical assembly housing.

FIG. 9 is a schematic of the power supply.

FIGS. 10A, 10B-1, 10B-2, 10C, 10D, 10E-1, 10E-2, 10F, 10G-1, 10G-2, and 10H to 10K show block diagrams and schematics and PAL equations for the frame grabber board.

FIGS. 11A and 11B show an exemplary optical path layout and design methodology.

FIGS. 12A to 12K show system menus and high level description of the software.

DESCRIPTION OF ILLUSTRATIVE EMBODIMENTS

I. System Overview

Figure 13:
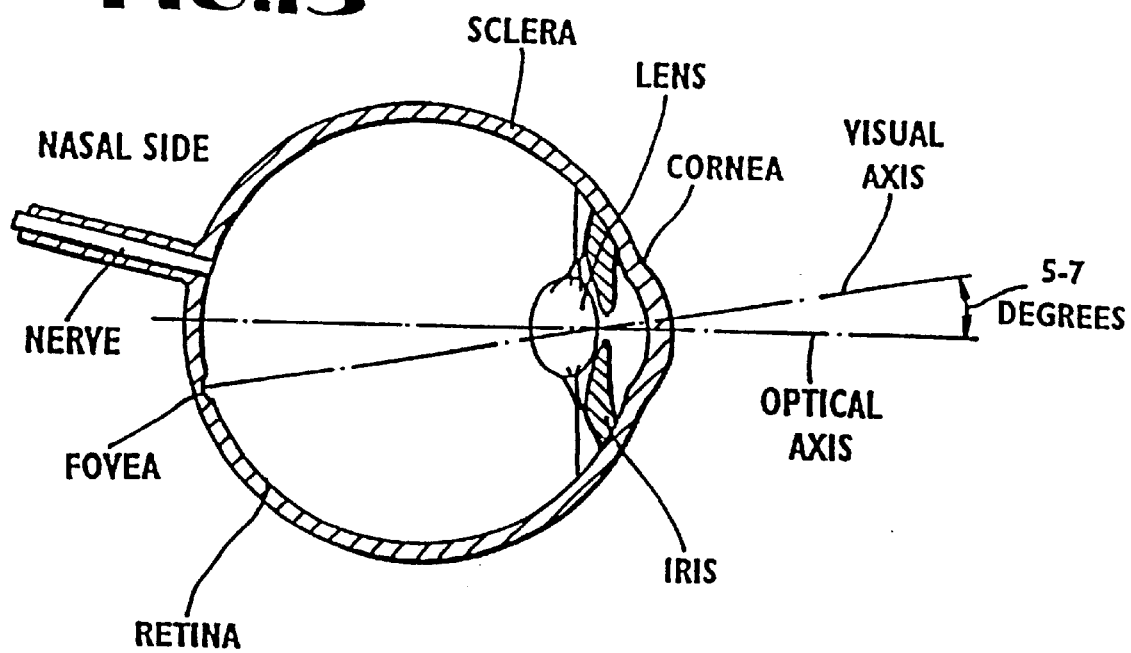
FIG. 13 is a cross section of the eye.
Figure 14:
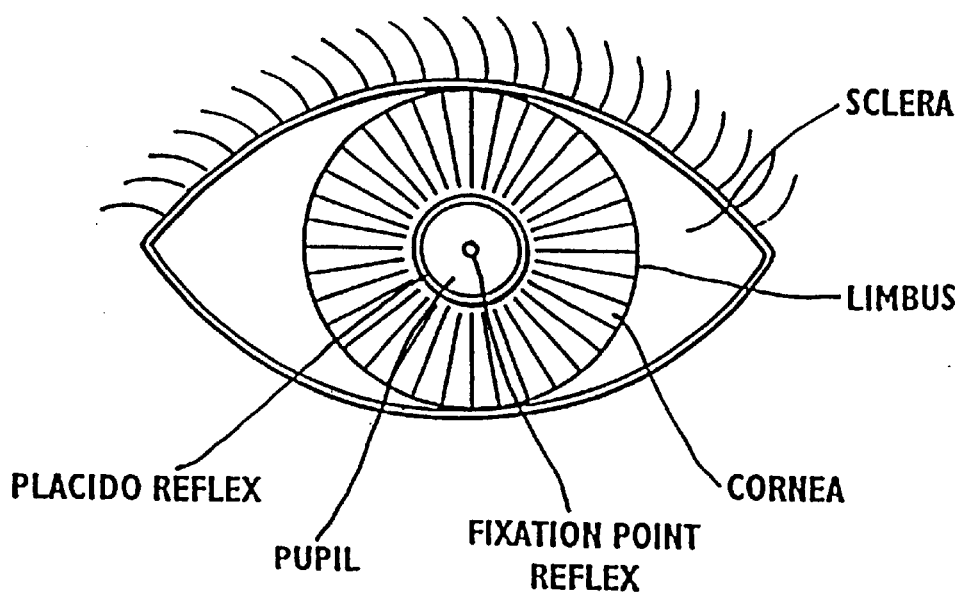
FIG. 14 is a front view of the eye.

FIGS. 13 and 14 illustrate the more important features of the eye as they relate to keratometry. The pupil of the eye is defined by the central area surrounded by the iris. The iris opening size is controlled by the autonomic nerve system in relation to the brightness of illumination as well as other factors and may be as small as one millimeter in diameter in bright light to five millimeters in diameter in dim light. The constriction of the iris in bright light also provides an increase in depth of focus such as is observed in conventional photography. The reflection of the one or more concentric rings of the Placido off of the anterior corneal surface will appear as more or less circular bright rings superimposed on the pupil and iris when viewed by the television camera. The interior of the eye is shown as a horizontal cross-section to show the more important structures. The globe is enclosed in a semi-rigid white membrane called the sclera. The transparent membrane at the front is called the cornea. The cornea is a thin membrane which is supported in shape by the pressure of the fluid behind the membrane and in front of the crystalline lens. The lens is supported by a system of filaments and muscle tissue which cooperate to change its thickness and, in consequence, the focal length of the lens.

The primary focusing power of the optical system of the eye is provided by the light refraction curvature of the cornea and the fluid filling the anterior chamber, while the lens serves to permit the change of plane of focus from near objects to distant scenes. The light entering the eye through the iris opening is brought to focus on the surface of the retina which lines a large portion of the inner globe and contains the photo-receptor cells. These cells are of two general types, rods and cones. The rods predominate in the areas peripheral to central image and are highly sensitive to light but devoid of color sensitivity. The rods provide "scotopic" or night vision. The cones predominate in the central retina and in the "fovea", where critical central vision takes place. The center of vision is located in the fovea which is displaced from the optical axis of the eye by some five to seven degrees. Because the surface of the cornea is not a perfect spherical section the curvature of the surface is asymmetrical around the center of vision or visual axis and must be taken into consideration in keratometry.

As noted in U.S. Pat. Nos. 3,542,458 and 4,440,477 the reflection of an object in a convex mirror will produce an image which is "virtual" (cannot be formed on a screen, but can be viewed directly) erect, and reduced in size by an amount which is a function of the radius of curvature of the mirror. In this system, the tear film and/or the surface of the cornea acts as such a mirror. The formula often used to define the light reflected from a transparent surface is dependent upon the index of refraction of the optical medias-involved.

The commonly used values of the indices of refraction, n, for the three media of transmission in this case, air to tear film and cornea are 1.000 for air, 1.333 for the tear film and 1.3375 for the cornea. There exists approximately a two percent reflection at both of these optical interfaces, i.e. the air/tear film and tear film/anterior corneal surface. The small thickness of the tear film places both reflections in close proximity so that they are indistinguishable from each other for instrumental purposes. As a result these reflections are lumped together for clinical applications. However, the small amount of light in the reflected pattern influences the system design, as discussed below.

The anterior surface of the normal cornea is not quite spherical, as it appears to have been assumed in the construction of many of the prior art devices such as the Bausch and Lomb Keratometer, but is more nearly an ellipsoid. The central two or three millimeters of the normal cornea does conform reasonably to the spherical form so the simplistic model will serve to illustrate the optics of the system for rays at or near the common optical axis.

The user is most often interested in data presentation in terms of diopters of focusing power of the cornea. The radius information can then be converted to this form in the commonly use formula as follows:

$$d=(n-1)/r$$

where the index of refraction of the cornea n is assumed to be 1.3375 and the radius of curvature of the corneal surface r is expressed in meters. It should be noted that there is not an agreement on the actual value of the effective index of refraction of the cornea to be employed in keratometry and that the calculation of corneal curvature in dioptric form also involves optical correction factors to compensate for the effectively negative "lens" formed by the rear surface of the cornea. In practice the value of index of refraction used by several systems for this conversion range from 1.332 (Zeiss) 1.336 (American Optical) to 1.3375 (Haag-Streit and Bausch & Lomb). The "normal" range of curvature in the central zone ranges from 7.2 to 8.3 mm with a mean value of 7.8 mm. Some representative values for the Bausch & Lomb instruments converting the readings into diopters are shown in the following table:

| Dioptral curvature | Surface radius in mm |
|---|---|
| 61.0 | 5.53 |
| 60.0 | 5.63 |
| 47.0 | 7.18 |
| 45.0 | 7.50 |
| 44.0 | 7.67 |
| 42.0 | 8.04 |
| 41.0 | 8.23 |

From the foregoing it follows that the conversion of the data into dioptric form is not difficult and involves the use of a selected constant but that the data so expressed is subject to variable error inherent in the technique. The common keratometer has been used for many years with data in dioptric form, even though the magnitudes are not precisely accurate. The choice of display form either in diopters or millimeter radius of curvature is selectable in this system to permit the user to choose between the more accurate and the more common form. The display of the derived data may be in graph form for ease of assimilation and application by the user.

The data of interest to the user is generated from the pixel radii of each chord of Placido ring reflection in the acquired image in any of the possible directions from center. The millimeter radius of curvature and dioptric curvature of the surface at each of these points is then provided to the user for his evaluation. The keratometer known in the art and in common use measures two perpendicular meridians at each selected angle and produces data in the form of "K1, K2", cylinder and axis. These terms refer to the average dioptric curvature from both sides of visual axis in each of the two meridians which have the greatest and least curvature, assumed to be 90 degrees apart in "regular" astigmatism the magnitude of the difference between the two, and the angle relative to the horizontal of the larger of the two. The terms are commonly used and are recognized by the user as definitive of these descriptive elements as derived by conventional keratometry. The axis can either be measured or assumed to be regular (90 degrees apart), however, in today's applications more comprehensive data is necessary. K values are obtained for a full 360 degrees by a process of repeated measurement and recordation.

To reduce the amount of data required to define the ring image size in radial terms, only those pixel loci which define a change of brightness greater than a threshold value are stored. Each ring reflection produces one data point at each reflection edge. These points can be used to determine the actual locus of the center of the ring reflections. The optical system is preferably provided with an optical fiber which defines the optical center of the system and provides a bright point of light for the patient to fixate upon. The reflection of this small point from the cornea provides a true center from which all measurements are made. Furthermore the numerical scatter of the data points is a function of the focus and overall image quality which permits the evaluation of each measurement for minimum acceptable quality. The decision to reject any measurement which does not fulfill the quality standard is set into the software. This is due to the requirement that the object distance be known and fixed for accurate data analysis. Small errors in focus can degrade the measurement and so an optical system with a small depth of field of focus and a software scatter determination are used to insure accuracy. The central fixation target reflection from the optical fiber is also examined for relationship to the true center of the picture and if the image is decentered in either axis by a predetermined amount the measurement is invalidated. The shadow cast by the nose, brow, lashes, etc. as well as the lid margin which may lie within the camera field will cause some data points to be missing from the theoretical maximum number. The lash shadows will not completely obscure the area to be measured and so some minimum number of valid points may be selected which will permit the areas thus partially masked to be defined with a large degree of confidence. The entire picture is examined for brightness transitions in this manner and the axis determined by mathematical algorithms in the computer. Given that, for example, the image resolution of the system provides a pixel size, Placido image referred, of 0.014 mm (750 pixels=10 mm so one pixel=1/75 mm or 0.0133 mm) then an estimate of the minimum curvature difference and radial interval detectable by the system can be derived.

For best accuracy, each instrument should be calibrated periodically to compensate for minor differences in system magnification and linearity to obtain maximum accuracy of the derived data. For this reason calibration means preferably are provided as a part of the computer software and the user may check the calibration and reset the table values at any time.

Figure 4:
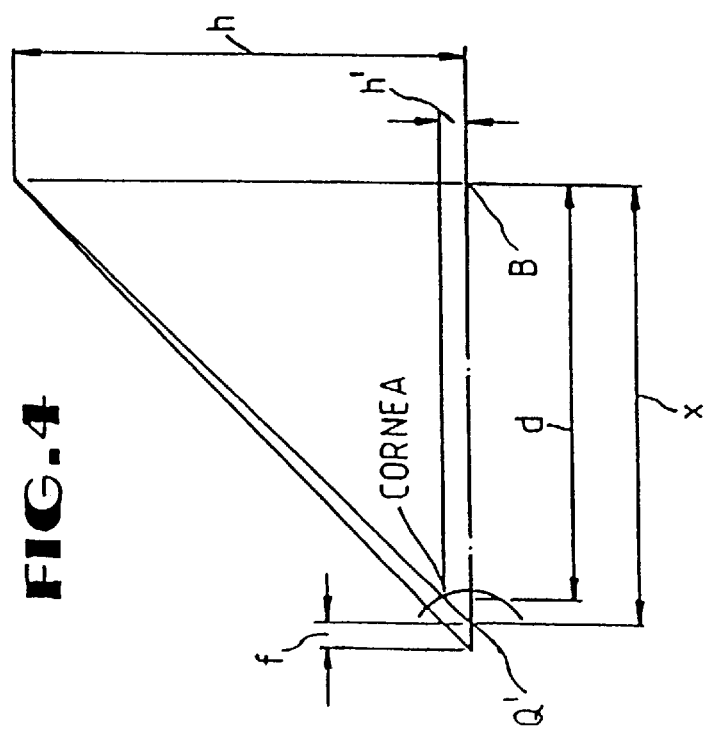

Referring now to FIG. 4, the optical theory diagram shows some of the relationships which are of interest in the present system.

An object (the cornea of the eye to be measured) with a size h is imaged by reflection at plane d with an image size h'. The magnification is derived by the usual formula:

$$m=h'/h$$

The focal length of a convex mirror is negative and equal to one-half of the radius of curvature. The sum of the reciprocals of the object and image distances is equal to the reciprocal of the focal length. These two can then be combined to the form:

$$1/o + 1/i = 1/-f = -2/r$$

or $$i = or/[2(or) - r]$$

It follows that the remainder of the image is formed in a similar fashion and that the same figure applies in any meridian. (These formulae are only true for rays which are very close to the optical axis). From the size of the object, size of the image, the distance and the optical magnification, the radius of curvature can be calculated as follows:

$$R = M(2U/0)I$$

Where:
M is the magnification constant of camera and optics;
U is the distance from object to cornea;
I is the observed size of image; and
0 is the actual size of object.

The objects imaged are the several rings of the target which yield the curvature of the eye at several distances from the center of the cornea. For the $i^{th}$ ring, all the constants are lumped into one, $K_i$, thus:

$$R_i = K_i I_i$$

$R_i$ is the radius of curvature of cornea of the $i^{th}$ ring;
$I_i$ is the observed size of $i^{th}$ ring; and
$K_i$ is the $i^{th}$ ring conversion constants.

Thus, all that is needed for computation of curvatures are the $K_i$ constants. The $K_i$'s can be calculated but it is much easier, and more accurate, to measure them by calibrating the instrument with balls of known, precise diameter $R_o$ and setting all $K_i = 1$. The values of $V_i$ are measured which provides a measurement of $I_i$ since $V_i = 1 \times I_i$. Thus, the constants are determined by:

$$K_i = R_o/V_i$$

Where:
$R_o$ is the known radius of calibration ball; and
$V_i$ is the measured radius of calibration ball with $K_i$ set to 1.

According to conventional techniques a table is constructed to provide a look up system for conversion of measured reflex diameters, representing a range of known surface curvature values. In this manner the necessary degree of precision may be achieved to assure accurate output data accuracy for the intended application. Interpolation between table entries is quite practical and reduces the number of table entries needed to assure accurate measurements.

A more exact surface shape characterization could, in theory, be obtained by the method iterated by Wittenberg and Ludlam in a paper published in the Journal of the Optical Society of America Vol. 56 No. 11, November 1966 but the simpler form provides adequate accuracy for clinical use. The magnification factor and the effective numerical aperture are chosen as a compromise between the most desirable small relative aperture and acceptably small depth of field to facilitate the setup and focusing step. This provides an acceptable error from subject positioning resulting from inability to judge small differences in subject distance due to the depth of focus of the optical system as well as adequate image brightness for noise reduction. In most, if not all cases, the exact surface contour is of less interest to the clinician than the relative contour. For example, in a surgical application, the object is to arrive at a smooth, regular corneal surface, which has a similar shape in two perpendicular axes. That is to say that the corneal astigmatism is minimal. The errors of measurement are least at, or near, the center of the cornea which is the main image forming surface of the eye. Therefore small error accumulation in the periphery of the cornea are tolerable. In surgical procedures where the cornea is cut, suture tension and location can alter the surface shape. The peripheral curvature must be maintained as closely as possible to the same value in all axes if there is to be no induced post-operative astigmatism. The keratometer can provide information for post-operative adjustment of sutures to better achieve this result. The shape derivation for contact lens fitting is also a comparative process in that the lenses may also be measured by the instrument and so small errors from true surface derivation cancel and the resulting data are usable in a clinical context.

Because the eye is centered in the picture by adjustment of the instrument and headrest at the time of setup and because the subject is fixating on a target which is coaxial with the system's optical axis, the center of the reflected image and thus, the cornea can be located exactly by a rather simple software technique. The largest difference between the two central image points from the fixation lamp reflection constitutes a measurement that is equivalent to a diameter of the inner Placido ring reflection (in pixel terms). One-half of that measured value is the center of the figure. The remainder of the analysis is based upon similar technique and is much less software intensive than the classical image analysis algorithms which make more complex decisions about a much larger number of pictorial elements each of which may have one of many numerical values which may represent intensity, saturation and hue. Thus it can be seen that this system substitutes novel means and method for the conventional image analysis technique to permit the construction of a very inexpensive system which can be used to produce clinically useful data when operated by unsophisticated users within the economic constraints imposed by current clinical fee structures.

The computer program controls measurements, data analysis and display format. Each single measurement consists of measuring the edges of the Placido reflection in view. Subsequent to the data gathering step, the curvatures are computed from the available edges. Any values falling outside of a window of selectable size are considered "bad". Then the half chord measurements for each ring from the selected data points are derived. The values of curvature are similarly computed for each ring image on each side of center at enough angles to permit accurate assessment of major and minor axis angles.

The formula used for computing the curvatures is:

$$R_i = K_i R_i$$

Where:
$R_i$ is the radius of corneal surface curvature of $i^{th}$ ring;
$K_i$ is the lumped constant of $i^{th}$ ring; and
$R_i$ is the measured radius of $i^{th}$ ring.
(The lumped constant depends on magnification, ring size, local rate of curvature etc.) The constants $K_i$ are determined by calibrating the instrument by measuring objects of known radius. These data are stored on a disk, in an EPROM (Erasable Programmable Read Only Memory). Eor some similar means for use by the main program. The provision of a variable focal length camera lens would permit adjustment to compensate the magnification errors which will result from the tolerance of focal length of commercial lenses if desired but the calibration table method is the preferred embodiment.

II. Processing Circuitry And Operation

Figures 3B, 3C:
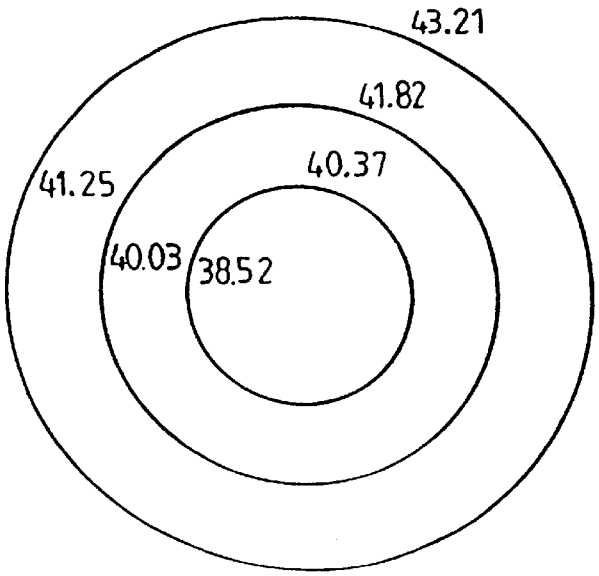
Figures 2, 3G:
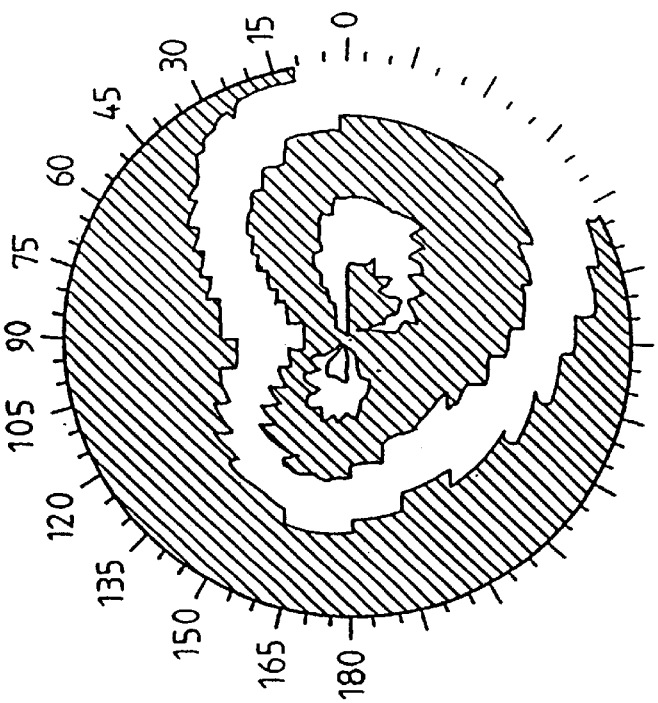
Figures 1, 3G:
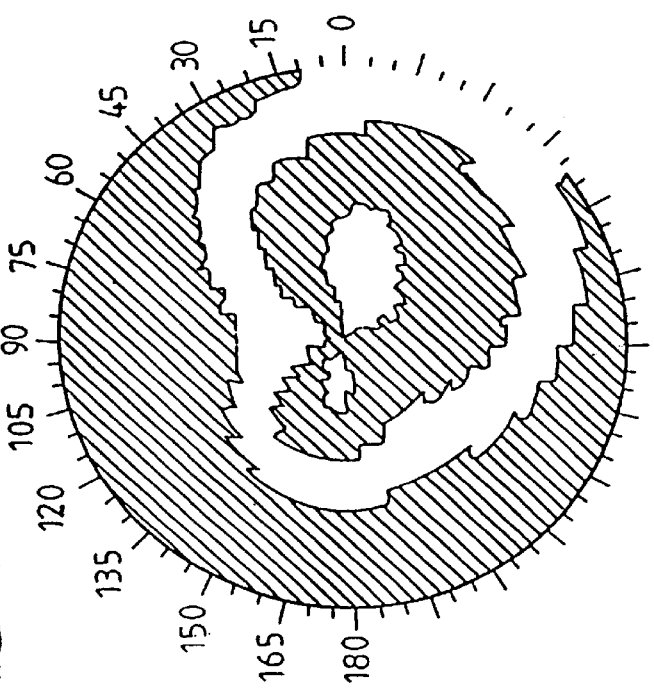

Referring now to FIG. 2, the keratometer of the preferred embodiment comprises a Placido or similar target, a lens system, a CCD (Charge Coupled Device) camera 50 for receiving the reflection of the Placido 2 from the eye and an image processing sub-system 48.

Figure 15:
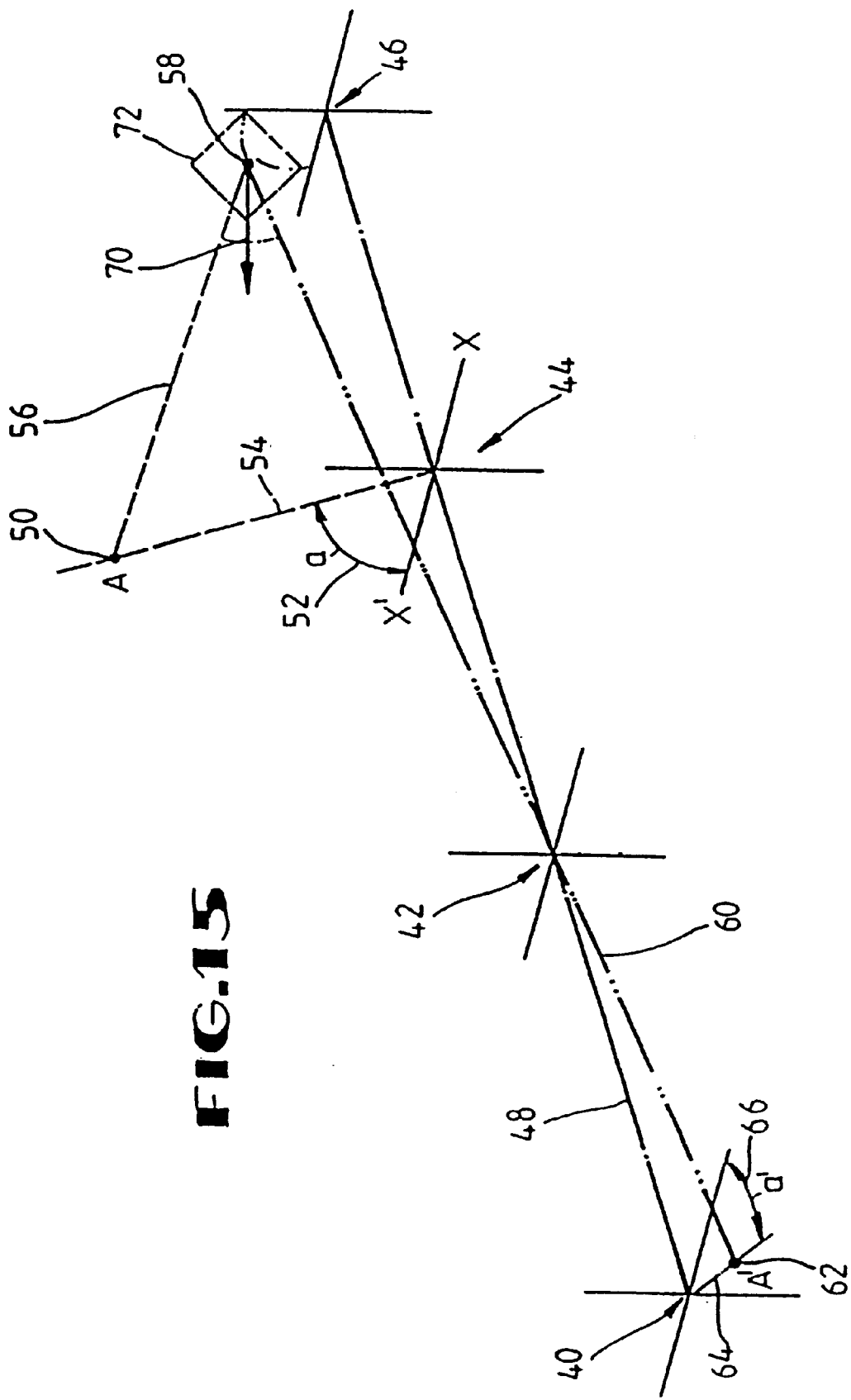
FIG. 15 is a graphical representation of the checkered Placido apparatus in operation.
Figure 16:
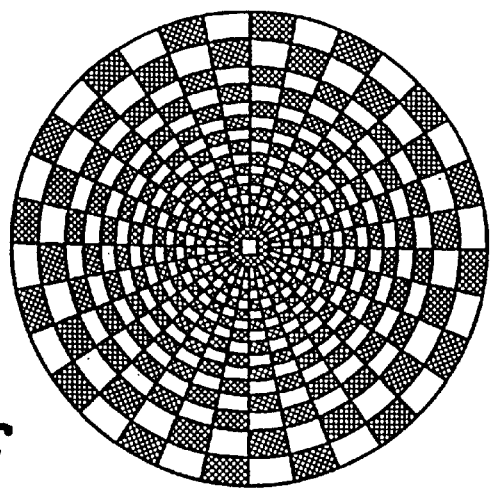
FIG. 16 is a front view of a checkered Placido apparatus.
Figure 17:
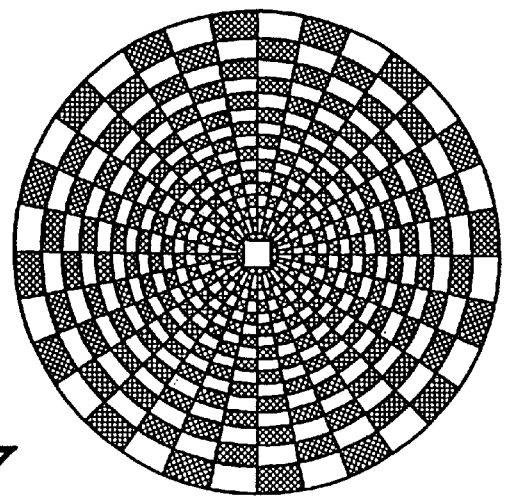
FIG. 17 is a rearview of a checkered Placido apparatus.

The eye to be examined is positioned according to conventional techniques preferably at a distance of 3 inches from the Placido and centered on the optical system. Referring to FIG. 15 for more detail the Placido is in the form of a trans-illuminated surface of translucent material 220 with the CCD camera lens centered in the Placido, and with the lens, in turn, surrounded by concentric circles of opaque material 221. The Placido is illuminated by one or more lamps 222 placed behind the disc surface so the translucent areas are bright circles as viewed by the subject. By this technique an image is provided in a plane 223 posterior to the normal corneal surface of the eye 224. Referring back to FIG. 2, the reflection of this image is received by a CCD camera after passing through the lens. The lens preferably includes an objective lens 53 located at or near its focal length from the eye. A beam splitter or mirror 15 may be included along with a second lens 52 whereby a portion of the image formed by the objective lens may be diverted to a camera port for photographic recordation of the eye and the Placido reflection. Otherwise the remaining image portion is brought into focus at the photo-sensitive surface of the CCD camera 51.

The subject is placed in front of the instrument with the chin supported in a rest (24) which may be adjusted for subject size in terms of chin to eye dimension. This adjustment (25) is typically a screw operated device. The optical assembly (58) is mounted in suitable "slides" or rollers (45, 46) which permit motion in two perpendicular planes without rotation so that either eye may be aligned on the optical axis and the image brought into critical focus by the motions. The Placido (2) is illuminated from behind by a lamp (27) which may be a circular fluorescent tube or other type as desired. The assembly is also moveable in the vertical axis which could be by a means of a slide (32, 33) under control of a screw (31). The rotation of the screw may be by a knob or a motor drive comprising a motor (40), pulleys (37, 39) and a cooperating belt (38) or other suitable means to permit the elevation of the optical axis to be under operator control for alignment of the optical axis of the instrument with the eye to be measured. The action of a "joy-stick" (42) mounted in a ball and socket system (43) under operator control via a cam or friction member (44) preferably propels the instrument on the slides, rollers or wheels (45, 46) to facilitate the positioning and focus steps. The present system in accordance with the invention utilizes a positioner assembly from SCO, Scandicci, Florence, Italy. A brow rest (26) may be mounted on the head support system (49) to insure the fixed position of the eye to the instrument while the adjustment and measurement are made. The patient is requested to focus his eye on the fixation target (79) to assure the coincidence of the optical axes of the instrument with the eye (1). After the positioning and focus step, the operator presses the switch (41) or a foot operated switch, at which time the portions of the image relating to the measurement to be made are captured by the electronic assembly (48) and suitable power supply (47) operatively associated therewith.

An object (the Placido) is reflected from the surface of the cornea and the size of the reflection is measured. The focal length of a convex mirror is one-half of the radius of curvature and the image and object sizes can be related to the focal length. The object in this case is preferably a Placido or Placido's disc.

The data points which are recorded in memory comprise pixel numbers which denote the locus in X, Y terms of each brightness transition in the picture which are over threshold magnitude. These points are contaminated to some extent by random noise and so must be treated to remove the noise, establish centering and focus accuracy and general quality prior to being converted into final form for use in standard display algorithms. As the data points are stored in memory at the time of recordation, the points which define line numbers can be identified by addition of a flag bit in the position commonly occupied by the sign bit. This is possible because the data points all bear a common positive sign and makes sorting simpler by making use of a sign compare instruction available in most computers. The line numbers are stored as a paired table with the data points provided by the pixel numbers in the measurement and the process continues until all data points are so sorted. The end of data in storage is indicated by either a line number or a pixel number being equal to zero which is caused by clearing the entire data memory to zeros prior to each measurement. This technique reduces the number of data points to be treated in the ensuing calculations. A numerical mask is set into the software to define a small area at the center of the picture which defined the location in which the fixation target reflection will be found if the instrument is properly aligned with the eye (1). The reflection of the fixation target should be inside this mask for best accuracy. The data points within a slightly larger area are averaged to define the optical center of the data to be treated.

If the average data point is within the mask area, it is stored as the center point for polar data form conversion; if outside the mask the measurement is aborted. The operator may be notified of the error or an automatic repeat measurement for some given number of tries, commonly (3) can be done prior to the notification as desired.

After the data format conversion from cartesian to polar form the angle count is set to zero and the points in radial sequence are stored in a table. This is repeated for as many angles as are desired. The increase in the number of angles enhances later display use but increases the calculation time so the number of angles is user selected.

After all desired angles have been converted, the data points are examined by distance from center as groups. It should be noted that this is in sequence terms as opposed to discrete distance terms in that the reflection will be closed, nested curves, but not circles or other regular figures in most cases.

The radially selected groups are subjected to a smoothing process such as least squares or moving average window to define the shape of the reflection of the Placido. To provide the common form of central K1, K2, Cylinder and Axis, the innermost smooth curve may be presumed to be an ellipse and the calculations produce the "best fit" ellipse from the smoothed data. From this the K1 and K2 are determined by look up and interpolation from the calibration data table and the numerical difference becomes "Cylinder" or astigmatism. The Axis is, of course, the major axis angle of the determined ellipse in anti-clockwise form from zero degrees in the horizontal plane extending to the right of the origin.

The remaining steps take each set of points for successive concentric reflections and smooth them in like fashion. Any data point which fails to fit the smooth curve by more than two standard deviations or other like threshold parameter is then deleted and the data resmoothed. The smoothed data are then converted to X, Y and millimeter radius of surface curvature form by table look up for use in any desired display format.

The area of corneal coverage is 0.9 mm–9.0 mm. (@42.5D). The axis range is 0–360 degrees (1 degree increments). The diopter range is 9D–99D. The resolution is +/−0.25 diopters. The dimensions of an integrated system embodiment are 23"D×18"W×24"H, 80 pounds, otherwise, the system components can be modularized and provided on a compact mobile pedestal table.

System Components

The system in accordance with the invention is comprised of a photokeratoscope, a Placido 2, a patient focusing assembly 202, a computer 203, a high resolution CCD video camera, a 14" VGA color monitor 200 and an image processing subsystem. The system is mounted on a table top which is attached to a moveable pedestal 205.

The illustrative system in accordance with the invention includes the following components:

Photokeratoscope, case, CCD camera, Placido, light chamber, optics assembly, patient focusing assembly, positioning base/chinrest, IBM AT compatible computer or 80386 based computer, 101 Key Enhanced Keyboard, 40 Megabyte Hard Disc Drive, 1.44 Megabyte Floppy disc Drive, High Resolution CCD Video Camera, 14" VGA Color Monitor, Image Processing Sub-System, Image processing algorithms, frame grabber board, power supply board, pedestal, tabletop.

Image Processing

The image processing software and all other software used in the system in accordance with the invention is set out in the appendix. The software is adapted for speed and performance in numerous ways. The software uses integer mathematics in lieu of floating point mathematics to obtain a substantial increase in speed on the family of processors used by the system, the Intel X86 family of processors, available from Intel Corporation, Santa Clara Calif. These techniques improve performance on any processor, however. Integer math is even faster than using a co-processor for floating point operations. The math uses a fixed point operator. For instance, to use the number 3.279 the proxy number 3,279 is manipulated instead using integer math; the decimal point is later placed in the result as necessary. This is much faster than floating point math. The system in accordance with the invention also uses integer math for sines and cosines, simply scaled by 1000 to give a significant increase in performance. Because only three significant digits are necessary, this scale by 1000 operation works adequately to give three significant digits.

Numerous performance enhancements are detailed in the source listing. An important factor in performance enhancement is the architectural design of the software as well as the selection of steps and sequence used to perform the image processing and other function. Additionally the technologies of image processing, parallel processing and expert systems are incorporated into the software design.

The software design is parallel. It can be executed on a parallel processor such as a super computer and would not be forced to be sequential. Therefore the architecture has been designed so that it can be executed in a parallel implementation.

Edge Detection

Figure 12J:
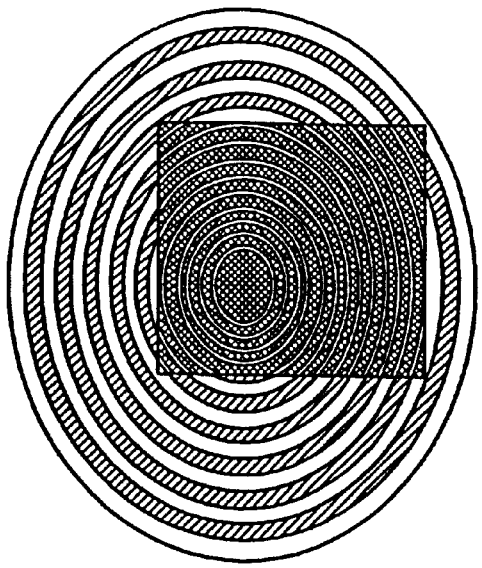
Figure 12K:
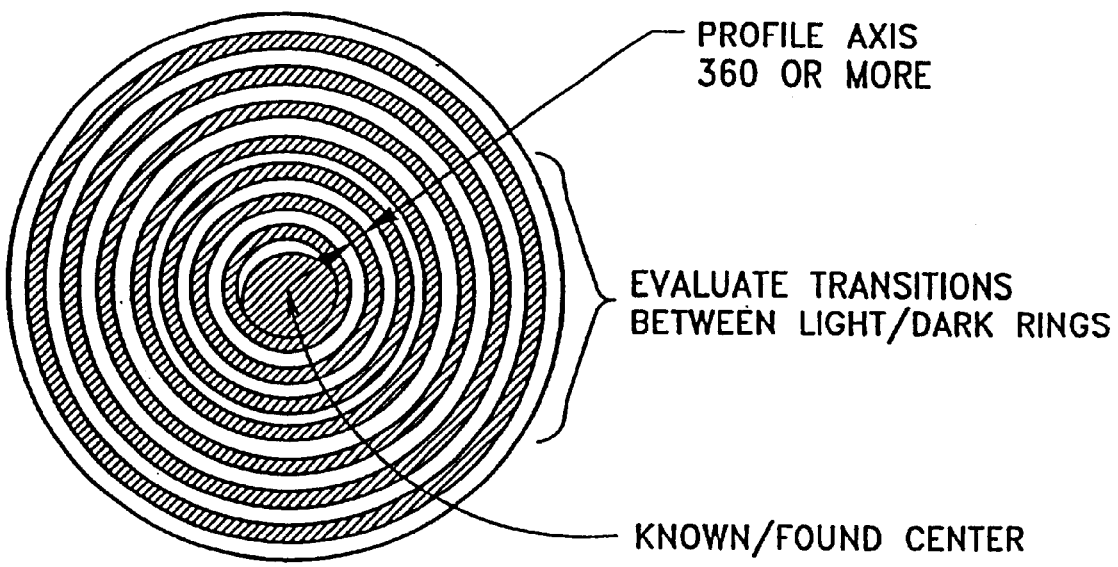

The system in accordance with the invention uses an edge detection algorithm implemented in software. Each Placido ring that is reflected in the cornea is seen as two edges by the edge detector. Other known systems use peak amplitude to detect Placido ring locations which is less accurate and generates fewer data points for post image capture analysis. The system in accordance with the invention uses the edge detection software to sense the interior and exterior edge of each ring (see FIG. 12K). The image processing software then counts the number of pixels to each edge of a Placido ring, and then rotates 1 degree and repeats the process of counting pixels.

For example, if nine Placido rings were used and reflected off of the cornea they would generate eighteen ring edges; this implies 360 degrees×18 edges=5760 points of corneal topographic information. Older style keratometers only utilized four data points, the radius to a single mire or ring measured 90 degrees apart and then photographed the mire reflected in the cornea to quantify a spherical characteristics of the cornea. The total analysis alone took over 20 minutes to complete. The system in accordance with the invention performs a full 360 degree analysis in under 15 seconds.

The number of pixels counted to the edge of a Placido ring corresponds to a particular radius of curvature when compared to the calibration curve for the system. The edge detector which resides as software in the computer looks at the pattern of rings reflected from the cornea on the CCD camera and captured by the frame grabber board and counts the number of pixels to the edge of each concentric ring. The number of pixels counted to each ring edge is proportional to the radius of curvature of the corneal surface of the eye at that point.

The image processing software resides in the integrated computer performing edge detection to find the edge of each Placido ring reflected on the corneal surface, then image processing algorithm software creates a table of pixel distances to each Placido ring edge thus generating a pixel count or distance to a ring edge that is proportional to the corneal radius of curvature. The system in accordance with the invention uses sub-pixels $\frac{1}{10}$ resolution to determine position of edges and diopter measurements. These calculated pixel distances are compared to the calibration curve to generate the topographic curvature for the object cornea.

Software also includes function for patient history, data base management, displays, driving the video board, writing pixels to the display board buffer, site specific profiles for communications parameters, doctor preferences for number of colors on the screen, file manipulation code, menus and numerous other functions evident upon examination of the software source listings in the appendix.

Calibration Curve

The illustrative system in accordance with the invention generates a calibration curve by imaging objects with a known radius of curvature. The calibration routine calculates and stores a look up table (essentially a calibration curve) for each of four calibration spheres in the current design, each table corresponding to the number of pixels counted for this known radius of curvature. The number of calibration spheres can easily be increased or decreased. Presently these four tables are used to generate an interpolated calibration curve (pixel versus diopter or radius of curvature). This best-fit curve, presently calibrated to four known radius-of-curvature calibration objects, gives the radius of curvature for a given pixel count when imaging an object with an unknown radius of curvature. The software source code is listed fully in the appendix.

Data Presentation and Display

Corneal information can be reported as a set of numerical values or may be displayed in a color-graphic presentation. The system in accordance with the invention is capable of graphical presentation of the 3 mm, 5 mm and 7 mm zones, or as a corneal contour profile graphic of any meridian. The system in accordance with the invention can also generate topographic color coded surface maps in either diopter or millimeter radius of curvature scales. Up to four surface maps can be displayed together for comparative analysis. Patient exams can be archived to floppy disc and recalled at any time. Permanent records can be produced via optional Polaroid camera or color graphics printer.

The colored graphics presentation can be utilized to show where to make correcting incisions into the cornea during a radial keratotomy or laser sculpturing procedure of the cornea. A video display monitor is utilized to view the graphic presentation. Video graphics can be saved on the system printer or on disc for archival purposes.

Graphical displays can also be useful to record the topographic history of the cornea during the healing process. The cornea can take months and sometimes even years to heal: the cornea has no blood in it, so it repairs similar to a missing finger nail; it does not scab over and heal within a week or so. Such historical topographic data enables a doctor to make necessary adjustments as the cornea heals. The doctor can tighten or loosen sutures or make other correcting adjustments to optimize the corrective effects of surgery on the shape of the cornea.

Graphical presentations can also be used to compare the topographic corneal characteristics before and after surgery. The difference between the two can also be shown so that a physician can observe how the surgery has affected the topography of the cornea. Examples of the graphic presentations are presented in FIGS. 3A–3L.

Figure 3H:
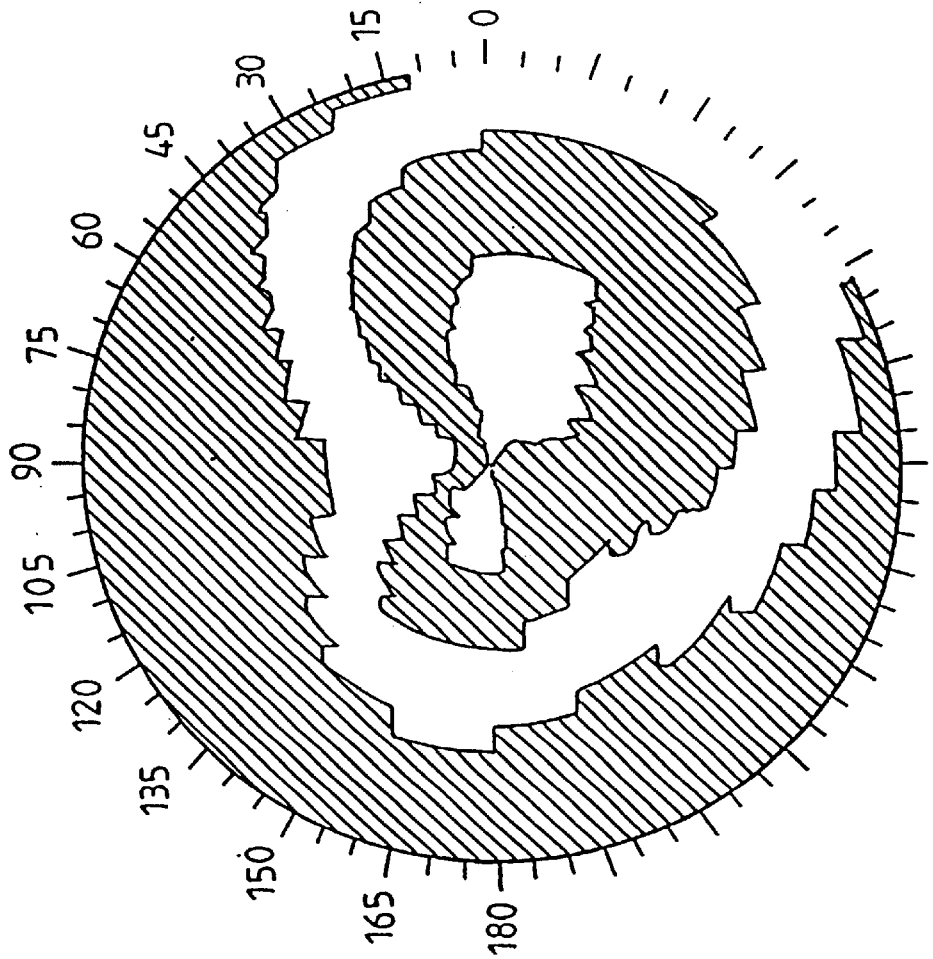
Figures 1, 31:
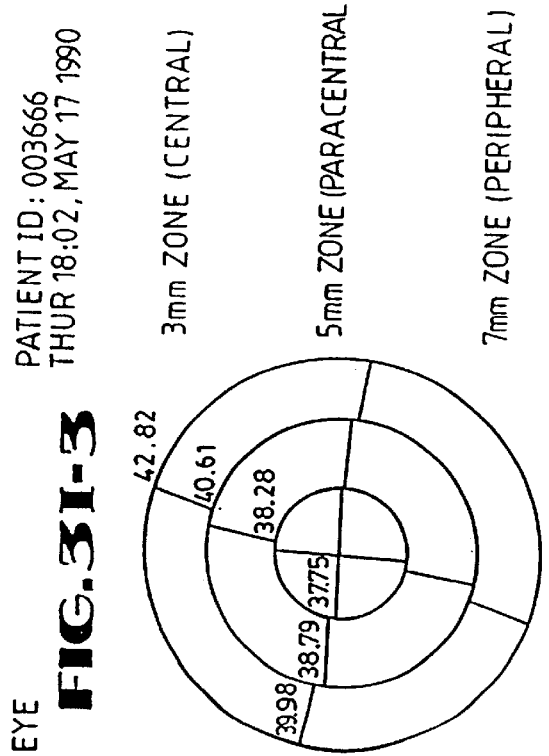
Figures 3, 31:
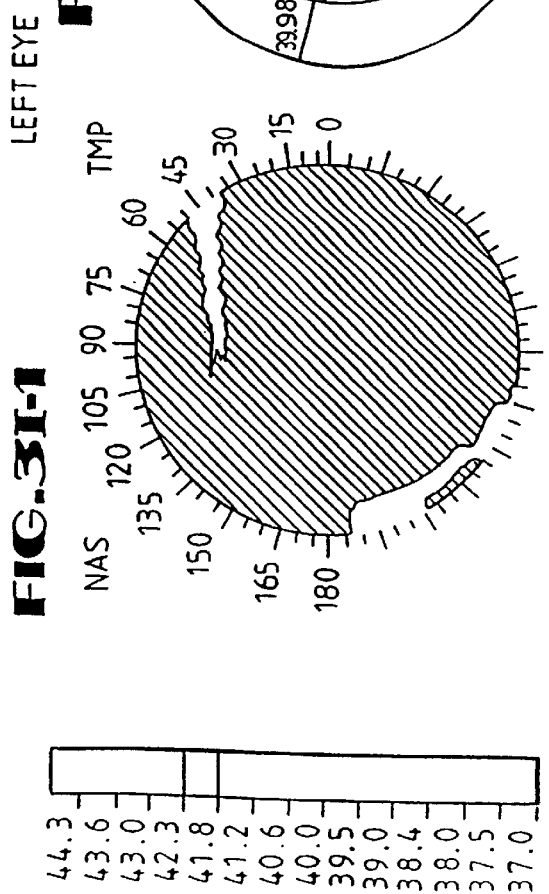
Figures 2, 31:
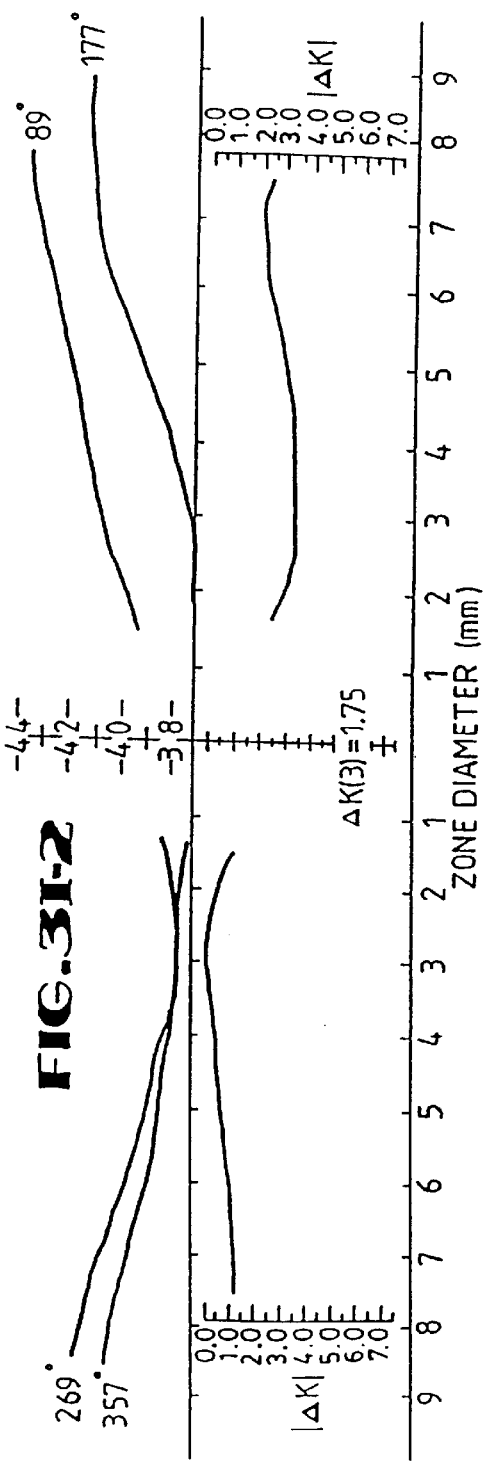
FIG. 2 is a cross section of the system.
Figure 3J:
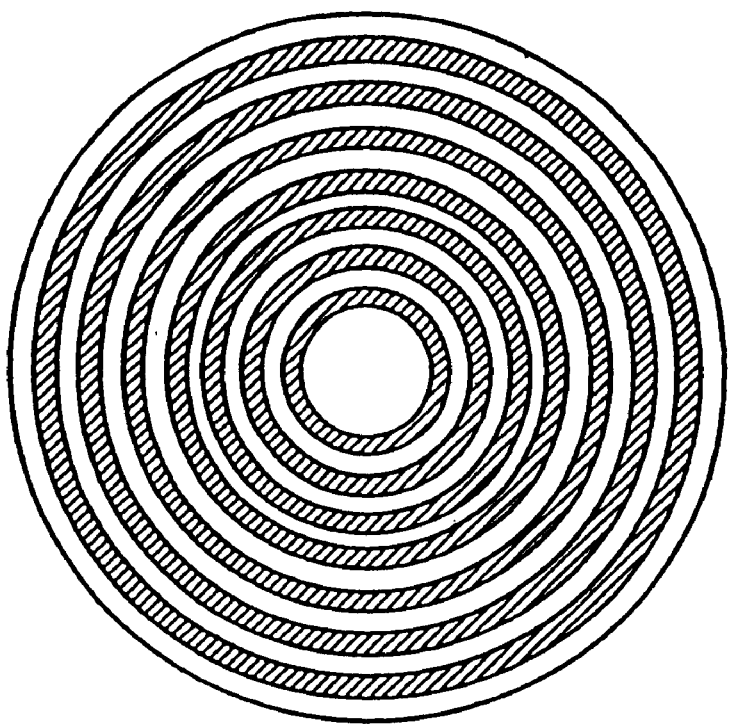

The graphic display can be chosen from menus as shown in FIG. 3A using the "Select Display Format" menu. FIG. 3B is an example display of keratometric data (orthogonal). FIG. 3C is an example display of keratometric data showing astigmatism in a "torque display" in which the 3 mm, 5 mm and 7 mm topographies are overlaid in one display. FIG. 3D is a profile graph which can be generated for any 2 meridians. FIG. 3E is a tabular display of keratometric data which can be generated for any 2 meridians. FIG. 3F is an example display of a contact lens fitting map showing the dioptric correction for different points on the cornea. FIG. 3G is an example of a comparative isodioptric mapping that can be generated to compare 1, 2, 3 or 4 eyes. FIG. 3H is a color map with nonnalized dioptric scale. FIG. 3I is an example of a data overview display. FIG. 3J is an example of display eye image which is a display of the eye and the Placido ring image upon it. FIG. 3K is an example of the contact lens fitting display. FIG. 3L is an example of comparative isodioptric color mapping. FIG. 3M is an example of a tabular display of curvature data in any two selected meridians.

The data organization and presentation software source code is listed in appendix 1.

Precise Placido Positioning and Focusing Aid

The size of the reflection of the Placido in the cornea, and therefore the calculated perceived radius of curvature for a particular zone of the cornea, is a function of the distance from the eye to the Placido. Therefore it is desirable that this distance be the same each time the doctor analyzes the topography of the cornea. A change in the distance would render an erroneous calculation as to the topography of the cornea. For instance, should the Placido be positioned slightly closer to the cornea on a second "snapshot," the rings would appear farther apart and more pixels would be counted between the rings even though the shape of the cornea has not changed, and the results would erroneously indicate an increase in the millimeter radius of curvature.

In the present embodiment the actual Placido is approximately 3" from the eye; however, a focus aid is employed to exactly position the Placido to the same position for each diagnostic session. The focusing aid is much closer to the eye than the actual Placido and it projects focusing crosshairs on to the eye. These focusing cross hairs constitute a "synthetic Placido" which represents a Placido which is much closer to the eye than the actual Placido. Therefore when the focusing aid or "synthetic Placido" is positioned precisely the positional errors in the actual Placido are negligible. Therefore the deviations in the position of the actual Placido become insignificant and aid accurate and reproducible positioning of the actual Placido, thus reducing inaccuracies in corneal topographic calculations due to positioning errors.

The focusing aid projects focusing cross hairs onto the eye. The focusing aid acts as an optical range finding system to determine when the cornea is in focus. The focusing aid promotes accurate and reproducible eye placement to get exact comparative readings between pre-operative and post-operative corneal topography. Comparative readings are also useful in determining how the corneal shape may change over time during the healing process. The position of the Placido with respect to the eye is important in determining the corneal topography, in both an absolute or a comparative sense. The corneal topographic characteristics are also useful in determining and predicting the after effects of surgery and detecting possible errors that may have occurred in surgery using other diagnostic techniques than the system in accordance with the invention.

The space between the reflected Placido rings is a function of the distance from the eye to the Placido 2. Because the Placido may appear in focus during travel through the depth of field for a particular lens, there can be significant variance in the distance from the Placido to the eye for two different points within the depth of field. A difference in this distance from the Placido to the eye causes a difference in the distance between the Placido concentric circles, inducing an error in measurements of the distance between the Placido lines. The Placido should be positioned at the same distance from the eye each time a measurement is taken so that variations in the distance between reflected Placido lines are caused by variations in corneal topography and not by variations in the distance s from the Placido to the cornea.

Figure 4A:
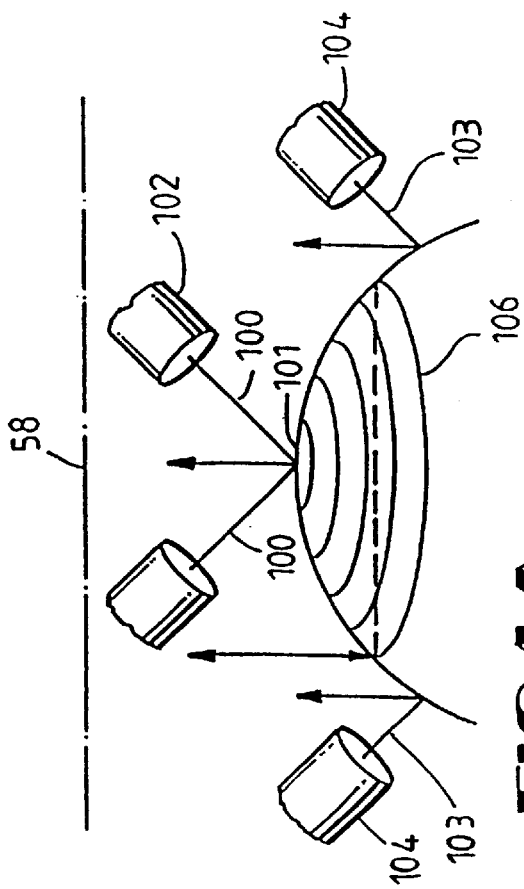
FIGS. 4A and 4B are a graphic presentation of the operation of the focusing aid.
Figure 4B:
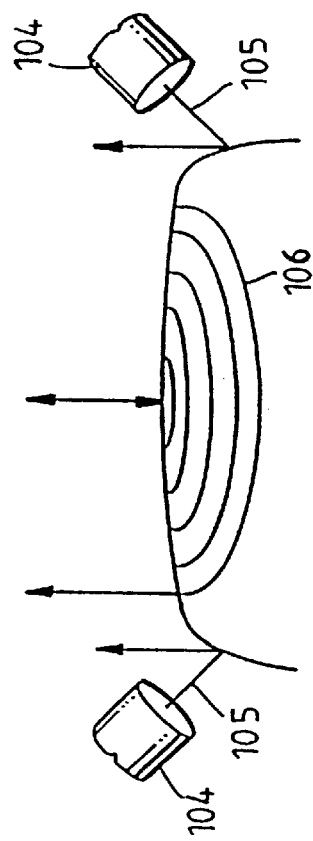

Now referring to FIGS. 4A and 4B, prior art systems use a triangulation method (100) as shown in FIG. 4A. The prior art method employs converging laser beams 100 from lasers 102, to position the apex of the cornea, 101 relative to the optical assembly 58. This method introduces an error in post-surgery keratometric readings, as the tip or apex of the cornea 101 may be depressed substantially from its pre-operation position. This depression causes a flattening of the corneal apex as shown in FIG. 4B. This flattening causes the cornea to be positioned closer to the optical system under the prior art and thus exaggerating the corneal flattening resulting from the surgery. The prior art triangulation focusing method induces an error in the distance to the reference point, the apex of the cornea. The prior art system therefore is less likely to give consistent and repeatable results or measurements because the distance from the optical assembly to the entire cornea changes after surgery inducing an error in postoperative measurement. Moreover, the use of lasers projected onto the cornea is also dangerous as they can damage the tissue.

The illustrative system in accordance with the invention offers an improvement in that these induced errors are reduced to enhance repeatable and accurate results. The present system in accordance with the invention uses two light emitting diodes (LEDs) 104, however another illuminating source or means of projecting an image could be used. These LED projected images do not converge but are pointed at the limbus area at the periphery of the eye. These LEDs project a focus aid image consisting of an "x" or cross hairs 103 onto the outer portion or limbus area of the eye. This outer portion is less susceptible to change through either flattening or steepening than the apex area of the cornea. The change in this limbral area of the cornea after surgery is negligible compared to the change in the apex. Therefore the measurements are more accurate and comparable using the system in accordance with the invention of the present system for pre and post operative corneal curvature changes.

Figure 7:
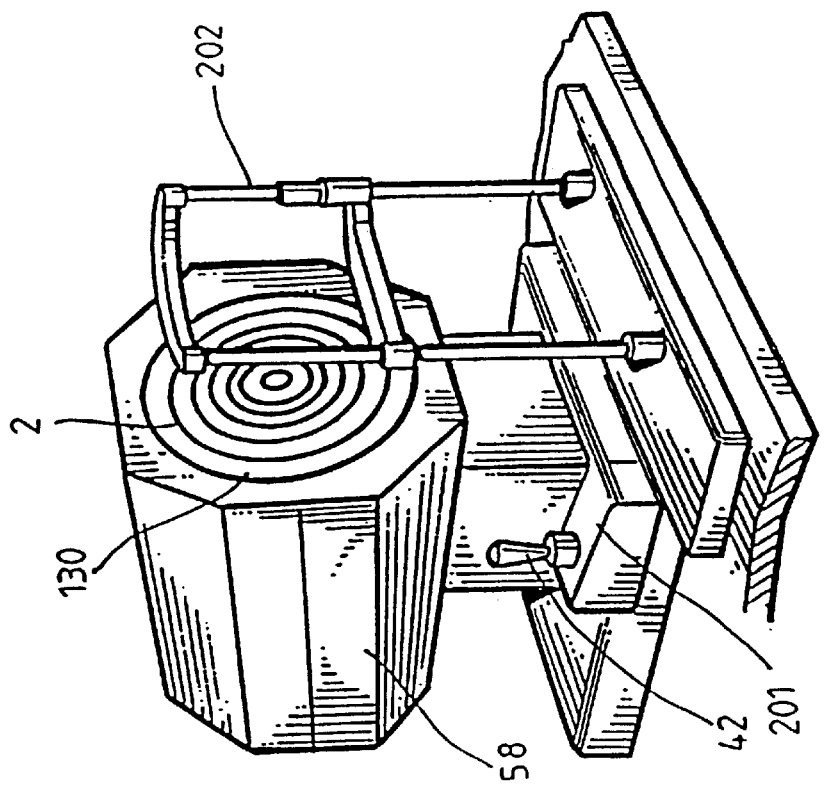
FIG. 7 is operational depiction of the optical assembly and patient positioning assembly.
Figure 1:
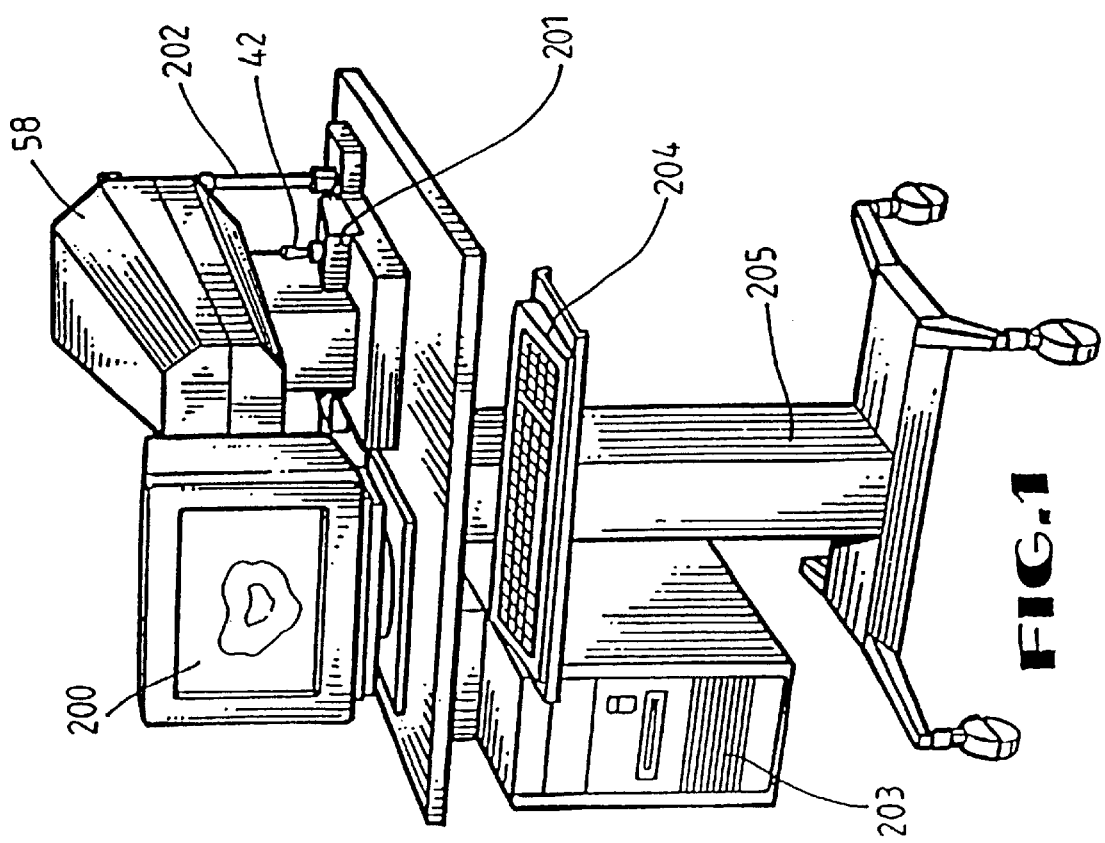
FIG. 1 is an overview of the system.
Figures 2, 8A:
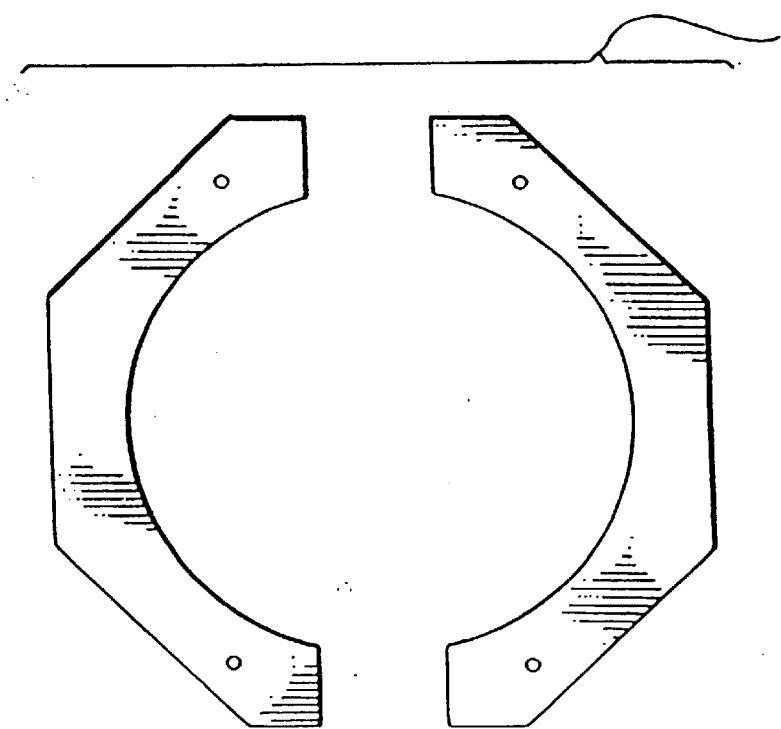
Figures 1, 8A:
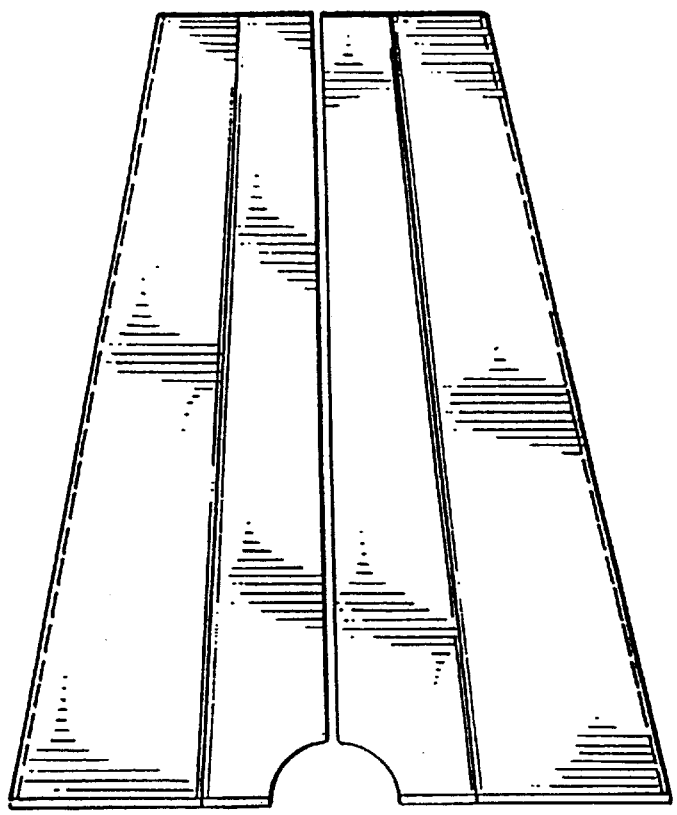
Figures 3, 8B:
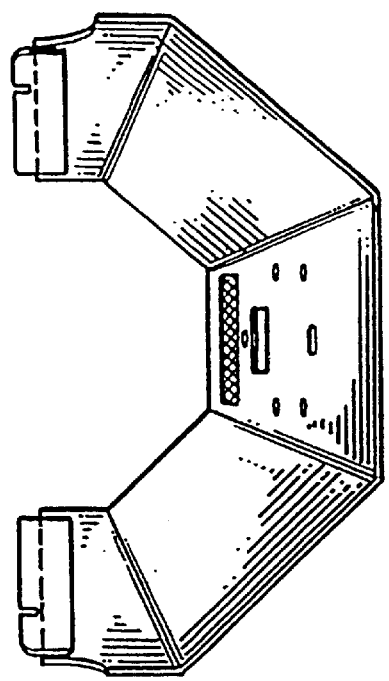
Figures 1, 8B:
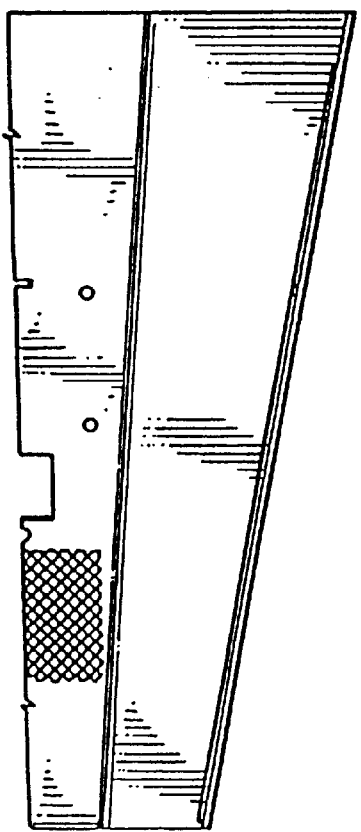
Figures 2, 8B:
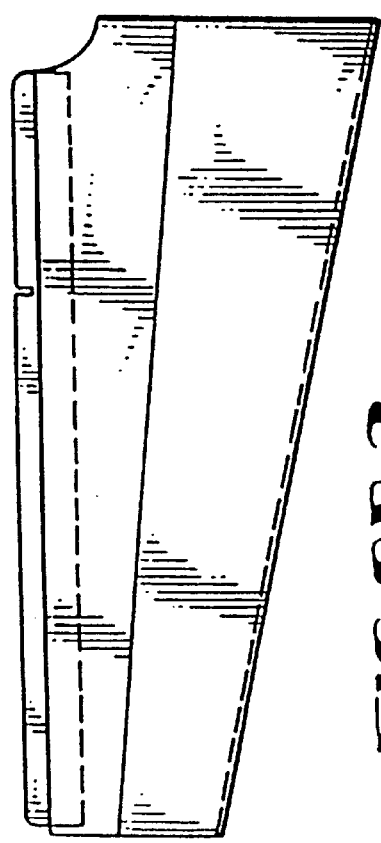
Figures 3, 8C:
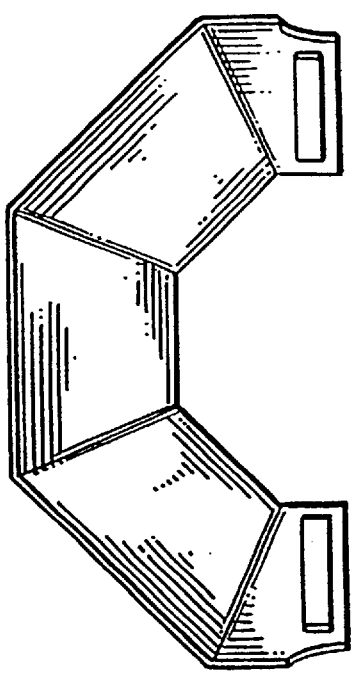
Figure 8D:
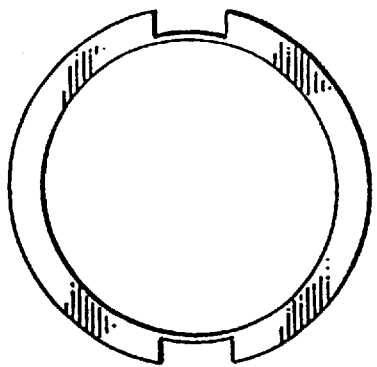
Figures 1, 8C:
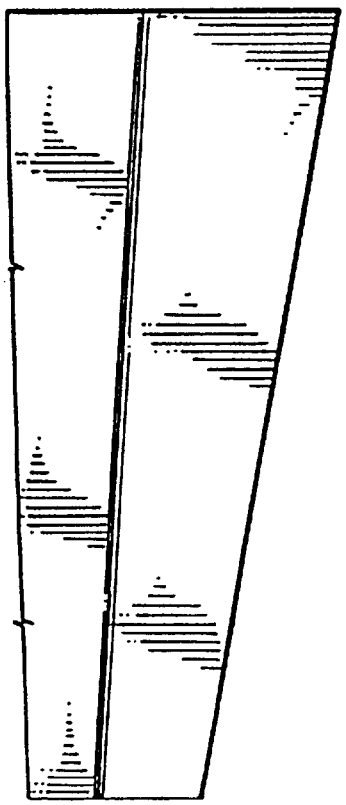
Figures 2, 8C:
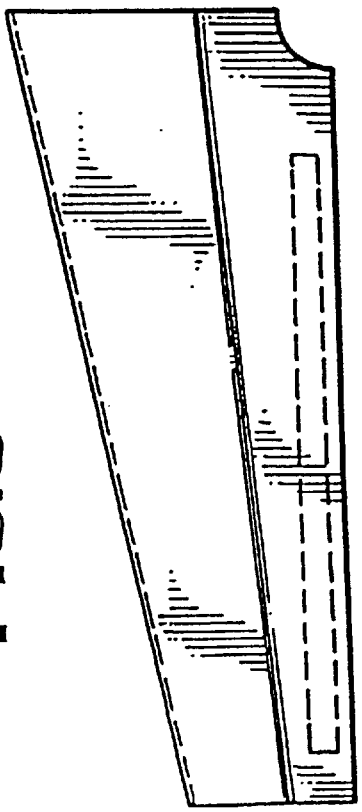
Figures 3, 8E:
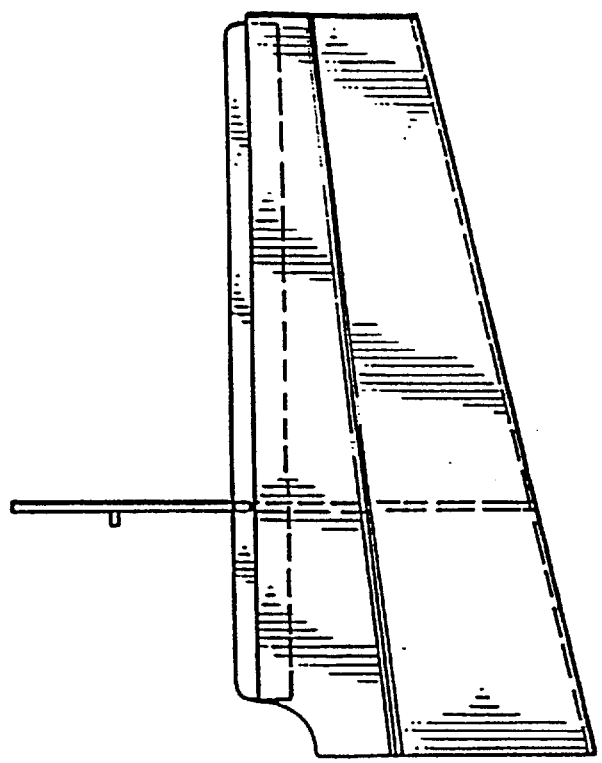
Figures 2, 8E:
Figures 1, 8E:
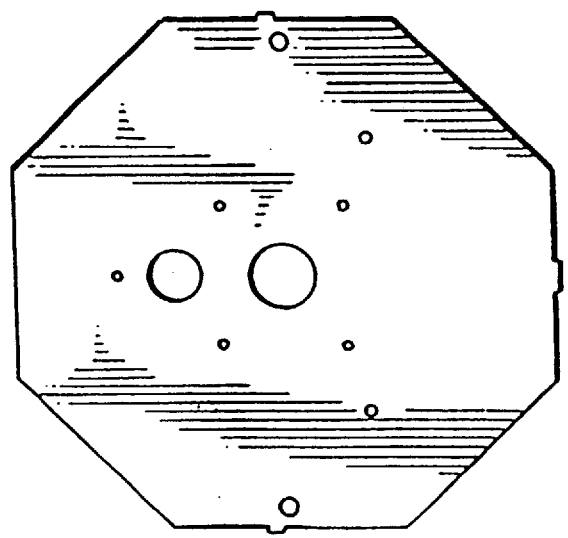
Figures 2, 8F:
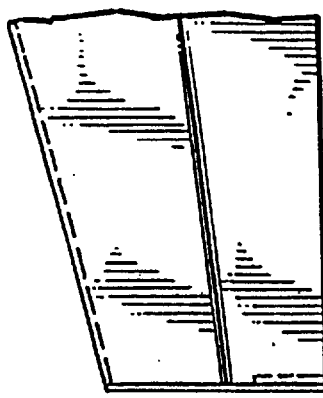
Figures 5, 8F:
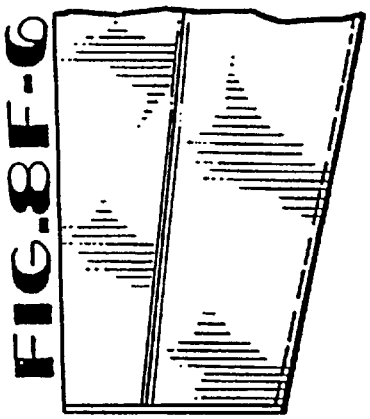
Figures 1, 8F:
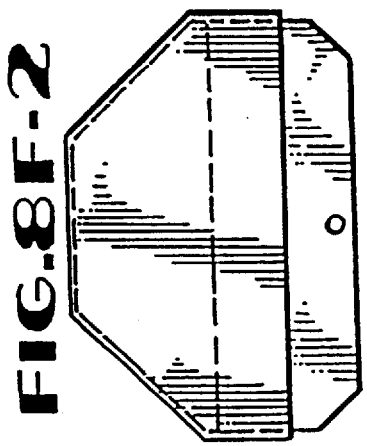
Figures 4, 8F:
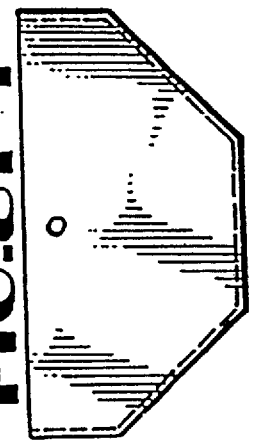
Figures 3, 8F:
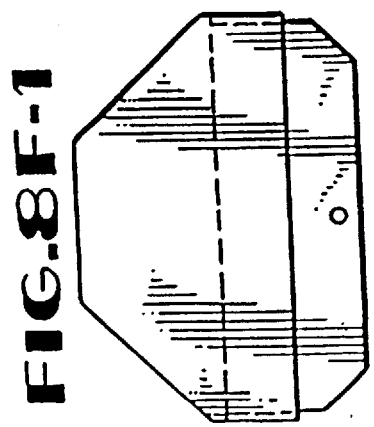
Figures 6, 8F:
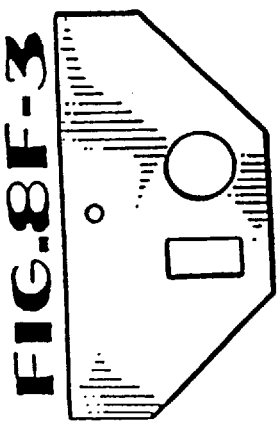
Figures 1, 8G:
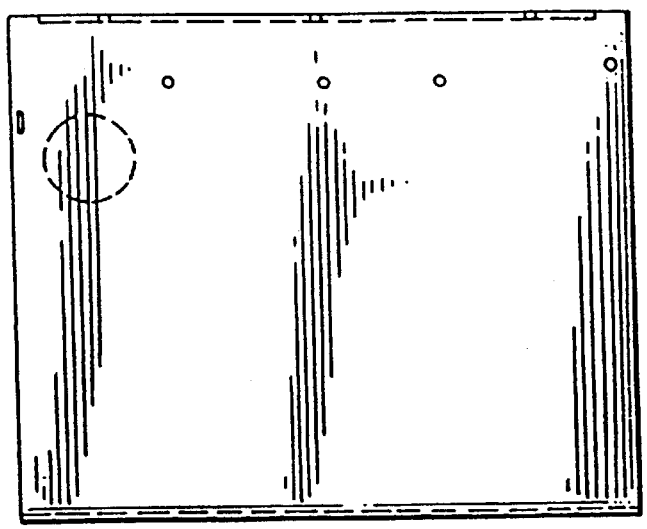
Figures 2, 8G:
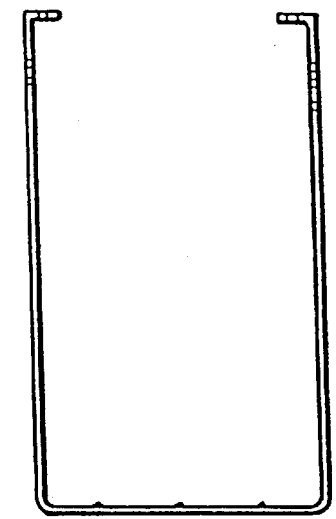
Figures 3, 8G:
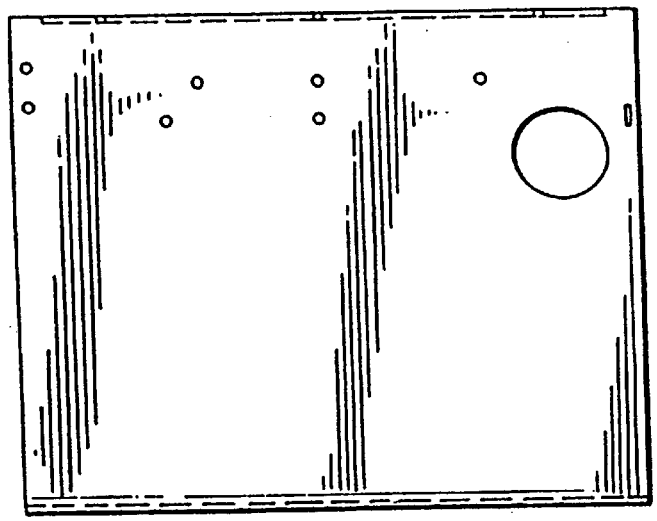
Figures 4, 8G:
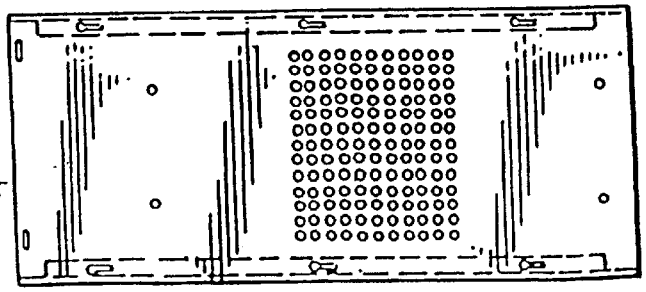
Figure 8:
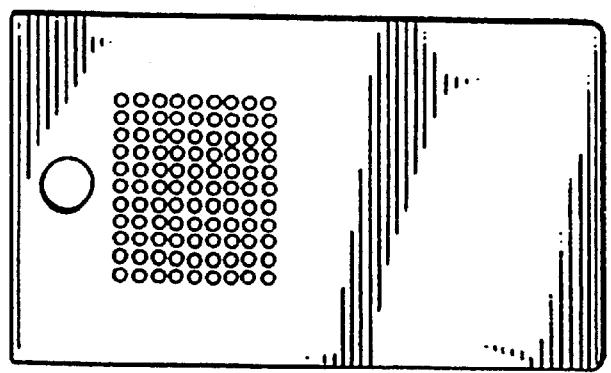
Figure 8:
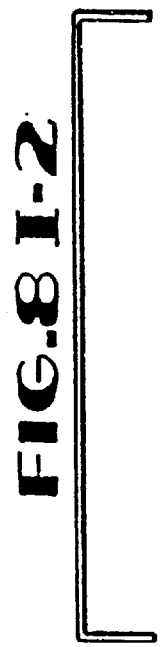
Figure 8:
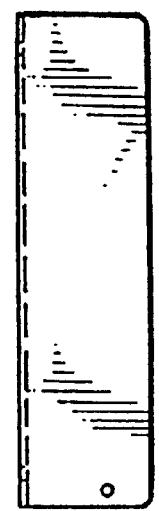
Figure 8:
Figure 8:
Figure 8:
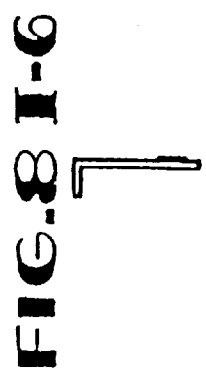
Figure 9:
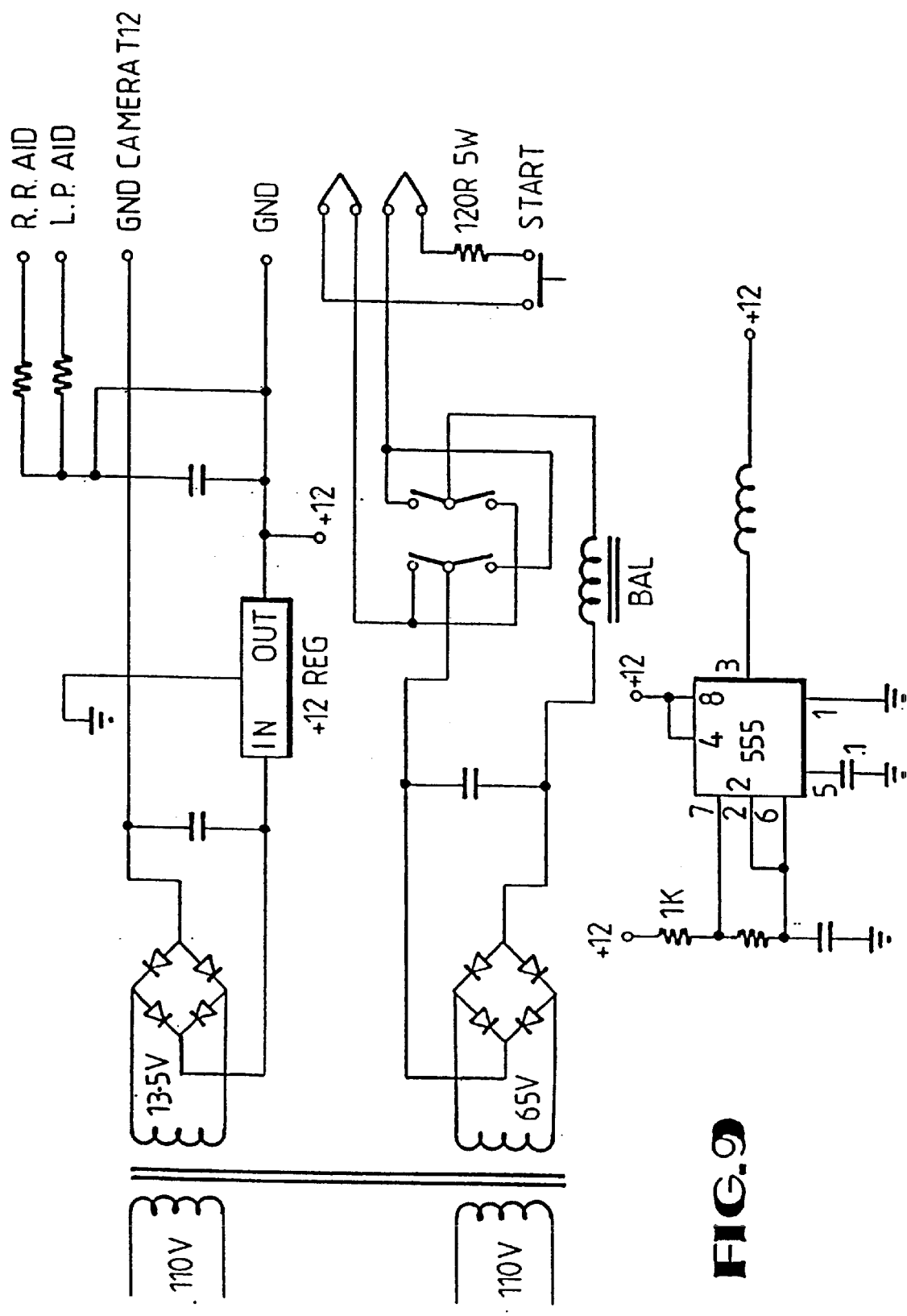
Figure 10A:
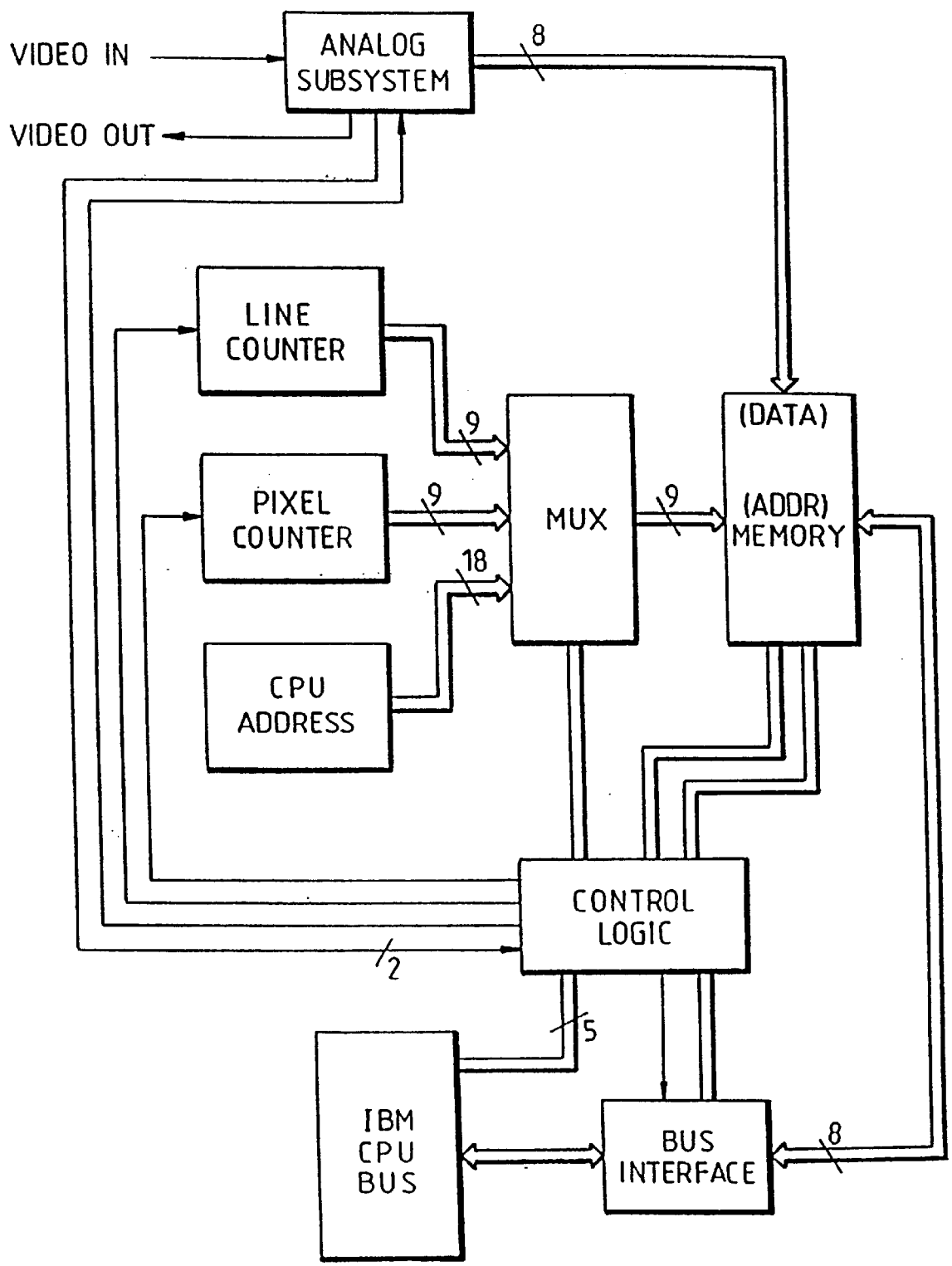
Figures 1, 10B:
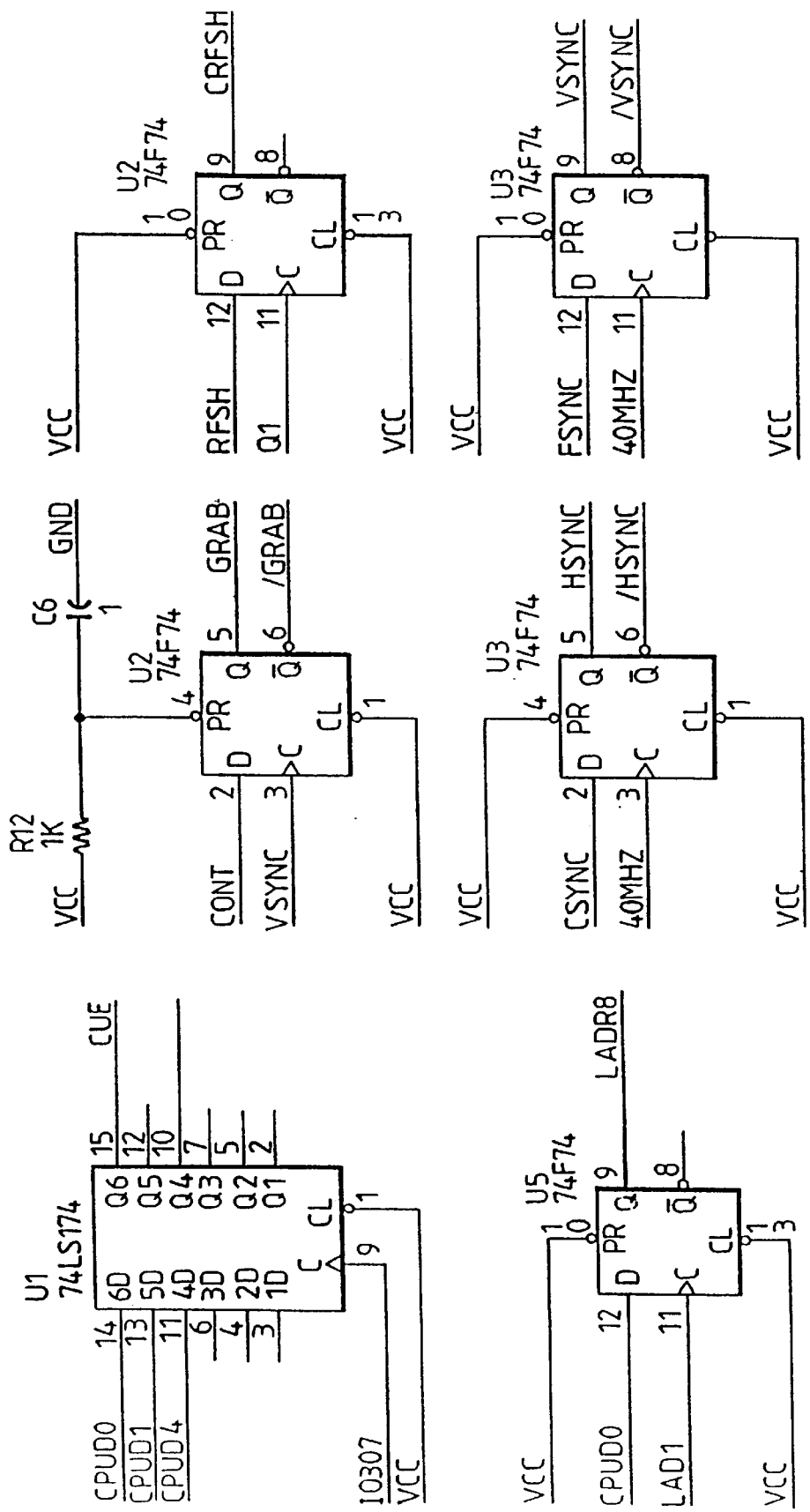
Figures 2, 10E:
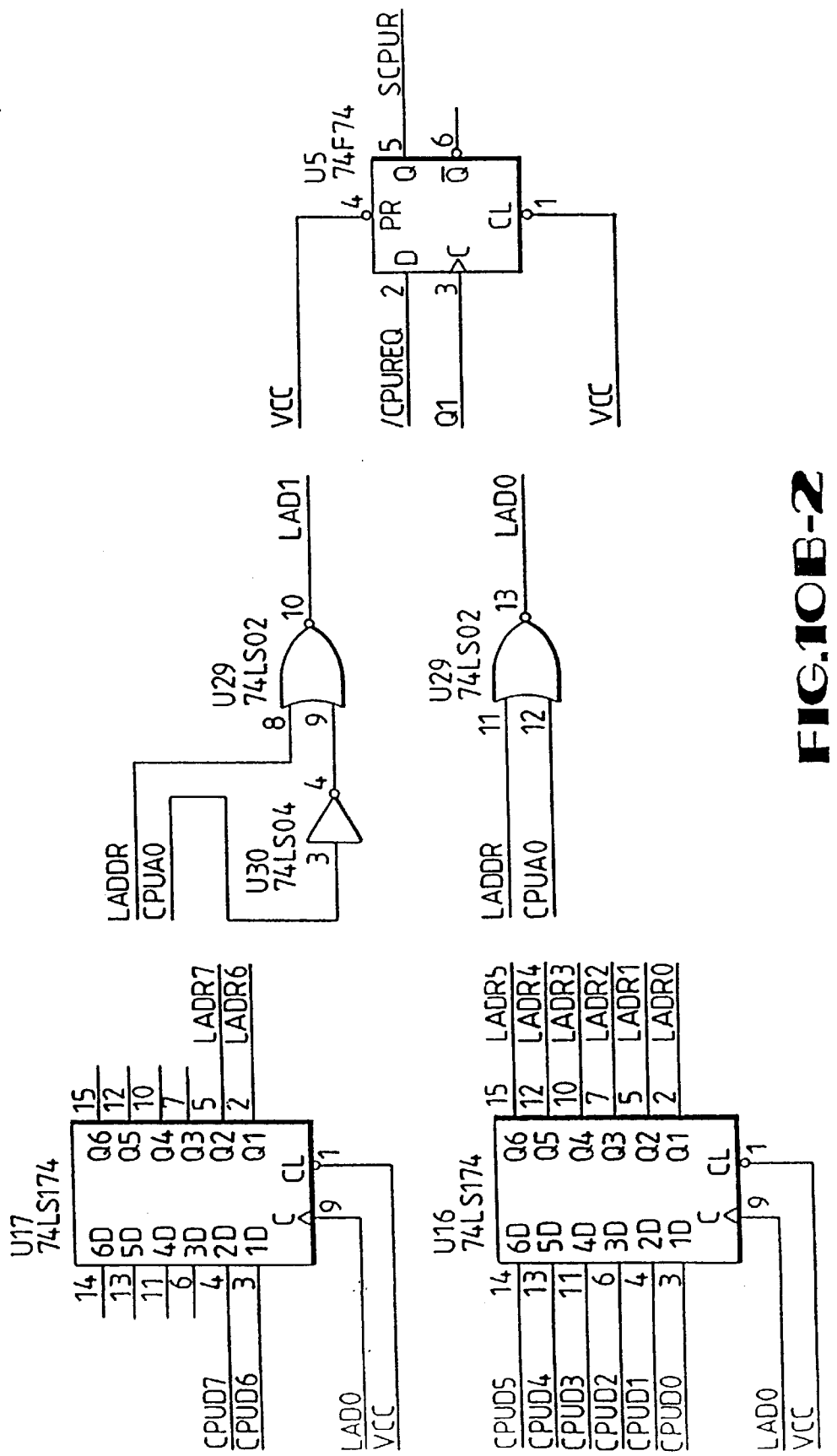
Figure 10E:
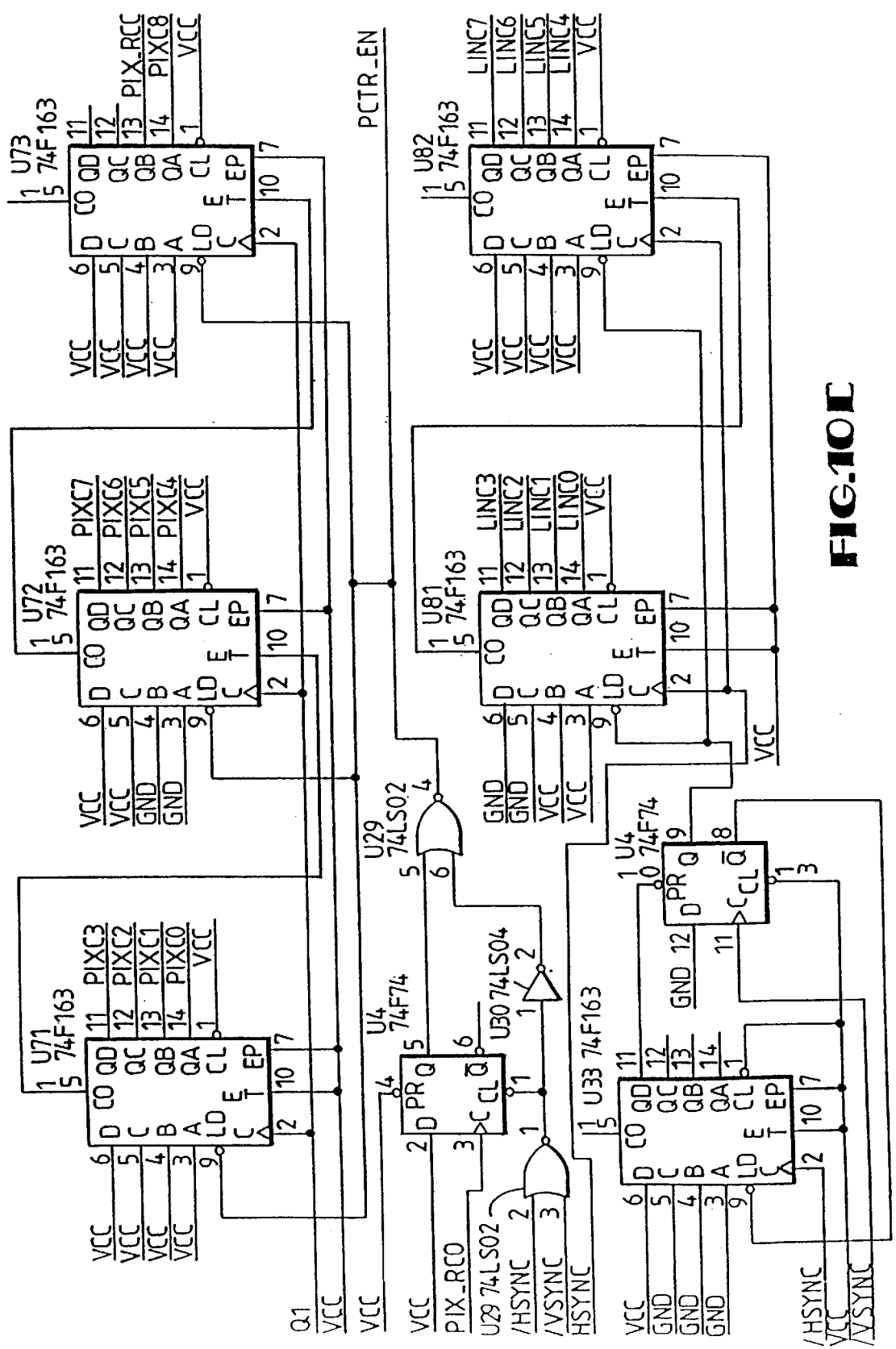
Figure 10D:
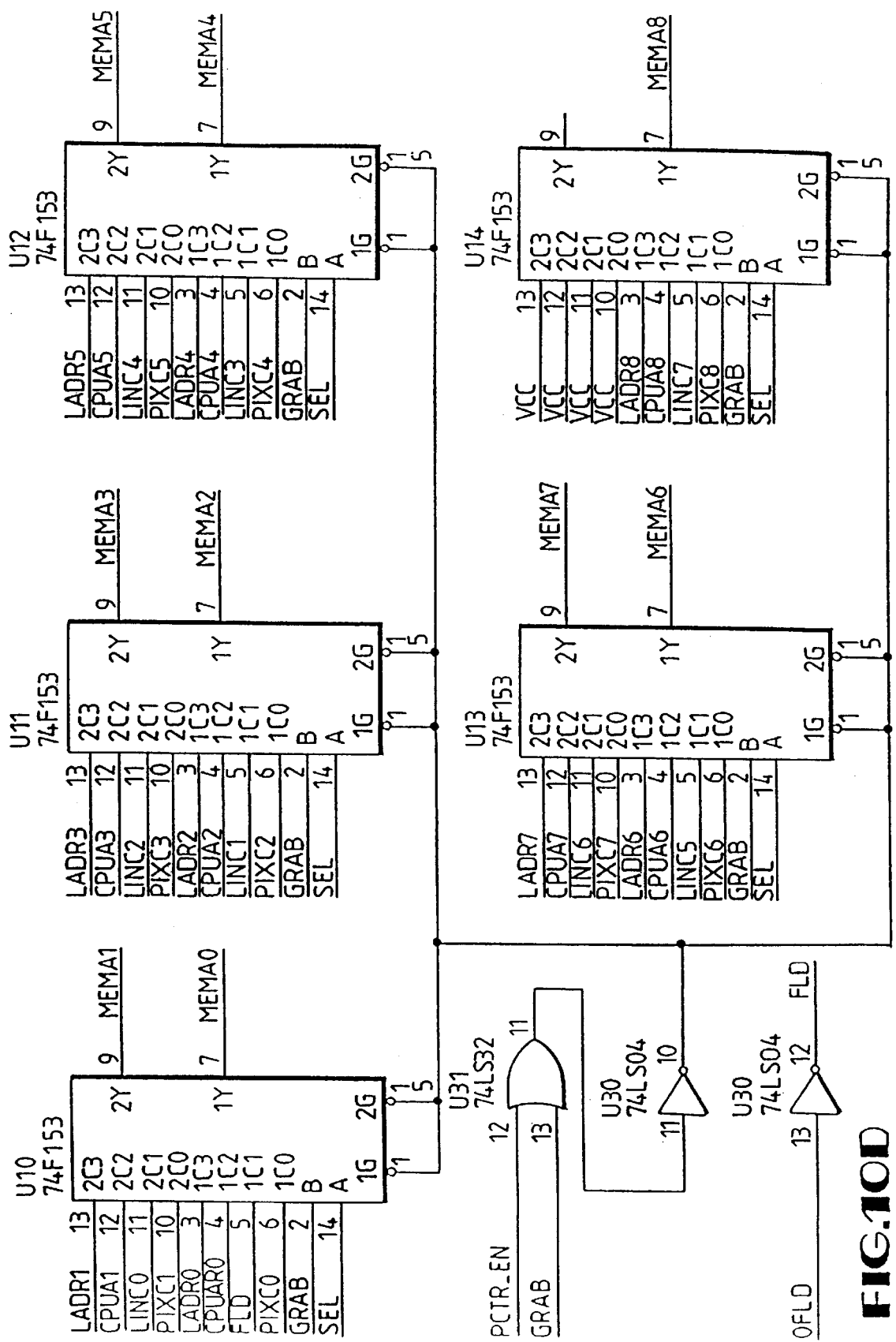
Figure 10F:
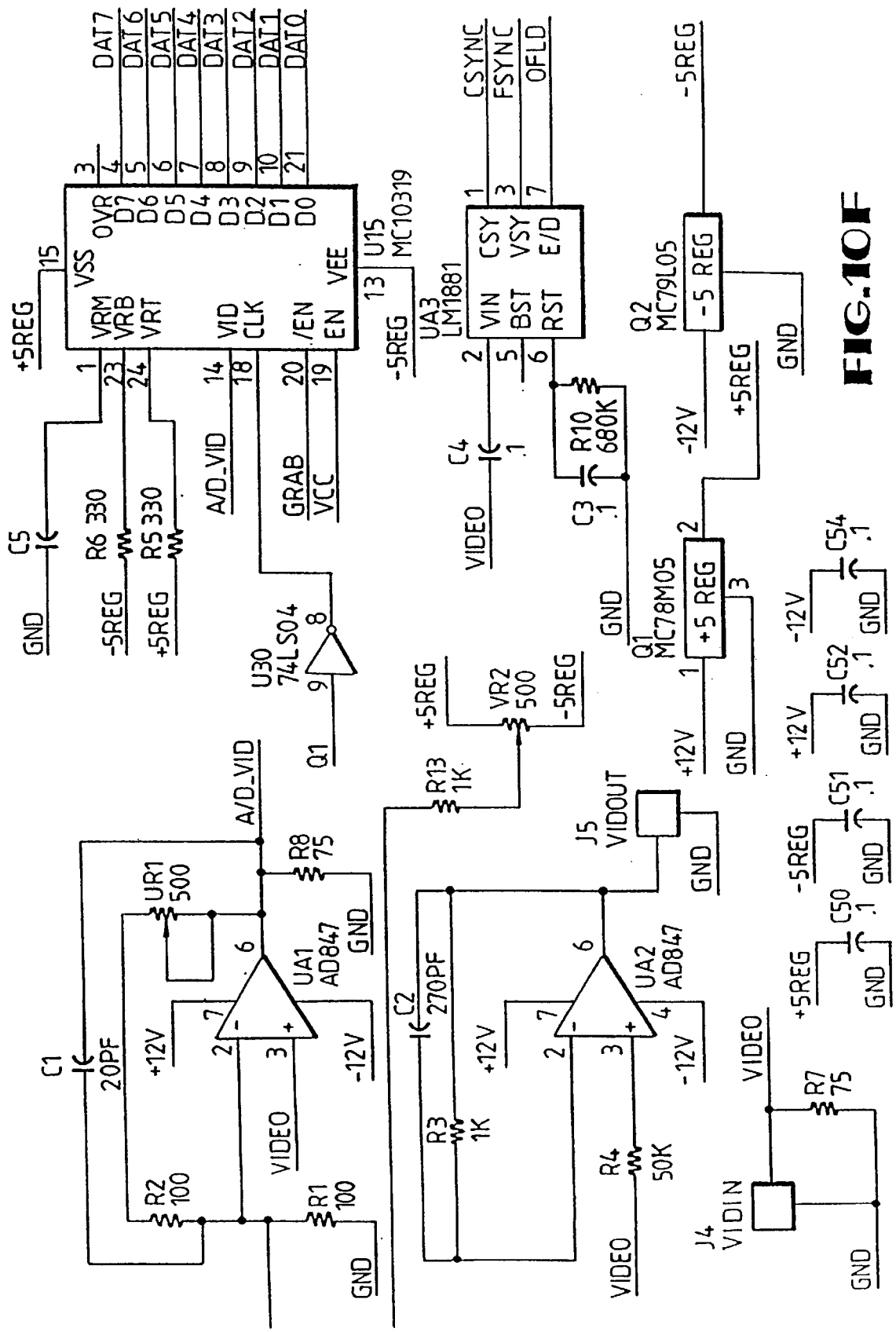
Figures 1, 10G:
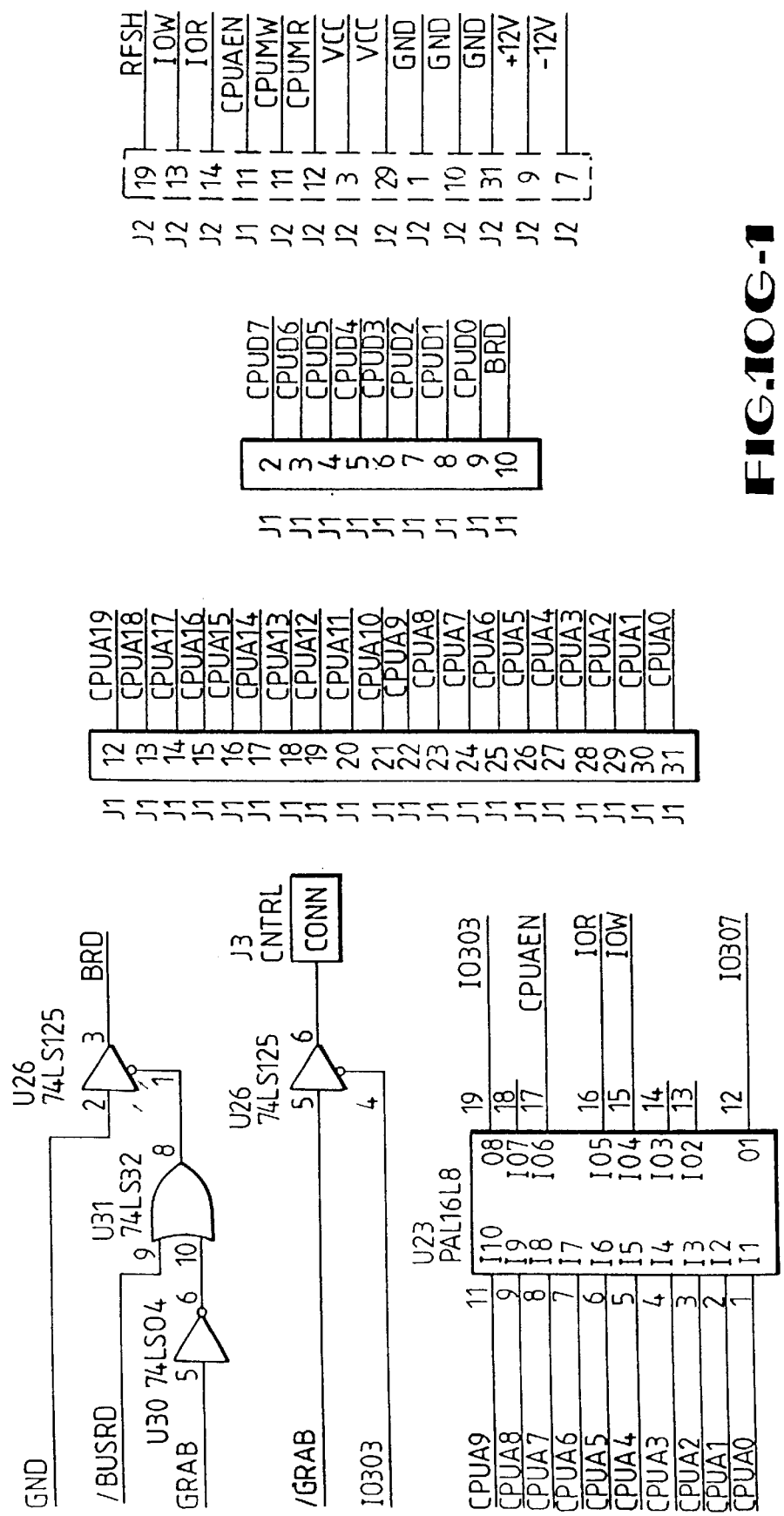
Figures 2, 10G:
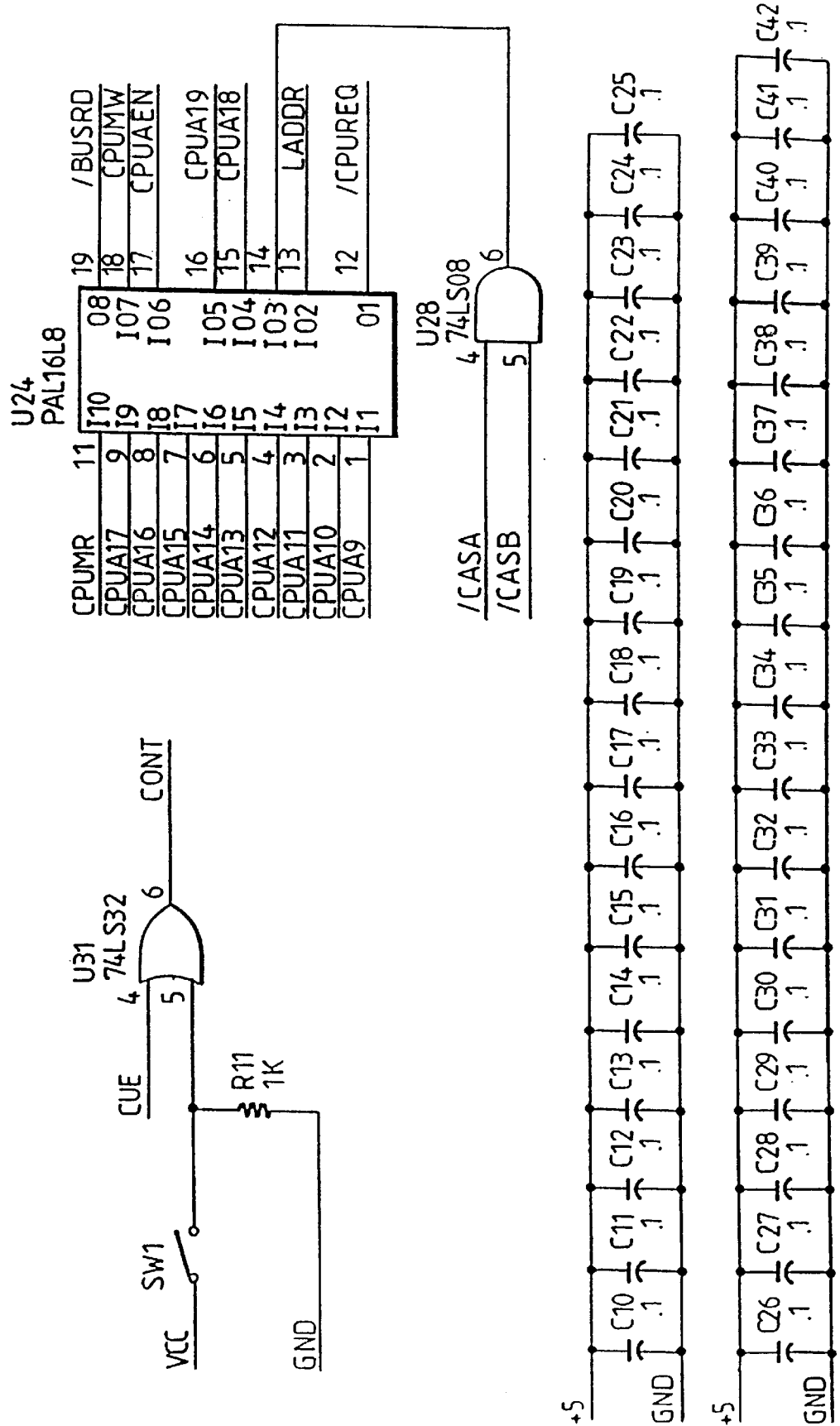

FIGS. 5A, 5B and 5C show the focusing aid in detail. An LED 121 is held in place by an LED holder 122. The tube 126 encases the focusing aid. A spacer 123 fits inside the tube 126 along with lens one (f=84 mm) 125 and lens two (f=48 mm) 124. The focusing aid is secured to the optical assembly 58 by the focusing aid mounting collar 127. The LED holder 122 has 38 gauge wire cross hairs 129 attached with epoxy. Focusing aid 130 projects these cross hairs 129 onto the limbus area of the eye. The cross hairs 129 are reflected by the eye back into the optics system and displayed on a video monitor for the operator to observe. In FIG. 9, the operator actuates joy stick 42 bringing the Placido 2 into focus. The operator via the joystick moves the optical assembly 58 along the optical axis 151 as shown in FIG. 6A. This motion moves the optical assembly 58, focusing aid 130 and Placido 2 along the optical axis. The operator observes the focus aid image 103 in FIG. 4A on the video monitor 200 in FIG. 1. The focus aid image is reflected off of the limbus region of the cornea into the optics assembly into the camera where it is displayed on the video monitor 200. The angle of incidence 170 in FIG. 6A of the focus aid image upon the eye changes as the focusing aid travels along the axis 151. When the angle of incidence is proper, the cross hairs split the circle projected from the focusing aid into equal quadrants and the focusing aid is properly focused at the correct distance to take a shot of the Placido properly focused on the cornea That is when the focus aid is at the proper distance and in focus as indicated by the cross hairs positioned shown as in FIG. 6C, the Placido is also at the correct distance and properly in focus. This technique gives repeatable and consistent results.

When the cross hairs 129 in FIG. 5B are seen as shown in FIG. 6C the Placido is focused at a repeatable distance from the eye each time before and after corneal surgery because of this precise focusing technique upon the limbral region of the cornea. Changes in the central shape of the cornea have a negligible effect upon the focus distance and therefore introduce little error into the analysis of the cornea. Hence the measurements are repeatable and negligible error is induced by a change in the reference point. The operator adjusts the focusing aid and placid reference distance using a calibrated sphere with a known radius of curvature.

Frame Grabber Board

The present system in accordance with the invention takes a digital picture of the Placido as it is reflected by the cornea using the CCD camera. The frame grabber board stores this image by grabbing two (even and odd) consecutive NTSC video fields 1/60 of a second apart, storing them in memory to form a NTSC video frame giving a composite image for viewing by the operator. The board also enables the operator to actuate the frame grabber via a foot switch. The board is designed to work at high speed with the computer and software. The design details and schematic, as well as the programmable logic array equations, are presented in FIGS. 10A through 10K.

Edge Detection and Analysis

The illustrative system in accordance with the invention looks at the Placido reflection from the cornea and determines the position of the edges of the light and dark pattern generated by the Placido. The edge detection and analysis software is set out in the appendix.

Placido Selection and Design

Different types and shapes for the Placido may be used. In a cylindrical Placido the rings are marked around the inside of the tubular surface to generate a pattern of rings when projected onto the cornea. However, in this arrangement the distance from the Placido to the eye is very short, usually less than 1" and most likely right on top of the eye. A planar Placido increases the distance from the Placido to the eye and in the present embodiment is at approximately 3". Increasing this working distance from the Placido decreases the effect of positioning errors. Ihat is an error of 1/10" is a much smaller percentage of 3" than it is of 1" so that as an error of 1/10" has much less effect on the measurements using a planar Placido with a working distance of approximately 3", than a cylindrical Placido with a working distance of 1".

The generic design of the Placido is set out in the mathematical model below. In a planar Placido the inner bands of the Placido are thinner than the outer bands to generate a 50% duty cycle between light and dark edges in the reflected Placido image off of a normal cornea. The Placido can be designed to generate a 50% duty cycle of light and dark edges in the reflected Placido image or any other duty cycle or variable duty cycle desired. The Placido can be designed for any shape also using the mathematical model set forth below. The design of the Placido is a generalized design and is set out below as a mathematical model. This model works for any shape Placido. The design model tells the operator where to put the Placido edges on any shape Placido. For any shape Placido the operator must mark edges on the shape and the mathematical model tells the operator where to mark the edges on the shape.

The Placido generates a virtual image on the convex cornea. The image actually exists behind the surface of the cornea, so when the operator focuses, the focus is on a point internal to the eye where the virtual image exists. This virtual image of the Placido is object of the camera. The virtual image is a series of rings. Using this design method and a planar Placido increases the working distance, which is more comfortable for the patient and less difficult to position.

Mathematical Model for Placido

Each larger successive concentric Placido ring is wider to reflect a nominally uniform width set of rings in the cornea.

The normal angle with respect to optical axis at point yi (2.y1 dia zone) is given by a =sin−1 [y1/7.937], where 7.937 is the radius of curvature at a 42.5 diopter surface. For a reflected ray from point y1 to be parallel to the optical axis, it follows that the angle of incidence of that ray (on point y1) be $$<ia=<r.$$

This ray emanates from a ring edge on the Placido making the enter of curvature of a 42.5 diopter surface our origin in a cartesian frame of reference, we have the locus for the Placido point yielding a reflection at the 2Y diameter zone as (y−y 1)=M (x−x1) (equation of a line)
M=Tan 2a (angle of incident ray with respect to x axis)
Since (y1)^2+(x1)^2=(7.937)2 (equation of 42.5 Diopter surface)
Therefore, Y=X tan 2a+[Y1−(tan 2a) (7.937^2−Y1^2)^1/2]

3) ie:

$$Y = X\left[\tan 2\left(\sin - 1 \frac{Y1}{7.937}\right)\right] + \left[Y1 - \tan 2\left(\sin - 1 \frac{Y1}{7.937}\right)\right](7.95^- Y1^2)]1/2$$

is the focus of Placido points yielding a 2 Y1 diameter reflect on a 42.5 D surface.

The tip of the 42.5 D surface is at 7.937 mm=0.3125".

Choosing an x (eye clearance is x−0.3125 inches) yields an ordered pair (X,Y) for the Placido profile. Note that Y Max will be the overall diameter of the Placido (X Max, Y Max) if Y1=Max desired zone covered. Choose Y2=Min desired zone covered Y=⅞"/2 yields (X Min, Y Max) for Placido inside circle for a conical Placido, the focus of Placido points is $$\frac{X - X\text{Max}}{Y - \text{Max}} + \frac{X - X\text{Min}}{Y - Y\text{Min}}$$

4) ie:

$$Y = X \frac{(Y\text{Max} - Y\text{Min})}{(X\text{Max} - X\text{Min})} + \frac{(X\text{Max}Y\text{Min} - X\text{Min}Y\text{Max})}{(Y\text{Max} - X\text{Min})}$$

and the solution of 4)+3) yield edge radii.
NOTE: Conical Placido profile has been used here but the theory obviously extends to any desired profile, from cylindrical to planar

Optical Assembly

The optical assembly houses a power supply and electronics, illuminating lamp, a camera, the optics, a Placido and the focusing aid. The camera sits inside the optical assembly and behind a plate. The camera has an optical tube that contains a lens which passes through the plate and projects all the way forward to the Placido. The tube surrounds the optical path of the Placido image. The fluorescent lamp that illuminates the Placido sits in front of the plate. The shape of the housing eliminates the need for a reflector pan as the housing serves as a reflector behind the lamp that illuminates the Placido. The purpose is to have a homogeneous light source to illuminate the Placido.

The optical assembly is detailed in FIGS. 8A–8I. The layout and design of the optical path is set out in FIGS. 11A and 11B. The optical path in the current embodiment is a single lens system taking a magnification of 0.58 for 12 mm coverage so the doctor can see slightly more area than the eye itself. The design can accommodate various lens sizes. For example for a 75 mm lens, the total path length of the tube is approximately 8 inches. The outside diameter of the tube is 1 ¼" and has 3 baffles with ¾" apertures.

Magnification is important to the resolution of the system. The pixel resolution of the system is proportional to the magnification of the lens. More magnification means more pixels per millimeter and less resolution. The more pixels per millimeter that are present the better one can analyze small changes across that distance. For example, if you have 5 pixels per millimeter you can resolve a pixel ⅕ of a millimeter in size. If you have 10 pixels per millimeter you can resolve a pixel ¹⁄₁₀ of a millimeter in size.

Power Supply Board

The power supply board is specifically designed to work with the present system in accordance with the invention and is presented in detail in FIG. 9.

Contact Lens Fitting System

The system in accordance with the invention includes a contact lens fitting system including software in which the corneal analysis generated inputs into a transformation function operating in software. The transformation function converts the corneal topographic profile parameters into contact lens design parameters. These contact lens design parameters are sent to a contact lens lathe, well known in the art, to sculpt a custom contact lens to fit the eye that has been analyzed. The contact lens design parameters may be checked for quality control before sending the parameters to the lathe or the parameters can be sent to the lathe without such a quality control checking function and simply let the patient and physician determine if the lens is satisfactory. A software function (or equivalent) to transfer the contact lens parameters from the corneal analysis computer to a lathe for sculpting a lens is necessary to implement the system. One such quality control function has been developed by Polytech, Division of EMI-MEC, Limited, a Sunleaigh Company, School Lane, Chandler Ford, East Leigh, Hempshire, England, S05 3ZE. The present system in accordance with the invention does not claim the Polytech version of the quality control function. The software for the transformation from corneal parameters to contact lens design parameters and the link software from the design parameters are available in source listing form in the appendix to the specification.

The communications software that sends a file from the corneal topography analyzer computer to any other computer utilizes an off the shelf package available from Blaise Computing, Inc., 2560 Ninth St., Suite 316, Berkley, Calif., (415) 540–5441.

Checkered Placido

A ray passing through a point on a checkered Placido, reflected off a cornea, and detected by a CCD camera is graphically depicted in FIG. 15. The focal plane 40 of the CCD camera, the plane of the lens 42, the plane of the Placido 44 and the plane 46 tangential to the apex of the cornea are depicted in FIG. 15. Each plane contains a local XY coordinate system. The origin of the XY coordinate system existing in each plane is intersected by a line 48 representing the optical axis of the eye. Each plane is parallel to the other planes. The optical axis is coincident with the origin of the coordinate system in each plane. Point "A" 50 lies on the Placido 44. A line intersecting point "A"

50 and the origin of the XY coordinate system lying in the Placido plane 44 forms an angle "a" 52 with the horizontal axis or X axis of the XY Placido coordinate system.

Figure 18:
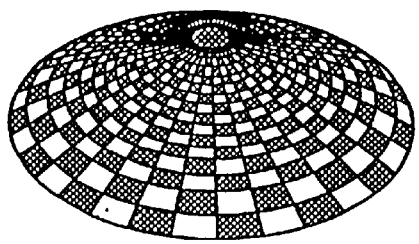
FIG. 18 is a diagonal view of a checkered Placido apparatus.

As shown in FIG. 18 the Placido in an illustrative embodiment is shaped like a cone. In an alternative embodiment, the Placido could be a paraboloid. In yet another alternative embodiment, the Placido could be yet another shaped surface. The patient looks into the concave surface of the conical Placido in a preferred embodiment. The exterior or convex surface of the conical Placido in a preferred embodiment is backlit by a light source. Point A 50 represents a point on the Placido. A ray of light from the light source will pass through point "A" on the Placido and strike a reflection point 58. This ray is called the incident ray 56. The incident ray 56 passes through Placido point "A'" 50 and is reflected at the reflection point 58. The reflected ray 60 is detected point "A" 62 on the CCD focal plane 40. A line 64 passing through detected at point 62 and through the origin of the coordinate system existing in CCD plane 40 forms an angle "a$^1$" 66 with the horizontal axis or X axis of the CCD plane coordinate system.

Figure 19:
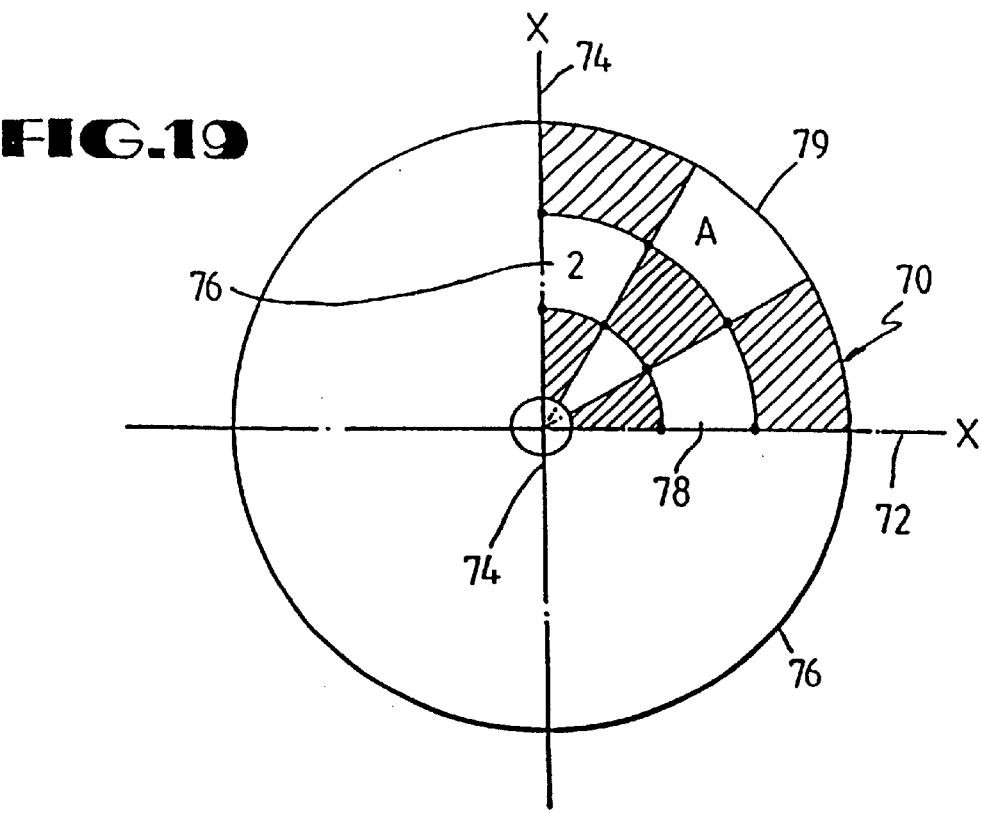
FIG. 19 is a front view of a checkered Placido apparatus.

Referring now to FIG. 19 a front view of the checkered Placido, the Placido is laid out in a checkered pattern. In a preferred embodiment, the checkered Placido is made up of black and white sections. In an alternative embodiment, the checkered Placido could be made up of another set of contrasting colors. The checkered pattern is designed so that black and white transitions are encountered when traveling along a radius drawn from the origin 74 to the outer edge 76 of the Placido as concentric rings of contrasting color are encountered. The design also provides for black and white transitions when traveling along an arc 78. The arc 78 is generated by angularly rotating a point drawn a distance R from the origin 74 where R is less than the radius of the Placido perimeter 76. Thus, edge transitions are encountered when traveling along a concentric circle drawn inside the perimeter of the Placido circumference as adjacent sections of contrasting color are encountered. These sections are formed by drawing a plurality of radii to form the triangular shaped sections shown in FIG. 19. Upon drawing a plurality of radii there will be edge transitions encountered both radially and concentrically in the pattern. There will exist points on this pattern which will have edge transitions both radially and concentrically. These points will be defined as nodal points where it is possible for direct measure of orthogonal radius of curvatures, radially and concentrically.

A benefit of the checkered Placido is that, as shown in FIG. 15 with the checkered Placido, the meridian of the incident ray can be determined by construction. Therefore when the meridian of the reflected ray is measured it is possible to determine the precise orientation of the surface normal at the reflecting point. Referring again to FIG. 15, in the past it was assumed that the incident ray, the surface normal and the reflected ray were contained in a single plane. This plane was assumed to contain the principle or optical axis. However, this is not necessarily true. It depends on the precise orientation of the surface normal at the reflecting point or the shape of the surface at the reflection point.

When the reflection point is located on a perfectly spherical surface the principle axis or optical axis is located in the plane containing the incident ray, the surface normal and the reflected ray. However, when the reflection point is located on a non spherical surface, such as a cornea having non spherical characteristics, then the optical axis is not located in the plane containing the incident ray the surface normal and the reflected ray.

In the checkered Placido the angle or meridian of the incident ray can be determined because the checkered Placido has a marking or identifying line at the X axis in the coordinate system for the Placido plane. Thus, the deflection angle 79 of a line drawn through a point "B" 50 on the Placido plane can be determined. Thus, the XY coordinates of the point "A" 50 on the Placido plane are known. At nodal points there will be a unique surface normal in three dimensions readily defined since the edge transitions occur in orthogonal curvatures.

Referring now to FIG. 15, in a system with a Placido consisting only of concentric rings, not having the checkered pattern of the present embodiment, it was assumed that the angle "a" 52 measuring the angular deflection from the horizontal of the point "A" on the Placido plane, and the angle "a'" 66 measuring the angular deflection from horizontal of the point "a'" 62 the detected point on the CCD image plane, were the same. That is, it was assumed that the angular deflection of the point on the Placido plane and the angular deflection of the point on the detected CCD image were the same. However, this assumption is not necessarily true when the reflection point is located on a surface that is not perfectly spherical.

The point "A" 50 is reflected at the reflection point 58 and passes through the lens center represented by the origin of the lens plane coordinate system 42 and forms an image on the CCD focal plane. There is also a parallel ray from a virtual image, which is behind the eye. The parallel and the principal ray or chief ray converge at point 62 to determine where the image is formed. The system graphically depicted in FIG. 15 has been designed to form the image at the CCD focal plane so that only the principal ray is a concern in the calculation.

Previously it was assumed that the angle 52 was equal to the angle 66 because there was no way easy to determine where the point 50 was located in the Placido plane 44. However, with the checkered Placido the location of the point 50 on the Placido plane can be determined because the meridian or the angle "a" 52 is known by construction. The deflection angle or meridian 66 of the detected point dan be measured on the detected CCD image. The angle "a" 52 is known by construction because it lies on or near the intersection of a black to white or color transition edge on the checkered Placido. The angle measured from horizontal to each edge of the black to white or color transition on the Placido is known. Thus, points on or near these transition "edges" can be determined.

The deflection angle "a'" 66 of a detected point can be measured on the CCD. The angle 66 of the detected point will not equal the angle "a" 52 of the point on the Placido when the reflection point is located on a nonspherical surface. Also, when the reflection point is located on an nonspherical surface, the surface normal will be twisted such that the surface normal at the reflection point 58 will not be contained in that plane containing the optical axis. It will be contained instead in a skewed plane. When the angle 52 is not equal to the angle 66, the surface normal is not contained in the plane of the optical axis and the surface containing the reflection point is not spherical.

Therefore the location of the point on the Placido helps determine more precisely the shape of the eye. The checkered Placido helps to determine the location of a point on the Placido by construction. The most obvious points are nodal points where orthogonal edge transitions occur by construction. The determination of the unique surface normal in three dimensions is a direct consequence of knowing the tangent plane at each nodal point common to each of orthogonal local radius of curvature measurements calculated from the respective edge transition locations. The location of any point on the Placido can be determined because the Placido is constructed of black and white or contrasting sections whose edge transitions can be detected and mapped or located so that a map is formed of these known locations of points on the Placido. The angular deflection from horizontal for each black to white or color transition edge is known because the checkered Placido is manufactured with a known deflection angle for each of these transition edges. Knowing the measured angle 66 of the detected point, one can use solid geometry to go from point 62 on the CCD image through the lens center back to the reflection point on the cornea of the eye and back to a known point "A" on the checkered Placido. The angle 52 determines the surface normal of the reflection point in three-dimensional coordinates. These three-dimensional coordinates define precisely the orientation of the surface normal at the reflection point ($N_X$, $N_Y$, and $N_Z$). This triplet identifies the surface normal at the reflection point. The surface normal triplet can be determined for every point on the cornea where a measurement is taken.

Any line originating from the center of a sphere and intersecting the surface of the sphere is a normal. In nonspherical volume there may be a significant perturbation away from a triplet for a normal on a spherical surface. The checkered Placido helps to determine this perturbation or delta. Determining this perturbation or delta enables the corneal analysis system to determine more precisely the topographical or non-spherical characteristics of the surface of the cornea at the reflection point.

Points on the Placido are mapped based on the angular deflection of the point from that zeroth meridian or horizontal axis. Each edge at a color transitions is a known number of degrees from the horizontal. The radial Placido sections are constructed by drawing radii so that each section is a known number of degrees from horizontal. For example, if each radial section is 10 degrees wide the angular deflection between the horizontal or zeroth meridian and the edge of the first section would be 10 degrees, 20 degrees to the second section edge, 30 degrees to the third section edge, and so on. The black to white edges or color transition edges formed by the adjoining radial sections encountered in the angular direction are detected by the same edge detection and location method as used for the edges of the concentric circles encountered in the radial direction. In a preferred embodiment, adjacent sections on the Placido are alternately black and white, however, the adjacent sections can be another set of contrasting colors, as long as a detectable edge is formed between adjacent sections, to facilitate locating points on the Placido.

The edges or color transitions are determined by the mathematical process of differentiation. The derivative function highlights these edges by generating an impulsive change. The impulsive change is used to determine the precise position of the edge of the black to white or color transition between two pixels. The position is determined to a sub-pixel position by a process of weighting and using the surrounding pixel information to determine where between the two pixels the edge is precisely located.

The surface normal is calculated by drawing a line from the detected point 62 to the reflection point and drawing a line from the reflection point to point 50 on the Placido. The angle bisecting the angle between these two lines is the surface normal.

A successive approximation process is used to determine the reflection point at which the surface normal intersects the eye.

Knowing the location of the detected point 62, the lens center point and the location of the Placido point 50, and reflection point one can calculate the surface normal. A line is drawn from point 62 through a point at the origin of the lens coordinate system 42 or the center of the lens. This line 60 is extended to intersect the plane of the reflection point. A plane which contains the line extended through point 62 and the center of the lens is rotated until it touches the point 50 on the Placido. The X and the Y coordinate of the surface normal are determined. The Z coordinate of the surface normal is then determined. Once the three coordinates of the surface normal are known-for a number of points, a plane can be drawn orthogonal to each surface normal. The planes can be joined together to form a multi-faceted surface area. This area of facets or joined planes can be smoothed to represent the surface contour of the cornea. That is, the faceted surface is integrated to smooth the faceted surface to represent the actual contour of the cornea. Points in between the surface normal are calculated by the process of interpolation. The actual contour of the cornea can be further described; for example, by calculating, among possible curvatures, the mean curvature, either arithmetic or geometric (Gaussian), at an infinitely small area when two orthonogal or principal radius of curvatures are known. The local area surrounding an nodal point can be directly analyzed to provide these mean curvature measurements either arithmetic or geometric (Gaussian) to describe more precisely the local radius of curvature of the cornea's contour. FIG. 19 demonstrates this calculation where a nodal point analysis containes orthogonal edge transition for determining the local radius of curvature in orthonogal direction which can be mathematically manipulated to provide the arithmetic or geometric (Gaussian) mean of the lcoal radius of curvature to provide more precise analysis of the cornea's contour. This process provides novel capability to determine the contour of the cornea and therefore its refractive power as an optical element necessary for vision by the eye. Historically, curvature measurements had only been made in a radial fashion from the optical axis of the cornea outward, peripherally. Mean curvature calculation from measurement of orthonogal local radius of curvatures will further enhance our understanding of the cornea contour and its shape in addition to its optical performance. This process more precisely defines the surface of the eye.

$$\text{Arithmetic } R \text{ mean} = \frac{R_1 + R_2}{2}$$

or $$\text{Geometric } R \text{ mean} = \sqrt{R_1 \bullet R_2}$$

At times it may be difficult to know exactly what ring on the Placido corresponds to the ring detected in the CCD digital image. This may be due to corneal distortion, surgical scarring, or some other optical aberation that obliterates data in the digital image so that an edge becomes undetectable. As explained above, it is advantageous to know which ring or section on the Placido corresponds to the ring or section detected in the CCD digial image. Ring seven may be mistaken for ring six, for example, if the edge between ring five and six is not detected and not counted, thus skipped. In an illustrative embodiment, as shown in FIG. 19, a reference mark 76 or numeral is placed on the Placido to a ring or section on the Placido.

Figure 20:
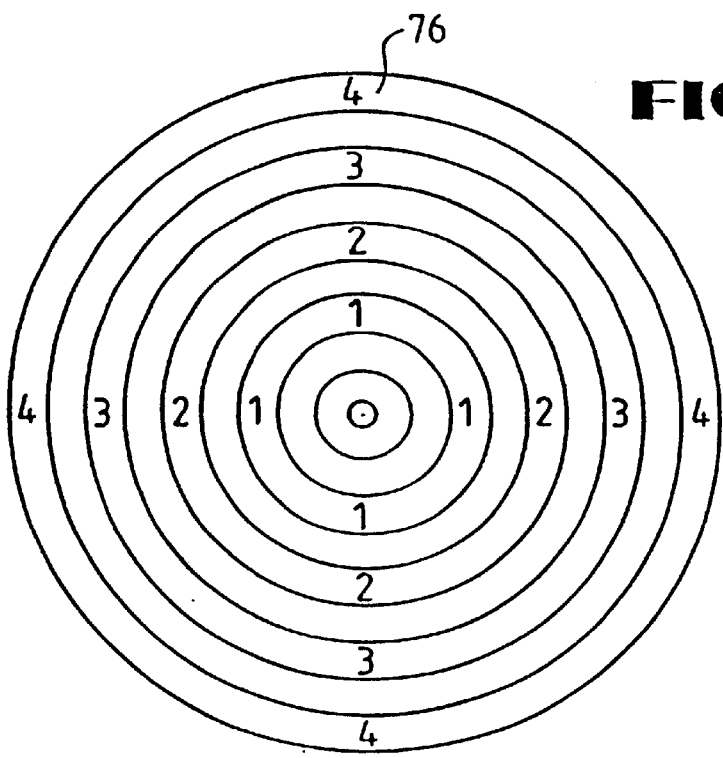
FIG. 20 is a front view of a Placido.
Figure 21:
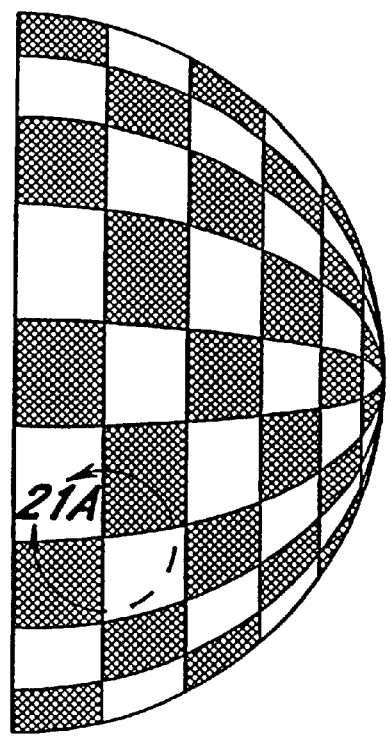
FIG. 21 is a side view of a checkered Placido image projected onto a cornea and an expanded view of a selected nodal point.
Figure 21A:
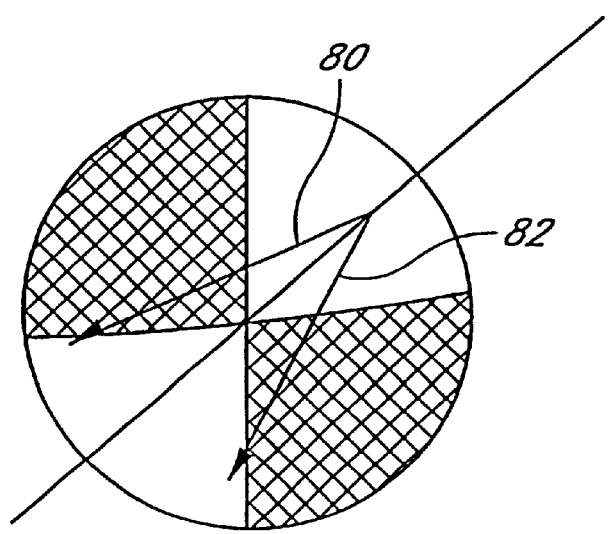

As shown in FIG. 20, reference marks or numerals enhance correlation of points on the CCD digital image and corresponding points on the Placido. In an illustrative embodiment, reference marks or numerals are placed in each white ring. Four lines of reference numerals are placed respectively at zero degrees, ninety degrees, one hundred eighty degrees, and two hundred seventy degrees to facilitate checking of each of the quadrants.

Even though the reference marks may undergo distortions, including scale, perspective, and rotation, when reflected of a non-spherical surface, the system can find the section containing the reference mark. The system will do a mapping back into a normalized space to obtain a normalized detected reference mark. In normalized space there is a library in which templates are stored for the reference marks or numerals as detected when reflected from calibrated spheres. The system correlates the stored template mark or numeral from the library with the normalized detected reference mark or numeral to confirm which ring or section on the Placido corresponds to the detected ring or section.

The normalization of reference marks allows the system to recognize numerals or marks that have undergone translation, rotation, and rubber-sheeting type of perspective distortion.

While an embodiment of the present system in accordance with the invention has been described herein, it will be understood that a person skilled in the art may make minor alternations or substitute circuitry and apparatus other than that described without departing from the spirit of the invention. For example, those of ordinary skill having the benefit of this disclosure will of course recognized that the "hard-wired" discrete logic function described herein may alternatively and equivalently be implemented in software, i.e., through suitable programming of a processor system equipped with a suitable processor and a memory or other storage device. Such a software implementation would be a matter of routine for those of ordinary skill having the benefit of this disclosure and knowledge of the processor system in question. Software functions disclosed in this application could likewise be implemented in hardware by a person having ordinary skill and the benefit of this disclosure.

What is claimed is:

1. A method of corneal analysis using a webbed placido comprising:
   projecting an image of a spider-webbed placido onto a cornea;
   detecting a reflected image of said spider-webbed placido reflected off of said cornea;
   detecting a plurality of nodal points from said reflected image of said spider-webbed placido;
   determining a plurality of surface normals to a surface of said cornea at corresponding ones of said plurality of nodal points; and
   analyzing said plurality of surface normals to estimate an actual curvature of said cornea.

2. The method of corneal analysis using a webbed placido according to claim 1, further comprising:
   using said plurality of surface normals to determine a plurality of planes which define a multi-faceted surface area that is indicative of a radius of curvature of said cornea.

3. The method of corneal analysis using a webbed placido according to claim 2, further comprising:
   smoothing said multi-faceted surface to represent an actual contour of said cornea.

4. The method of corneal analysis using a webbed placido according to claim 3, further comprising:
   determining a mean curvature at a point where said actual curvature is known.

5. The method of corneal analysis using a webbed placido according to claim 4, wherein:
   said point is determined from said step of analyzing said plurality of surface normals.

6. The method of corneal analysis using a webbed placido according to claim 3, wherein said smoothing comprises:
   an integration of said multi-faceted surface.

7. The method of corneal analysis using a webbed placido according to claim 1, further comprising:
   producing a graphical display of said estimated actual curvature of said cornea.

8. Apparatus for analyzing a cornea, comprising:
   means for projecting an image of a webbed placido onto a cornea;
   means for detecting a reflected image of said webbed placido reflected off of said cornea;
   means for determining a plurality of nodal points from said detected, reflected of said webbed placido;
   means for determining a plurality of surface normals to a surface of said cornea at corresponding ones of said plurality of nodal points; and
   means for analyzing said plurality of surface normals to estimate an actual curvature of said cornea.

9. The apparatus for analyzing a cornea according to claim 8, further comprising:
   a display to show said estimated actual curvature of said cornea.

10. The apparatus for analyzing a cornea according to claim 8, wherein:
    said webbed image of said placido is a spider-webbed image.

11. The apparatus for analyzing a cornea according to claim 10, further comprising:
    a display to show said estimated actual curvature of said cornea.

12. The apparatus for analyzing a cornea according to claim 8, wherein:
    said webbed image of said placido is a spider-webbed image.

13. The apparatus for analyzing a cornea according to claim 8, further comprising:
    means for using said plurality of surface normals to determine a plurality of planes which define a multi-faceted surface area that is indicative of a radius of curvature of said cornea.

14. The apparatus for analyzing a cornea according to claim 10, further comprising:
    means for smoothing said multi-faceted surface to represent an actual contour of said cornea.

15. The apparatus for analyzing a cornea according to claim 14, further comprising:
    means for determining a mean curvature at a point where said actual curvature is known.

16. The apparatus for analyzing a cornea according to claim 15, wherein:
    said means for analyzing determines said point.

17. The apparatus for analyzing a cornea according to claim 14, wherein said means for smoothing comprises:
    means for integrating said multi-faceted surface.

18. Apparatus for analyzing a cornea, comprising:
    a webbed placido image to be projected onto a cornea;
    a detector to detect a reflected image of said webbed placido reflected off of said cornea; and a processor adapted to estimate an actual curvature of said cornea form a plurality of normals to a surface of said cornea at corresponding ones of a plurality of nodal points determined form said detected, reflected image of said webbed placido.

19. The apparatus for analyzing a cornea according to claim 18, wherein;

said processor is further adapted to use said plurality of surface normals to determine a plurality of planes which define a multi-faceted surface area that is indicative of a radius of curvature of said cornea.

20. The apparatus for analyzing a cornea according to claim 19, wherein:

said processor is further adapted to determine a mean curvature at a point where said actual curvature is known.

21. The apparatus for analyzing a cornea according to claim 19, wherein:

said processor integrates said multi-faceted surface to accomplish said smoothing.

22. The apparatus for analyzing a cornea according to claim 18, wherein:

said processor is further adapted to smooth said multi-faceted surface to represent an actual contour of said cornea.

* * * * *